US012312606B2

(12) United States Patent
Goepfert et al.

(10) Patent No.: US 12,312,606 B2
(45) Date of Patent: May 27, 2025

(54) NUCLEIC ACID CONSTRUCTS FOR VA RNA TRANSCRIPTION

(71) Applicant: Hoffmann-La Roche Inc., Little Falls, NJ (US)

(72) Inventors: Ulrich Goepfert, Penzberg (DE); Simon Auslaender, Wolfratshausen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 245 days.

(21) Appl. No.: 17/500,778

(22) Filed: Oct. 13, 2021

(65) Prior Publication Data

US 2022/0135954 A1 May 5, 2022

(30) Foreign Application Priority Data

Oct. 15, 2020 (EP) .................................... 20202010

(51) Int. Cl.
*C12N 7/00* (2006.01)
*C12N 5/071* (2010.01)
*C12N 15/86* (2006.01)

(52) U.S. Cl.
CPC ............. *C12N 7/00* (2013.01); *C12N 5/0682* (2013.01); *C12N 15/86* (2013.01); *C12N 2750/14121* (2013.01); *C12N 2750/14123* (2013.01); *C12N 2750/14143* (2013.01); *C12N 2750/14152* (2013.01); *C12N 2830/008* (2013.01)

(58) Field of Classification Search
None
See application file for complete search history.

(56) References Cited

U.S. PATENT DOCUMENTS 4,797,368 A 1/1989 Carter et al.
5,139,941 A 8/1992 Muzyeska et al.
5,173,414 A 12/1992 Lebkowski et al.
5,279,833 A 1/1994 Rose et al.
5,998,205 A 12/1999 Hallenbeck et al.
6,001,650 A 12/1999 Colosi et al.
6,004,797 A 12/1999 Colosi et al.
6,093,699 A 7/2000 Sehon et al.
6,100,242 A 8/2000 Hammond et al.
6,228,646 B1 5/2001 Hardy et al.
6,274,354 B1 8/2001 Wilson et al.
6,291,214 B1 9/2001 Richards et al.
6,303,302 B1 10/2001 Rupp. et al.
6,303,327 B1 10/2001 VonMelchner et al.
6,376,237 B1 4/2002 Colosi et al.
7,189,561 B2 3/2007 Graham et al.
7,267,979 B2 9/2007 Yadav et al.
7,449,179 B2 11/2008 Xin et al.
7,972,857 B2 7/2011 Ow et al.
2003/0207439 A1 11/2003 Wright et al.
2006/0110390 A1 5/2006 Leinwand et al.
2007/0122798 A1 5/2007 Barcellini-Couget et al.
2012/0135515 A1 5/2012 Qu et al.
2013/0059732 A1 3/2013 Lisowski et al.
2013/0072548 A1 3/2013 Wright et al.
2015/0020223 A1 1/2015 Zhang et al.

FOREIGN PATENT DOCUMENTS

EP 1225229 A1 7/2002
EP 1309709 A2 5/2003
EP 1230354 B1 1/2004
EP 1064393 A1 12/2004
EP 1064393 B1 12/2004
EP 1512742 A1 3/2005
EP 0942999 B1 5/2005
EP 1383891 B1 12/2005
EP 0953647 B1 5/2008
EP 0850313 B1 11/2008
EP 3209785 B1 7/2019
JP H-1033175 A 2/1998
WO 91/06309 A1 5/1991
WO 92/08796 A1 5/1992
WO 93/024640 A2 12/1993
WO 93/024641 A2 12/1993
WO 94/17810 A1 8/1994
WO 94/23744 A1 10/1994
WO 94/026877 A1 11/1994
WO 94/28143 A1 12/1994
WO 97/009441 A2 3/1997
WO 97/17458 A1 5/1997
WO 98/10086 A1 3/1998
WO 98/02707 A1 6/1998
WO 98/024918 A1 6/1998
WO 98/27207 A1 6/1998
WO 98/27217 A1 6/1998

(Continued)

OTHER PUBLICATIONS

Shieh WJ. Biomed J. Feb. 2022;45(1):38-49. doi: 10.1016/j.bj.2021.08.009. Epub Sep. 10, 2021. PMID: 34506970. (Year: 2021).*

Pei Z, Shi G, Kondo S, Ito M, Maekawa A, Suzuki M, Saito I, Suzuki T, Kanegae Y. Adenovirus vectors lacking virus-associated RNA expression enhance shRNA activity to suppress hepatitis C virus replication. Sci Rep. Dec. 20, 2013;3:3575. doi: 10.1038/srep03575. PMID: 24356586. (Year: 2013).*

Machitani M, Katayama K, Sakurai F, Matsui H, Yamaguchi T, Suzuki T, Miyoshi H, Kawabata K, Mizuguchi H. Development of an adenovirus vector lacking the expression of virus-associated RNAs. J Control Release. Sep. 25, 2011; 154(3):285-9. Epub Jun. 16, 2011. PMID: 21703313. (Year: 2011).*

(Continued)

*Primary Examiner* — Benjamin P Blumel
*Assistant Examiner* — Jeffrey Mark Sifford
(74) *Attorney, Agent, or Firm* — Daphne Reddy

(57) ABSTRACT

Herein is reported a novel adenoviral VA RNA nucleic acid wherein the wild-type type 2 polymerase III promoter has been removed and an U6-snRNA promoter or an inducible promoter has been added.

6 Claims, 2 Drawing Sheets

Specification includes a Sequence Listing.

(56) References Cited

FOREIGN PATENT DOCUMENTS

| | | | |
|---|---|---|---|
| WO | 01/036615 | A2 | 5/2001 |
| WO | 01/066774 | A1 | 9/2001 |
| WO | 01/83797 | A2 | 11/2001 |
| WO | 02/08409 | A2 | 1/2002 |
| WO | 02/12455 | A1 | 2/2002 |
| WO | 02/40685 | A2 | 5/2002 |
| WO | 02/088353 | A2 | 11/2002 |
| WO | 03/074686 | A1 | 9/2003 |
| WO | 03/084977 | A1 | 10/2003 |
| WO | 2004/029219 | A2 | 4/2004 |
| WO | 2005/007877 | A2 | 1/2005 |
| WO | 2005/116225 | A1 | 12/2005 |
| WO | 2007/056994 | A2 | 5/2007 |
| WO | 2007/102872 | A2 | 9/2007 |
| WO | 2005/125146 | A1 | 11/2007 |
| WO | 2007/125146 | A1 | 11/2007 |
| WO | 2009/076524 | A2 | 6/2009 |
| WO | 2011/055366 | A1 | 5/2011 |
| WO | 2013/158879 | A1 | 10/2013 |
| WO | 2013/188522 | A2 | 12/2013 |
| WO | 2014/117045 | A2 | 7/2014 |
| WO | 2015/013313 | A2 | 1/2015 |
| WO | 2015/031686 | A1 | 3/2015 |
| WO | 2015/031686 | A9 | 3/2015 |
| WO | 2016057800 | A1 | 4/2016 |
| WO | 2017/096039 | A1 | 6/2017 |
| WO | 2017/189683 | A1 | 11/2017 |
| WO | 2018/096356 | A1 | 5/2018 |
| WO | 2018/150271 | A1 | 8/2018 |
| WO | 2018/226887 | A1 | 12/2018 |
| WO | 2018/229276 | A1 | 12/2018 |
| WO | 2019/006390 | A1 | 1/2019 |
| WO | 2019/057691 | A1 | 3/2019 |
| WO | 2019/126634 | A2 | 6/2019 |
| WO | 2020/078953 | A1 | 4/2020 |
| WO | 2020/132059 | A1 | 6/2020 |

OTHER PUBLICATIONS

Albert, H., et al., "Site-specific integration of DNA into wild-type and mutant lox sites placed in the plant genome" Plant J 7(4):649-659 (Apr. 1, 1995).
Ali, M., et al., "The use of DNA viruses as vectors for gene therapy" Gene Ther 1(6):367-384 (Nov. 1, 1994).
Allen, J., et al., "Identification and elimination of replication-competent adeno-associated virus (AAV) that can arise by non-homologous recombination during AAV vector production" J Virol 71(9):6816-6822 (Sep. 1, 1997).
Andersson, M. G., et al., "Suppression of RNA Interference by Adenovirus Virus-Associated RNA" J Virol 79(15):9556-9565 (Aug. 1, 2005).
Araki, K., et al., "Comparative analysis of right element mutant lox sites on recombination efficiency in embryonic stem cells" BMC Biotechnol 10(29):1-9 (Mar. 31, 2010).
Arguello, T., et al., "Cre recombinase activity is inhibited in vivo but not ex vivo by a mutation in the asymmetric spacer region of the distal loxP site" Genesis 53(11):695-700 (Nov. 1, 2015).
Ausubel, F.M., et al. Current Protocols in Molecular Biology New York, N.Y., USA: John Wiley and Sons, Inc., vol. I-III (Jan. 1, 1997).
Balakrishnan, B., et al., "Basic Biology of Adeno-Associated Virus (AAV) Vectors Used in Gene Therapy" Curr Gene Ther 14(2):86-100 (Apr. 1, 2014).
Baldi, L., et al., "Recombinant protein production by large-scale transient gene expression in mammalian cells: state of the art and future perspectives" Biotechnol Lett 29(5):677-684 (May 1, 2007).
Berns, K, et al., "Adenovirus and Adeno-Associated Virus as Vectors for Gene Therapy" Ann NY Academy Sci 772(1):95-104 (Nov. 1, 1995).
Berns, K., et al., "Adeno-Associated Viruses: An Update" Adv Virus Res 32:243-306 (Jan. 1, 1987).
Berthet, C., et al., "How adeno-associated virus Rep78 protein arrests cells completely in S phase" PNAS 102(38):13634-13639 (Sep. 12, 2005).
Bessen, J., et al., "High-resolution specificity profiling and off-target prediction for site-specific DNA recombinases" Nat Comm 10(1937):1-13 (Apr. 26, 2019).
Bonifacino, J., et al., "Commonly Used Techniques: Molecular Biology Techniques" Curr Protocols in Cell Biol 8(1):1-4 (Oct. 1, 2000).
Bouabe, H., et al. Virus-Host Interactions: Methods and Protocols "Chapter 23: Gene Targeting in Mice: A Review" Bailer, S., & Lieber, D., eds., First edition, Totowa, New Jersey—US: Humana Press, vol. 1940:315-336 (Sep. 1, 2013).
Branda, C., et al., "Talking about a Revolution: The Impact of Site-Specific Recombinases on Genetic Analyses in Mice" Develop Cell 6(1):7-28 (Jan. 1, 2004).
Buchschacher, G., et al., "Human immunodeficiency virus vectors for inducible expression of foreign genes" J Virol 66(5):2731-2739 (May 1, 1992).
Burnette, W.N., "'Western Blotting': Electrophoretic transfer of proteins from sodium dodecyl sulfate-polyacrylamide gels to unmodified nitrocellulose and radiographic detection with antibody and radioiodinated protein A" Anal Biochem 112(2):195-203 (Apr. 1, 1981).
Carter, B., et al., "Properties of an adenovirus type 2 mutant, Ad2d/807, having a deletion near the right-hand genome terminus: Failure to help AAV replication" Virology 126(2):505-516 (Apr. 30, 1983).
Celis, J., et al. Cell Biology: A Laboratory Handbook Celis, J., ed., Third edition, New York, USA: Elsevier—Academic Press, vol. I-III:1-638 (Dec. 1, 2006).
Chadeuf, G., et al., "Quantification of adeno-associated virus particles and empty capsids by optical density measurement" Mole Ther 12(4):744-753 (Oct. 1, 2005).
Chatterjee, P., et al., "Mutually exclusive recombination of wild-type and mutant loxP sites in vivo facilitates transposon-mediated deletions from both ends of genomic DNA in PACs" Nucleic Acids Res 32(18):5668-5676 (Jan. 1, 2004).
Chejanovsky, N., et al., "Mutagenesis of an AUG codon in the adeno-associated virus rep gene: Effects on viral DNA replication" Virology 173(1):120-128 (Nov. 1, 1989).
Chiorini, J., et al., "High-efficiency transfer of the T cell co-stimulatory molecule B7-2 to lymphoid cells using high-titer recombinant adeno-associated virus vectors" Hum Gene Ther 6(12):1531-1541 (Dec. 1, 1995).
Chu, G., et al., "SV40 DNA transfection of cells in suspension: analysis of the efficiency of transcription and translation of T-antigen" Gene 13(2):197-202 (Mar. 1, 1981).
Chuang, K., et al., "Novel Heterotypic Rox Sites for Combinatorial Dre Recombination Strategies" G3 Genes Genome Genetics 6(3):559-571 (Dec. 29, 2015).
Clark, K., et al., "Cell lines for the production of recombinant adeno-associated virus" Hum Gene Ther 6(10):1329-1341 (Oct. 1, 1995).
Conway, J., et al., "Recombinant adeno-associated virus type 2 replication and packaging is entirely supported by a herpes simplex virus type 1 amplicon expressing Rep and Cap" J Virol 71(11):8780-8789 (Nov. 1, 1997).
Crawford, Y. et al., "Fast identification of reliable hosts for targeted cell line development from a limited-genome screening using combined qC31 integrase and CRE-Lox technologies" Biotechnol Prog 29(5):1307-1315 (Sep. 1, 2013).
Davis, L. et al. Basic Methods in Molecular Biology Davis, L. & Dibner, M., eds., First edition, Amsterdam, NL: Elsevier B.V.,:1-388 (Jan. 1, 1986).
Doetschman, T., et al., "Targeted correction of a mutant HPRT gene in mouse embryonic stem cells" Nature 330(6148):576-578 (Dec. 10, 1987).
Felgner, P., et al., "Lipofection: a highly efficient, lipid-mediated DNA-transfection procedure" PNAS USA 84(21):7413-7417 (Nov. 1, 1987).

(56) References Cited

OTHER PUBLICATIONS

Ferrari, F., et al., "Second-strand synthesis is a rate-limiting step for efficient transduction by recombinant adeno-associated virus vectors" J Virol 70(5):3227-3234 (May 1, 1996).
Fischer, K., et al., "Sources of off-target expression from recombinase-dependent AAV vectors and mitigation with cross-over insensitive ATG-out vectors" PNAS 116(52):27001-27010 (Dec. 16, 2019).
Fisher, K., et al., "A novel adenovirus-adeno-associated virus hybrid vector that displays efficient rescue and delivery of the AAV genome" Hum Gene Ther 7(17):2079-2087 (Nov. 10, 1996).
Flatman, S., et al., "Process analytics for purification of monoclonal antibodies" J Chromatogr 848(1):79-87 (Mar. 15, 2007).
Flotte, T. et al., "An improved system for packaging recombinant adeno-associated virus vectors capable of in vivo transduction" Gene Ther 2(1):29-37 (Jan. 1, 1995).
Flotte, T., et al., "Expression of the cystic fibrosis transmembrane conductance regulator from a novel adeno-associated virus promoter" J Biol Chem 268(5):3781-3790 (Feb. 15, 1993).
Flotte, T., et al., "Stable in vivo expression of the cystic fibrosis transmembrane conductance regulator with an adeno-associated virus vector" PNAS 90(22):10613-10617 (Nov. 15, 1993).
Freshney, R.I., et al. Culture of Animal Cells: A Manual of Basic Technique New York: Alan R. Liss, Inc.,:1-7 ( 1983).
Gan, Y., et al., "A new combination of mutated loxPs in a vector for construction of phage antibody libraries" Acta Biochim Biophys Sin 37(7):495-500 (Jul. 1, 2005).
Goomer, R., et al., "The transcriptional start site for a human U6 small nuclear RNA gene is dictated by a compound promoter element consisting of the PSE and the TATA box" Nucleic Acids Res 20(18):4903-4912 (Sep. 25, 1992).
Graham, F., et al., "A new technique for the assay of infectivity of human adenovirus 5 DNA" Virology 52(2):456-467 (Apr. 1, 1973).
Graham, F., et al., "Characteristics of a Human Cell Line Transformed by DNA from Human Adenovirus Type 5" J Gen Virol 36(1):59-74 (Feb. 1, 1977).
Grimm, D., et al., "Novel tools for production and purification of recombinant adeno-associated virus vectors" Hum Gene Ther 9(18):2745-2760 (Dec. 10, 1998).
Grimm, D., et al., "Titration of AAV-2 particles via a novel capsid ELISA: packaging of genomes can limit production of recombinant AAV-2" Gene Ther 6(7):1322-1330 (Aug. 9, 1999).
Häcker, I., et al., "Cre/lox-Recombinase-Mediated Cassette Exchange for Reversible Site-Specific Genomic Targeting of the Disease Vector, Aedes aegypti" Sci Rep 7(43883):1-14 (Mar. 7, 2017).
Haddada, H., et al. The Molecular Repertoire of Adenoviruses III: Biology and Pathogenesis "Chapter 14: Gene Therapy Using Adenovirus Vectors" (with Table of Contents, total in 15 pages), Doerfler, W. & Bohm, P., eds., First edition, Heidelberg, Germany: Springer-Verlag,:297-306 (Jan. 1, 1995).
Hahn, S., "Structure and mechanism of the RNA Polymerase II transcription machinery" Nat Struct Mol Biol 11(5):394-403 (May 1, 2004).
Hames, B., et al. Nucleic Acid Hybridisation: A Practical Approach Hames,B. and Higgins, S., eds., First edition, Oxford, UK:IRL Press,: 1-264 (Dec. 1, 1985).
Han, Y., et al., "Structural visualization of RNA polymerase III transcription machineries" Cell Discov 4(40):1-15 (Jul. 31, 2018).
Handa, H., et al., "Complementation of adeno-associated virus growth with temperature-sensitive mutants of human adenovirus types 12 and 5" J Gen Virol 29(2):239-242 (Nov. 1, 1975).
Hehir, K., et al., "Molecular characterization of replication-competent variants of adenovirus vectors and genome modifications to prevent their occurrence" J Virol 70(12):8459-8467 (Dec. 1, 1996).
Hermonat, P., et al., "Genetics of adeno-associated virus: isolation and preliminary characterization of adeno-associated virus type 2 mutants" J Virol 51(2):329-339 (Jul. 1, 1984).
Hermonat, P., et al., "Use of adeno-associated virus as a mammalian DNA cloning vector: transduction of neomycin resistance into mammalian tissue culture cells" PNAS 81(20):6466-6470 (Oct. 1, 1984).
Hoess, R., et al., "The role of the loxP spacer region in P1 site-specific recombination" Nucleic Acids Res 14(5):2287-2300 (Mar. 11, 1986).
Holscher, C., et al., "Cell lines inducibly expressing the adeno-associated virus (AAV) rep gene: requirements for productive replication of rep-negative AAV mutants" J Virol 68(11):7169-7177 (Nov. 1, 1994).
Holscher, C., et al., "High-level expression of adeno-associated virus (AAV) Rep78 or Rep68 protein is sufficient for infectious-particle formation by a rep-negative AAV mutant" J Virol 69(11):6880-6885 (Nov. 1, 1995).
Inao, T., et al., "Improved transgene integration into the Chinese hamster ovary cell genome using the Cre-loxP system" J Biosci Bioeng 120(1):99-106 (Jul. 1, 2015).
"International Preliminary Report on Patentability—PCT/EP2021/078269" (Report Issuance Date: Apr. 13, 2023; Chapter I), :pp. 1-9 (Apr. 27, 2023).
"International Search Report—PCT/E2021/078269" (w/Written Opinion), :pp. 1-18 (Jan. 20, 2022).
Ishibashi1, M., et al., "Temperature-sensitive conditional-lethal mutants of an avian adenovirus (CELO): I. Isolation and characterization" Virology 45(1):42-52 (Jul. 1, 1971).
Ito, M., et al., "Adeno-associated satellite virus growth supported by a temperature-sensitive mutant of human adenovirus" J Gen Virol 9(3):243-245 (Dec. 1, 1970).
Janik, J., et al., "Locations of adenovirus genes required for the replication of adenovirus-associated virus" PNAS 78(3):1925-1929 (Mar. 1, 1981).
Jay, F., et al., "Eukaryotic translational control: adeno-associated virus protein synthesis is affected by a mutation in the adenovirus DNA-binding protein" PNAS 78(5):2927-2931 (May 1, 1981).
Johann, S., et al., "GLVRI, a receptor for gibbon ape leukemia virus, is homologous to a phosphate permease of Neurospora crassa and is expressed at high levels in the brain and thymus" J Virol 66(3):1635-1640 (Mar. 1, 1992).
Johnston, K., et al., "HSV/AAV hybrid amplicon vectors extend transgene expression in human glioma cells" Hum Gene Ther 8(3):359-370 (Feb. 10, 1987).
Kallunki, T., et al., "How to Choose the Right Inducible Gene Expression System for Mammalian Studies?" Cells 8(8):796 (1-16) (Jul. 30, 2019).
Kawabe, Y., et al., "Repeated integration of antibody genes into a pre-selected chromosomal locus of CHO cells using an accumulative site-specific gene integration system" Cytotechnology 64(3):267-279 (May 1, 2012).
Khleif, S., et al., "Inhibition of Cellular transformation by the adeno-associated virus rep gene" Virology 181(2):738-741 (Apr. 1, 1991).
Kim, H., et al., "Mouse Cre-LoxP system: general principles to determine tissue-specific roles of target genes" Lab Anim Res 34(4):147-159 (Dec. 31, 2018).
Kondratov, O et al., "Direct Head-to-Head Evaluation of Recombinant Adeno-associated Viral Vectors Manufactured in Human versus Insect Cells" Mole Ther 25(12):2661-2675 (Dec. 6, 2017).
Kotin, R., et al., "Prospects for the Use of Adeno-Associated Virus as a Vector for Human Gene Therapy" Hum Gene Ther 5(7):793-801 (Jul. 1, 1994).
Labow, M., et al., "Adeno-associated virus gene expression inhibits cellular transformation by heterologous genes" Mol Cell Biol 7(4):1320-1325 (Apr. 1, 1987).
Langer, S., et al., "A genetic screen identifies novel non-compatible loxP sites" Nucleic Acids Res 30(14):3067-3077 (Jul. 15, 2002).
Lanza, A., et al., "Using the Cre/lox system for targeted integration into the human genome: loxFAS-loxP pairing and delayed introduction of Cre DNA improve gene swapping efficiency" Biotechnol J 7(7):898-908 (Jul. 1, 2012).
Laughlin, C., et al., "Effect of deletions in adenovirus early region 1 genes upon replication of adeno-associated virus" J Virol 41(3):868-876 (Mar. 1, 1982).

(56) References Cited

OTHER PUBLICATIONS

Laughlin, C., et al., "Spliced adenovirus-associated virus RNA" PNAS 76(11):5567-5571 (Nov. 1, 1979).
Lebkowski, J., et al., "Adeno-associated virus: a vector system for efficient introduction and integration of DNA into a variety of mammalian cell types" Mol Cell Biol 8(10):3988-3996 (Oct. 1, 1988).
Lee, G., et al., Role of nucleotide sequences of loxP spacer region in Cre-mediated recombination Gene(216 Suppl 1):55-65 (Aug. 17, 1998).
Lee, L., et al., "Sequence of the loxP Site Determines the Order of Strand Exchange by the Cre Recombinase" J Mole Biol 326(2):397-412 (Feb. 14, 2003).
Li, J., et al., "Role for highly regulated rep gene expression in adeno-associated virus vector production" J Virol 71(7):5236-5243 (Jul. 1, 1997).
Li, X., et al., "Evaluation of TorsinA as a target for Parkinson disease therapy in mouse models" PLOS One 7(11):e50063 (1-8) (Nov. 21, 2012).
Lochmueller, H., et al., "Emergence of Early Region 1-Containing Replication-Competent Adenovirus in Stocks of Replication-Defective Adenovirus Recombinants (ΔE1 + ΔE3) During Multiple Passages in 293 Cells" Hum Gene Ther 5(12):1485-1491 (Dec. 1, 1994).
Louis, N., et al., "Cloning and Sequencing of the Cellular-Viral Junctions from the Human Adenovirus Type 5 Transformed 293 Cell Line" Virology 233(2):423-429 (Jul. 1, 1997).
Ma, Y, et al., "Structure, function, and evolution of adenovirus-associated RNA: a phylogenetic approach" J Virol 70(8):5083-5099 (Aug. 1, 1996).
Machitani, M., et al., "Development of an adenovirus vector lacking the expression of virus-associated RNAs" J Control Release 154(3):285-289 (Sep. 25, 2011).
Machitani, M., et al., "Development of an adenovirus vector lacking the expression of virus-associated RNAs" J Control Rel 154(3 Suppl Appendix A):1-6 (Sep. 25, 2011).
Maekawa, A., et al., "Efficient production of adenovirus vector lacking genes of virus-associated RNAs that disturb cellular RNAi machinery" Sci Rep 3(1136):1-8 (Jan. 25, 2013).
Mannino, R., et al., "Liposome Mediated Gene Transfer" Biotechniques 6(7):682-690 (Jul. 1, 1988).
Matsushita, T., et al., "Adeno-associated virus vectors can be efficiently produced without helper virus" Gene Ther 5(7):938-945 (Jul. 10, 1998).
McCarty, D., et al., "Sequences required for coordinate induction of adeno-associated virus p19 and p40 promoters by Rep protein" J Virol 65(6):2936-2945 (Jun. 1, 1991).
Meinke, G., et al., "Cre Recombinase and Other Tyrosine Recombinases" ACS Chem Reviews 116(20):12785-12820 (May 10, 2016).
Mendelson, E., et al., "Expression and rescue of a non-selected marker from an integrated AAV vector" Virology 166(1):154-165 (Sep. 1, 1988).
Mietzsch, M., et al., "OneBac 2.0: Sf9 Cell Lines for Production of AAV1, AAV2, and AAV8 Vectors with Minimal Encapsidation of Foreign DNA" Hum Gene Ther Methods 28(1):15-22 (Feb. 1, 2017).
Mietzsch, M., et al., "OneBac: Platform for Scalable and High-Titer Production of Adeno-Associated Virus Serotype 1-12 Vectors for Gene Therapy" Hum Gene Ther 25(3):212-222 (Mar. 1, 2014).
Miller, A., et al., "Construction and properties of retrovirus packaging cells based on gibbon ape leukemia virus" J Virol 65(5):2220-2224 (May 1, 1991).
Missirlis, P., et al., "A high-throughput screen identifying sequence and promiscuity characteristics of the loxP spacer region in Cre-mediated recombination" BMC Genomics 7(73):1-13 (Apr. 4, 2006).
Muzyczka, N., et al. Viral Expression Vectors : Current Topics in Microbiology and Immunology "Chapter 5: Use of Adeno-Associated Virus as a General Transduction Vector for Mammalian Cells" Muzyczka, N. ed., First edition, Heidelberg, Germany: Springer-Verlag Berlin, vol. 158:97-129 (Jan. 1, 1992).
Muzyczka, N., et al., "Adeno-associated virus (AAV) vectors: will they work?" J Clin Invest 94(4):1351-1351 (Oct. 1, 1994).
Myers, M., et al., "Adeno-associated virus replication: The effect of L-canavanine or a helper virus mutation on accumulation of viral capsids and progeny single-stranded DNA" J Biol Chem 256(2):567-570 (Jan. 25, 1981).
Myers, M., et al., "Adenovirus helper function for growth of adeno-associated virus: effect of temperature-sensitive mutations in adenovirus early gene region 2" J Virol 35(1):65-75 (Jul. 1, 1980).
Nakamura, S., et al., "Development of packaging cell lines for generation of adeno-associated virus vectors by lentiviral gene transfer of trans-complementary components" Eur J Haematol 73(4):285-294 (Oct. 1, 2004).
Nakano, M., et al., "Production of viral vectors using recombinase-mediated cassette exchange" Nucleic Acids Res 33(8):e76 (1-8) (May 5, 2005).
Niesner, B., et al., "Using the cre-lox system to randomize target gene expression states and generate diverse phenotypes" Biotechnol Bioeng 110(10):2677-2686 (Jun. 3, 2013).
Nikitina, T., et al., "RNA polymerase III transcription machinery: Structure and transcription regulation" Mole Biol 39(2):161-172 (Mar. 1, 2005).
Oler, A., et al., "Human RNA polymerase III transcriptomes and relationships to Pol II promoter chromatin and enhancer-binding factors" Nat Struct Mole Biol 17(5):620-628 (May 1, 2010).
Ostrove, J., et al., "Adenovirus early region 1b gene function required for rescue of latent adeno-associated virus" Virology 104(2):502-505 (Jul. 30, 1980).
Paul, W., Fundamental Immunology "Chapter 9: Structure and Function of Immunoglobins" Paul, W., ed., Third edition, New York, N.Y.—USA: Raven Press,: 242, 292-295 (Jan. 1, 1993).
Pebernard, S., et al., "Determinants of interferon-stimulated gene induction by RNAi vectors" Differentiation 72(2-3):103-111 (Mar. 1, 2004).
Pei, Z., et al., "Adenovirus vectors lacking virus-associated RNA expression enhance shRNA activity to suppress hepatitis C virus replicatio" Sci Rep 3(3575):1-6 (Dec. 20, 2013).
Qiao, C., et al., "A novel gene expression control system and its use in stable, high-titer 293 cell-based adeno-associated virus packaging cell lines" J Virol 76(24):13015-13027 (Dec. 1, 2002).
Qiao, C., et al., "Feasibility of generating adeno-associated virus packaging cell lines containing inducible adenovirus helper genes" J Virol 76(4):1904-1913 (Feb. 15, 2002).
Revyakin, A., et al., "Transcription initiation by human RNA polymerase II visualized at single-molecule resolution" Gene Dev 26(15):1691-1702 (Aug. 1, 2012).
Robert, M., et al., "Manufacturing of recombinant adeno-associated viruses using mammalian expression platforms" Biotechnnol J 12(3):1600193 (1-18) (Mar. 1, 2017).
Salvetti, A., et al., "Factors influencing recombinant adeno-associated virus production" Hum Gene Ther 9(5):695-706 (Mar. 20, 1998).
Sambrook, J., et al. Molecular Cloning: A Laboratory Manual Second edition, New York: Cold Spring Harbor Laboratory Press, (Jan. 1, 1989).
Samulski, J., et al., "AAV-Mediated Gene Therapy for Research and Therapeutic Purposes" Annu Rev Virol 1(1):427-451 (Nov. 1, 2014).
Samulski, R., et al., "Adeno-associated virus: integration at a specific chromosomal locus" Curr Opin Genet Dev 3(1):74-80 (Feb. 1, 1993).
Samulski, R., et al., "Helper-free stocks of recombinant adeno-associated viruses: normal integration does not require viral gene expression" J Virol 63(9):3822-3828 (Sep. 1, 1989).
Saraf-Levy, T., et al., "Site-specific recombination of asymmetric lox sites mediated by a heterotetrameric Cre recombinase complex" Bioorg Med Chem 14(9):3081-3089 (May 1, 2006).
Scammell, E., et al., "Focal Deletion of the Adenosine Al Receptor in Adult Mice Using an Adeno-Associated Viral Vector" J Neurosci 23(13):5762-5770 (Jul. 2, 2003).

(56) References Cited

OTHER PUBLICATIONS

Schucht, R., et al., "A new generation of retroviral producer cells: predictable and stable virus production by Flp-mediated site-specific integration of retroviral vectors" Mol Ther 14(2):285-292 (Aug. 1, 2006).
Sheren, J., et al., "A randomized library approach to identifying functional lox site domains for the Cre recombinase" Nucleic Acids Res 35(16):5464-5473 (Aug. 15, 2007).
Siegel, R., et al., "Recombinatorial cloning using heterologous lox sites" Genome Res 14(6):1119-11129 (Jun. 1, 2004).
Siegel, R., et al., "Using an in vivo phagemid system to identify non-compatible loxP sequences" FEBS Lett 499(1-2):147-153 (Jun. 15, 2001).
Siegel, R., et al., "Using an in vivo phagemid system to identify non-compatible loxP sequences" FEBS Lett 505(3):467-473 (Sep. 21, 2001).
Silver, D., et al., "Self-Excising Retroviral Vectors Encoding the Cre Recombinase Overcome Cre-Mediated Cellular Toxicity" Mole Cell 8(1):233-243 (Jul. 1, 2001).
Snouwaert, J., et al., "Large numbers of random point and cluster mutations within the adenovirus VA I gene allow characterization of sequences required for efficient transcription" Nucleic Acids Res 15(20):8293-8303 (Oct. 26, 1987).
Sommer, J., et al., "Quantification of adeno-associated virus particles and empty capsids by optical density measurement" Mole Ther 7(1):122-128 (Jan. 1, 2003).
Sommerfelt, M., et al., "Receptor interference groups of 20 retroviruses plating on human cells" Virology 176(1):58-59 (May 1, 1990).
Song, J., et al., "Poly(U) and polyadenylation termination signals are interchangeable for terminating the expression of shRNA from a pol II promoter" Biochem Biophys Res Comm 323(2):573-578 (Oct. 15, 2004).
Srivastava, A., et al., "Nucleotide sequence and organization of the adeno-associated virus 2 genome" J Virol 45(2):555-564 (Feb. 1, 1983).
Straus, S., et al., "DNA-Minus Temperature-Sensitive Mutants of Adenovirus Type 5 Help Adenovirus-Associated Virus Replication" J Virol 17(1):140-148 (Jan. 1, 1976).
Takata, Y., et al., "Comparison of efficiency between FLPe and Cre for recombinase-mediated cassette exchange in vitro and in adenovirus vector production" Genes To Cells 16(7):765-777 (Jul. 1, 2011).
Tamayose, K., et al., "A new strategy for large-scale preparation of high-titer recombinant adeno-associated virus vectors by using packaging cell lines and sulfonated cellulose column chromatography" Hum Gene Ther 7(4):507-513 (Mar. 1, 1996).
Thomas, K., et al., "Site-directed mutagenesis by gene targeting in mouse embryo-derived stem cells" Cell 51(3):503-512 (Nov. 6, 1987).
Thompson, S., et al., "Germ Line Transmission and Expression of a Corrected HPRT Gene Produced by Gene Targeting in Embryonic Stem Cells" Cell 56(2):313-321 (Jan. 27, 1989).
Thomson, J., et al., "Mutational analysis of loxP sites for efficient Cre-mediated insertion into genomic DNA" Genesis 36(3):162-167 (Jul. 1, 2003).
Thrasher, A., et al., "Generation of recombinant adeno-associated virus (rAAV) from an adenoviral vector and functional reconstitution of the NADPH-oxidase" Gene Ther 2(7):481-485 (Sep. 1, 1995).
Tratschin, J., et al., "A human parvovirus, adeno-associated virus, as a eucaryotic vector: transient expression and encapsidation of the procaryotic gene for chloramphenicol acetyltransferase" Mol Cell Biol 4(10):2072-2081 (Oct. 1, 1984).
Tratschin, J., et al., "Adeno-associated virus vector for high-frequency integration, expression, and rescue of genes in mammalian cells" Mol Cell Biol 5(11):3251-3260 (Nov. 1, 1985).
Tratschin, J., et al., "Negative and positive regulation in trans of gene expression from adeno-associated virus vectors in mammalian cells by a viral rep gene product" Mole Cell Biol 6(8):2884-2894 (Aug. 1, 1986).
"Tratschin, J.," Genetic analysis of adeno-associated virus: properties of deletion mutants constructed in vitro and evidence for an adeno-associated virus replication function J Virol(51 Suppl 3):611-619 (Sep. 1, 1984).
Turan, S., et al., "Recombinase-mediated cassette exchange (RMCE): traditional concepts and current challenges" J Mol Biol 407(2): 193-221 (Mar. 25, 2011).
Vachon, V., et al., "Adenovirus VA RNA: An essential pro-viral non-coding RNA" Virus Res 212:39-52 (Jan. 2, 2016).
Van Duyne, G., et al., "A structural view of cre-loxp site-specific recombination" Annu Rev Biophys Biomol Struct 30:87-104 (Jun. 1, 2001).
Van Duyne, G.,, "Cre Recombinase" Microbio Spectr 3(1):1-19 (Feb. 1, 2015).
Ventura, A., et al., "Cre-lox-regulated conditional RNA interference from transgenes" PNAS 101(28):10380-10385 (Jul. 13, 2004).
Watson, J., et al. Recombinant DNA : A Short Course First edition, New York: Scientific American Books (W.H. Freeman & Company),:1-260 (Jan. 1, 1983).
Weitzman, M., et al. Adeno-Associated Virus—Methods in Molecular Biology "Chapter 1: Adeno-Associated Virus Biology" Snyder, R. & Moullier, P. eds, First edition, Totowa, New Jersey—US: Humana Press—Springer Science + Business Media, LLC, vol. 807:1-23 (Sep. 27, 2011).
West, M, et al., "Gene expression in adeno-associated virus vectors: The effects of chimeric mRNA structure, helper virus, and adenovirus VA, RNA" Virology 160(1):38-47 (Sep. 1, 1987).
Wilson, C., et al., "Formation of infectious hybrid virions with gibbon ape leukemia virus and human T-cell leukemia virus retroviral envelope glycoproteins and the gag and pol proteins of Moloney murine leukemia virus" J Virol 63(5):2374-2378 (May 1, 1989).
Winnacker, E., From Genes to Clones: Introduction to Gene Technology Weller, D., ed., First edition, Weinnheim, Germany: Springer-VCH,:v-vii (Jan. 1, 1987).
Wobus, C., et al., "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection" J Virol 74(19):9281-9293 (Oct. 1, 2000).
Wong, E., et al., "Reproducible doxycycline-inducible transgene expression at specific loci generated by Cre-recombinase mediated cassette exchange" Nucleic Acids Res 33(17):e147 (1-13) (Oct. 4, 2005).
Xiao, X., et al., "Production of High-Titer Recombinant Adeno-Associated Virus Vectors in the Absence of Helper Adenovirus" J Virol 72(3):2224-2232 (Mar. 1, 1998).
Yang, Y., et al., "Inducible, high-level production of infectious murine leukemia retroviral vector particles pseudotyped with vesicular stomatitis virus G envelope protein" Hum Gene Ther 6(9):1203-1213 (Sep. 1, 1995).
Yuan, Z., et al., "A versatile adeno-associated virus vector producer cell line method for scalable vector production of different serotypes" Hum Gene Ther 22(5):613-624 (May 1, 2011).
Zhang, X., et al., "High-titer recombinant adeno-associated virus production from replicating amplicons and herpes vectors deleted for glycoprotein H" Hum Gene Ther 10(15):2527-2537 (Oct. 10, 1999).
Zhen, Z., et al., "Infectious Titer Assay for Adeno-Associated Virus Vectors with Sensitivity Sufficient to Detect Single Infectious Events" Hum Gene Ther 15(7):709-715 (Jul. 1, 2004).
Zijlstra, M., et al., "Germ-line transmission of a disrupted β2microglobulin gene produced by homologous recombination in embryonic stem cells" Nature 342(6248):435-438 (Nov. 1, 1989).
"International Preliminary Report on Patentability—PCT/EP2021/078268" (Report Issuance Date: Apr. 13, 2023; Chapter I),:pp. 1-9 (Apr. 27, 2023).
International Search Report and Written Opinion for PCT/EP2021/078268 mailed Jan. 21, 2022; pp. 16.
Mizukami, H., et al., "Separate Control of Rep and Cap Expression Using Mutant and Wild-Type LoxP Sequences and Improved Packaging System for Adeno-Associated Virus Vector Production" Mol Biotechnol 27(1):7-14 (May 1, 2004).

(56) References Cited

OTHER PUBLICATIONS

Mlynarova, L., et al., "The promiscuity of heterospecific lox sites increases dramatically in the presence of palindromic DNA" Gene 296( Suppl 1-2):129-137 (Aug. 21, 2002).
Ojala, D.S., et al., "In Vivo Selection of a Computationally Designed Schema AAV Library Yields a Novel Variant for Infection of Adult Neural Stem Cells in the SVZ" Mol Ther 26(1):304-319 (Jan. 3, 2018).
Xie, M. et al., "Mammalian designer cells: Engineering principles and biomedical applications" Biotechnol. J. 10(7):1005-1018 (May 26, 2015).

* cited by examiner

SEQUENCE LISTING

```
<160> NUMBER OF SEQ ID NOS: 45

<210> SEQ ID NO 1
<211> LENGTH: 13
<212> TYPE: DNA
<213> ORGANISM: Bacteriophage P1

<400> SEQUENCE: 1

ataacttcgt ata                                                            13


<210> SEQ ID NO 2
<211> LENGTH: 13
<212> TYPE: DNA
<213> ORGANISM: Bacteriophage P1

<400> SEQUENCE: 2

tatacgaagt tat                                                            13


<210> SEQ ID NO 3
<211> LENGTH: 8
<212> TYPE: DNA
<213> ORGANISM: Bacteriophage P1

<400> SEQUENCE: 3

atgtatgc                                                                   8


<210> SEQ ID NO 4
<211> LENGTH: 8
<212> TYPE: DNA
<213> ORGANISM: Artificial Sequence
<220> FEATURE:
<223> OTHER INFORMATION: L3 spacer sequence

<400> SEQUENCE: 4

aagtctcc                                                                   8


<210> SEQ ID NO 5
<211> LENGTH: 8
<212> TYPE: DNA
<213> ORGANISM: Artificial Sequence
<220> FEATURE:
<223> OTHER INFORMATION: L2 inverted spacer sequence

<400> SEQUENCE: 5

gcatacat                                                                   8


<210> SEQ ID NO 6
<211> LENGTH: 8
<212> TYPE: DNA
<213> ORGANISM: Artificial Sequence
<220> FEATURE:
<223> OTHER INFORMATION: LoxFas spacer sequence
```

<400> SEQUENCE: 6 tacctttc 8

<210> SEQ ID NO 7
<211> LENGTH: 8
<212> TYPE: DNA
<213> ORGANISM: Artificial Sequence
<220> FEATURE:
<223> OTHER INFORMATION: Lox511 spacer sequence

<400> SEQUENCE: 7 atgtatac 8

<210> SEQ ID NO 8
<211> LENGTH: 8
<212> TYPE: DNA
<213> ORGANISM: Artificial Sequence
<220> FEATURE:
<223> OTHER INFORMATION: Lox5171 spacer sequence

<400> SEQUENCE: 8 atgtgtac 8

<210> SEQ ID NO 9
<211> LENGTH: 8
<212> TYPE: DNA
<213> ORGANISM: Artificial Sequence
<220> FEATURE:
<223> OTHER INFORMATION: Lox2272 spacer sequence

<400> SEQUENCE: 9 aagtatcc 8

<210> SEQ ID NO 10
<211> LENGTH: 8
<212> TYPE: DNA
<213> ORGANISM: Artificial Sequence
<220> FEATURE:
<223> OTHER INFORMATION: Loxm2 spacer sequence

<400> SEQUENCE: 10 agaaacca 8

<210> SEQ ID NO 11
<211> LENGTH: 8
<212> TYPE: DNA
<213> ORGANISM: Artificial Sequence
<220> FEATURE:
<223> OTHER INFORMATION: Loxm3 spacer sequence

<400> SEQUENCE: 11 taatacca 8

<210> SEQ ID NO 12
<211> LENGTH: 8
<212> TYPE: DNA
<213> ORGANISM: Artificial Sequence
<220> FEATURE:
<223> OTHER INFORMATION: Loxm7 spacer sequence

<400> SEQUENCE: 12 agatagaa 8

<210> SEQ ID NO 13

<211> LENGTH: 608
<212> TYPE: DNA
<213> ORGANISM: Human cytomegalovirus

<400> SEQUENCE: 13
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattagc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctccg tttagtgaac 600
gtcagatc 608

<210> SEQ ID NO 14
<211> LENGTH: 696
<212> TYPE: DNA
<213> ORGANISM: Human cytomegalovirus

<400> SEQUENCE: 14
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattagc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctccg tttagtgaac 600
gtcagatcta gctctgggag aggagcccag cactagaagt cggcggtgtt tccattcggt 660
gatcagcact gaacacagag gaagcttgcc gccacc 696

<210> SEQ ID NO 15
<211> LENGTH: 2125
<212> TYPE: DNA
<213> ORGANISM: Human cytomegalovirus

<400> SEQUENCE: 15
ctgcagtgaa taataaaatg tgtgtttgtc cgaaatacgc gttttgagat ttctgtcgcc 60
gactaaattc atgtcgcgcg atagtggtgt ttatcgccga tagagatggc gatattggaa 120
aaatcgatat ttgaaaatat ggcatattga aaatgtcgcc gatgtgagtt tctgtgtaac 180
tgatatcgcc atttttccaa aagtgatttt tgggcatacg cgatatctgg cgatagcgct 240
tatatcgttt acgggggatg gcgatagacg actttggtga cttgggcgat tctgtgtgtc 300
gcaaatatcg cagtttcgat ataggtgaca gacgatatga ggctatatcg ccgatagagg 360

```
cgacatcaag ctggcacatg gccaatgcat atcgatctat acattgaatc aatattggcc    420
attagccata ttattcattg gttatatagc ataaatcaat attggctatt ggccattgca    480
tacgttgtat ccatatcata atatgtacat ttatattggc tcatgtccaa cattaccgcc    540
atgttgacat tgattattga ctagttatta atagtaatca attacggggt cattagttca    600
tagcccatat atggagttcc gcgttacata acttacggta aatggcccgc ctggctgacc    660
gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtacgcc ccctattgac gtcaatgacg gtaaatggcc    840
cgcctggcat tatgcccagt acatgacctt atgggacttt cctacttggc agtacatcta    900
cgtattagtc atcgctatta ccatggtgat gcggttttgg cagtacatca atgggcgtgg    960
atagcggttt gactcacggg gatttccaag tctccacccc attgacgtca atgggagttt   1020
gttttggcac caaaatcaac gggactttcc aaaatgtcgt aacaactccg ccccattgac   1080
gcaaatgggc ggtaggcgtg tacggtggga ggtctatata agcagagctc gtttagtgaa   1140
ccgtcagatc gcctggagac gccatccacg ctgttttgac ctccatagaa gacaccggga   1200
ccgatccagc ctccgcggcc gggaacggtg cattggaacg cggattcccc gtgccaagag   1260
tgacgtaagt accgcctata gagtctatag gcccaccccc ttggcttctt atgcatgcta   1320
tactgttttt ggcttggggt ctatacaccc ccgcttcctc atgttatagg tgatggtata   1380
gcttagccta taggtgtggg ttattgacca ttattgacca ctcccctatt ggtgacgata   1440
ctttccatta ctaatccata acatggctct ttgccacaac tctctttatt ggctatatgc   1500
caatacactg tccttcagag actgacacgg actctgtatt tttacaggat ggggtctcat   1560
ttattattta caaattcaca tatacaacac caccgtcccc agtgcccgca gtttttatta   1620
aacataacgt gggatctcca cgcgaatctc gggtacgtgt tccggacatg ggctcttctc   1680
cggtagcggc ggagcttcta catccgagcc ctgctcccat gcctccagcg actcatggtc   1740
gctcggcagc tccttgctcc taacagtgga ggccagactt aggcacagca cgatgcccac   1800
caccaccagt gtgccgcaca aggccgtggc ggtagggtat gtgtctgaaa atgagctcgg   1860
ggagcgggct tgcaccgctg acgcatttgg aagacttaag gcagcggcag aagaagatgc   1920
aggcagctga gttgttgtgt tctgataaga gtcagaggta actcccgttg cggtgctgtt   1980
aacggtggag ggcagtgtag tctgagcagt actcgttgct gccgcgcgcg ccaccagaca   2040
taatagctga cagactaaca gactgttcct ttccatgggt cttttctgca gtcaccgtcc   2100
ttgacacggt ttaaacgccg ccacc                                         2125
```

<210> SEQ ID NO 16
<211> LENGTH: 218
<212> TYPE: DNA
<213> ORGANISM: Bos taurus

<400> SEQUENCE: 16

```
ttctagttgc cagccatctg ttgtttgccc ctcccccgtg ccttccttga ccctggaagg     60
tgccactccc actgtccttt cctaataaaa tgaggaaatt gcatcgcatt gtctgagtag    120
gtgtcattct attctggggg gtggggtggg gcaggacagc aagggggagg attgggaaga    180
caatagcagg catgctgggg atgcggtggg ctctatgg                            218
```

<210> SEQ ID NO 17

<211> LENGTH: 73
<212> TYPE: DNA
<213> ORGANISM: Homo sapiens

<400> SEQUENCE: 17
caggataata tatggtaggg ttcatagcca gagtaacctt ttttttaat ttttatttta 60 ttttattttt gag 73

<210> SEQ ID NO 18
<211> LENGTH: 288
<212> TYPE: DNA
<213> ORGANISM: Simian virus 40

<400> SEQUENCE: 18
agtcagcaac caggtgtgga aagtccccag gctccccagc aggcagaagt atgcaaagca 60
tgcatctcaa ttagtcagca accatagtcc cgcccctaac tccgcccatc ccgcccctaa 120
ctccgcccag ttccgcccat tctccgcccc atggctgact aattttttt atttatgcag 180 aggccgaggc cgcctctgcc tctgagctat tccagaagta gtgaggaggc ttttttggag 240
gcctaggctt ttgcaaaaag ctcccgggag cttgtatatc cattttcg 288

<210> SEQ ID NO 19
<211> LENGTH: 129
<212> TYPE: DNA
<213> ORGANISM: Simian virus 40

<400> SEQUENCE: 19
aacttgttta ttgcagctta taatggttac aaataaagca atagcatcac aaatttcaca 60
aataaagcat ttttttcacc attctagttg tggtttgtcc aaactcatca atgtatctta 120
tcatgtctg 129

<210> SEQ ID NO 20
<211> LENGTH: 34
<212> TYPE: DNA
<213> ORGANISM: Saccharomyces cerevisiae

<400> SEQUENCE: 20
gaagttccta ttctctagaa agtataggaa cttc 34

<210> SEQ ID NO 21
<211> LENGTH: 13
<212> TYPE: DNA
<213> ORGANISM: Saccharomyces cerevisiae

<400> SEQUENCE: 21
gaagttccta ttc 13

<210> SEQ ID NO 22
<211> LENGTH: 13
<212> TYPE: DNA
<213> ORGANISM: Saccharomyces cerevisiae

<400> SEQUENCE: 22
gaataggaac ttc 13

<210> SEQ ID NO 23
<211> LENGTH: 8
<212> TYPE: DNA
<213> ORGANISM: Saccharomyces cerevisiae

<400> SEQUENCE: 23 tctagaaa 8

<210> SEQ ID NO 24
<211> LENGTH: 8
<212> TYPE: DNA
<213> ORGANISM: Artificial Sequence
<220> FEATURE:
<223> OTHER INFORMATION: F3 site spacer sequence

<400> SEQUENCE: 24 ttcaaata 8

<210> SEQ ID NO 25
<211> LENGTH: 8
<212> TYPE: DNA
<213> ORGANISM: Artificial Sequence
<220> FEATURE:
<223> OTHER INFORMATION: F5 site spacer sequence

<400> SEQUENCE: 25 ttcaaaag 8

<210> SEQ ID NO 26
<211> LENGTH: 343
<212> TYPE: PRT
<213> ORGANISM: Bacteriophage P1

<400> SEQUENCE: 26

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240
```

```
Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340


<210> SEQ ID NO 27
<211> LENGTH: 1029
<212> TYPE: RNA
<213> ORGANISM: Bacteriophage P1

<400> SEQUENCE: 27

augagcaacc ugcugaccgu gcaccagaac cugcccgccc ugcccgugga cgccaccagc     60

gacgagguga ggaagaaccu gauggacaug uucagggaca ggcaggccuu cagcgagcac    120

accuggaaga ugcugcugag cgugugcagg agcugggccg ccuggugcaa gcugaacaac    180

aggaaguggu uccccgccga gcccgaggac gugagggacu accugcugua ccugcaggcc    240

aggggccugg ccgugaagac cauccagcag caccugggcc agcugaacau gcugcacagg    300

aggagcggcc ugcccaggcc cagcgacagc aacgccguga gccuggugau gaggaggauc    360

aggaaggaga acguggacgc cggcgagagg gccaagcagg cccuggccuu cgagaggacc    420

gacuucgacc aggugaggag ccugauggag aacagcgaca ggugccagga caucaggaac    480

cuggccuucc ugggcaucgc cuacaacacc cugcugagga ucgccgagau cgccaggauc    540

agggugaagg acaucagcag gaccgacggc ggcaggaugc ugauccacau cggcaggacc    600

aagacccugg ugagcaccgc cggcguggag aaggcccuga gccugggcgu gaccaagcug    660

guggagaggu ggaucagcgu gagcggcgug gccgacgacc ccaacaacua ccuguucugc    720

agggugagga agaacggcgu ggccgccccc agcgccacca gccagcugag caccagggcc    780

cuggagggca ucuucgaggc cacccacagg cugaucuacg gcgccaagga cgacagcggc    840

cagagguacc uggccuggag cggccacagc gccagggugg gcgccgccag ggacauggcc    900

agggccggcg ugagcauccc cgagaucaug caggccggcg gcuggaccaa cgugaacauc    960

gugaugaacu acaucaggaa ccuggacagc gagaccggcg ccauggugag gcugcuggag   1020

gacggcgac                                                           1029


<210> SEQ ID NO 28
<211> LENGTH: 798
<212> TYPE: DNA
<213> ORGANISM: Artificial Sequence
<220> FEATURE:
<223> OTHER INFORMATION: green fluorescent protein encoding nucleic acid

<400> SEQUENCE: 28

atggtgagca agggcgagga gctgttcacc ggggtggtgc ccatcctggt cgagctggac     60

ggcgacgtaa acggccacaa gttcagcgtg tccggcgagg gcgagggcga tgccacctac    120
```

```
ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtcc    720

ggactcagat ctcgagctca agcttcgaat tctgcagtcg acggtaccgc gggcccggga    780

tccaccggat ctagatga                                                  798
```

```
<210> SEQ ID NO 29
<211> LENGTH: 4
<212> TYPE: RNA
<213> ORGANISM: Human adenovirus type 2

<400> SEQUENCE: 29

ccgg                                                                   4


<210> SEQ ID NO 30
<211> LENGTH: 5
<212> TYPE: RNA
<213> ORGANISM: Human adenovirus type 2

<400> SEQUENCE: 30

yccgg                                                                  5


<210> SEQ ID NO 31
<211> LENGTH: 10
<212> TYPE: RNA
<213> ORGANISM: Artificial Sequence
<220> FEATURE:
<223> OTHER INFORMATION: VA RNA A-box consensus sequence
<220> FEATURE:
<221> NAME/KEY: misc_feature
<222> LOCATION: (4)..(5)
<223> OTHER INFORMATION: n is a, c, g, or u

<400> SEQUENCE: 31

rrynnarygg                                                            10


<210> SEQ ID NO 32
<211> LENGTH: 9
<212> TYPE: RNA
<213> ORGANISM: Artificial Sequence
<220> FEATURE:
<223> OTHER INFORMATION: VA RNA B-box consensus sequence
<220> FEATURE:
<221> NAME/KEY: misc_feature
<222> LOCATION: (7)..(8)
<223> OTHER INFORMATION: n is a, c, g, or u

<400> SEQUENCE: 32

gwucrannc                                                              9


<210> SEQ ID NO 33
```

<211> LENGTH: 225
<212> TYPE: DNA
<213> ORGANISM: Human adenovirus type 2

<400> SEQUENCE: 33
cgtgcaaaag gagagcctgt aagcgggcac tcttccgtgg tctggtggat aaattcgcaa 60
gggtatcatg gcggacgacc ggggttcgaa ccccggatcc ggccgtccgc cgtgatccat 120
gcggttaccg cccgcgtgtc gaacccaggt gtgcgacgtc agacaacggg ggagcgctcc 180
ttttggcttc cttccaggcg cggcggctgc tgcgctagct ttttt 225

<210> SEQ ID NO 34
<211> LENGTH: 225
<212> TYPE: DNA
<213> ORGANISM: Human adenovirus type 2

<400> SEQUENCE: 34
cgtgcaaaag gagagcctgt aagcgggcac tcttccgtgg tctggtggat aaattcgcaa 60
gggtatcatg gcggacgacc gttgttcgaa caccggatcc ggccgtccgc cgtgatccat 120
gcggttaccg cccgcgtgtc gaacccaggt gtgcgacgtc agacaacggg ggagcgctcc 180
ttttggcttc cttccaggcg cggcggctgc tgcgctagct ttttt 225

<210> SEQ ID NO 35
<211> LENGTH: 242
<212> TYPE: DNA
<213> ORGANISM: Human adenovirus type 5

<400> SEQUENCE: 35
tcgttgacgc tctagaccgt gcaaaaggag agcctgtaag cgggcactct tccgtggtct 60
ggtggataaa ttcgcaaggg tatcatggcg gacgaccggg gttcgagccc cgtatccggc 120
cgtccgccgt gatccatgcg gttaccgccc gcgtgtcgaa cccaggtgtg cgacgtcaga 180 caacgggga gtgctccttt tggcttcctt ccaggcgcgg cggctgctgc gctagctttt 240
tt 242

<210> SEQ ID NO 36
<211> LENGTH: 466
<212> TYPE: DNA
<213> ORGANISM: Human adenovirus type 5

<400> SEQUENCE: 36
tcgttgacgc tctagaccgt gcaaaaggag agcctgtaag cgggcactct tccgtggtct 60
ggtggataaa ttcgcaaggg tatcatggcg gacgaccggg gttcgagccc cgtatccggc 120
cgtccgccgt gatccatgcg gttaccgccc gcgtgtcgaa cccaggtgtg cgacgtcaga 180 caacgggga gtgctccttt tggcttcctt ccaggcgcgg cggctgctgc gctagctttt 240
ttggccactg gccgcgcgca gcgtaagcgg ttaggctgga aagcgaaagc attaagtggc 300
tcgctccctg tagccggagg gttattttcc aagggttgag tcgcgggacc cccggttcga 360
gtctcggacc ggccggactg cggcgaacgg gggtttgcct ccccgtcatg caagaccccg 420
cttgcaaatt cctccggaaa cagggacgag cccctttttt gctttt 466

<210> SEQ ID NO 37
<211> LENGTH: 201
<212> TYPE: DNA
<213> ORGANISM: adeno-associated virus 2

<400> SEQUENCE: 37
gggcactctt ccgtggtctg gtggataaat tcgcaagggt atcatggcgg acgaccgggg 60
ttcgaacccc ggatccggcc gtccgccgtg atccatgcgg ttaccgcccg cgtgtcgaac 120
ccaggtgtgc gacgtcagac aacgggggag cgctcctttt ggcttccttc caggcgcggc 180
ggctgctgcg ctagcttttt t 201

<210> SEQ ID NO 38
<211> LENGTH: 201
<212> TYPE: DNA
<213> ORGANISM: adeno-associated virus 2

<400> SEQUENCE: 38
gggcactctt ccgtggtctg gtggataaat tcgcaagggt atcatggcgg acgaccgttg 60
ttcgaacacc ggatccggcc gtccgccgtg atccatgcgg ttaccgcccg cgtgtcgaac 120
ccaggtgtgc gacgtcagac aacgggggag cgctcctttt ggcttccttc caggcgcggc 180
ggctgctgcg ctagcttttt t 201

<210> SEQ ID NO 39
<211> LENGTH: 465
<212> TYPE: DNA
<213> ORGANISM: Artificial Sequence
<220> FEATURE:
<223> OTHER INFORMATION: stuffer sequence

<400> SEQUENCE: 39
aaggtcgggc aggaagaggg cctatttccc atgattcctt catatttgca tatacgatac 60
aaggctgtta gagagataat tagaattaat ttgactgtaa acacaaagat attagtacaa 120
aatacgtgac gtagaaagta ataatttctt gggtagtttg cagttttaaa attatgtttt 180
aaaatggact atcatatgct taccgtaact tgaaagtatt tcgatttctt ggctttatat 240
atcttgtgga aaggacgaaa caccgggcac tcttccgtgg tctggtggat aaattcgcaa 300
gggtatcatg gcggacgacc ggggttcgaa ccccggatcc ggccgtccgc cgtgatccat 360
gcggttaccg cccgcgtgtc gaacccaggt gtgcgacgtc agacaacggg ggagcgctcc 420
ttttggcttc cttccaggcg cggcggctgc tgcgctagct ttttt 465

<210> SEQ ID NO 40
<211> LENGTH: 738
<212> TYPE: PRT
<213> ORGANISM: Artificial Sequence
<220> FEATURE:
<223> OTHER INFORMATION: VP1 Capsid

<400> SEQUENCE: 40

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asn Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
```

```
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 41
<211> LENGTH: 736
<212> TYPE: PRT
<213> ORGANISM: Artificial Sequence
<220> FEATURE:
<223> OTHER INFORMATION: VP1 Capsid

<400> SEQUENCE: 41

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

-continued

```
Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560
```

```
Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735
```

<210> SEQ ID NO 42
<211> LENGTH: 264
<212> TYPE: DNA
<213> ORGANISM: Homo sapiens

<400> SEQUENCE: 42

```
aaggtcgggc aggaagaggg cctatttccc atgattcctt catatttgca tatacgatac     60

aaggctgtta gagagataat tagaattaat ttgactgtaa acacaaagat attagtacaa    120

aatacgtgac gtagaaagta ataatttctt gggtagtttg cagttttaaa attatgtttt    180

aaaatggact atcatatgct taccgtaact tgaaagtatt tcgatttctt ggctttatat    240

atcttgtgga aaggacgaaa cacc                                           264
```

<210> SEQ ID NO 43
<211> LENGTH: 313
<212> TYPE: DNA
<213> ORGANISM: Mus musculus

<400> SEQUENCE: 43

```
atccgacgcc gccatctcta ggcccgcgcc ggccccctcg cacagacttg tgggagaagc     60

tcggctactc ccctgccccg gttaatttgc atataatatt tcctagtaac tatagaggct    120

taatgtgcga taaaagacag ataatctgtt ctttttaata ctagctacat tttacatgat    180

aggcttggat ttctataaga gatacaaata ctaaattatt attttaaaaa acagcacaaa    240

aggaaactca ccctaactgt aaagtaattg tgtgttttga gactataaat atcccttgga    300

gaaaagcctt gtt                                                       313
```

<210> SEQ ID NO 44
<211> LENGTH: 215
<212> TYPE: DNA
<213> ORGANISM: Homo sapiens

<400> SEQUENCE: 44

-continued

```
gaacgctgac gtcatcaacc cgctccaagg aatcgcgggc ccagtgtcac taggcgggaa     60

cacccagcgc gcgtgcgccc tggcaggaag atggctgtga gggacagggg agtggcgccc    120

tgcaatattt gcatgtcgct atgtgttctg ggaaatcacc ataaacgtga aatgtctttg    180

gatttgggaa tcgtataaga actgtatgag accac                               215


<210> SEQ ID NO 45
<211> LENGTH: 190
<212> TYPE: DNA
<213> ORGANISM: Homo sapiens

<400> SEQUENCE: 45

agctctagct tgaattggtg ccactgttcg gcatcgttgt gtttcgatct ctacaatttc     60

gttacggtag cctctccagc tctagcctag ctatttgcat gtcgctatgt gttctgggaa    120

atcaccataa acgtgaaatg tctttggatt tgggaatctt ataagttctg tatgagacca    180

ctctttccca                                                           190
```

NUCLEIC ACID CONSTRUCTS FOR VA RNA TRANSCRIPTION

CROSS-REFERENCE TO RELATED APPLICATIONS

This application claims priority to European Patent Application No. 20202010.3 filed Oct. 15, 2020, all of which are incorporated by reference in its entirety.

SEQUENCE LISTING

This application contains a Sequence Listing which has been submitted electronically in ASCII format and is hereby incorporated by reference in its entirety. Said ASCII copy, created on Oct. 7, 2021, is named P36313-US_Sequence_Listing.txt and is 34,317 bytes in size.

FIELD OF INVENTION

Herein are reported novel DNA constructs and methods of using the same. With the novel DNA constructs according to the current invention adenoviral VA RNA can be transcribed in AAV particle production cell lines. The novel VA RNA nucleic acid comprises the VA RNA nucleic acid operably linked to an exogenous promoter.

BACKGROUND OF THE INVENTION

Gene therapy refers broadly to the therapeutic administration of genetic material to modify gene expression of living cells and thereby alter their biological properties. After decades of research, gene therapies have progressed to the market and are expected to become increasingly important. In general, gene therapy can be divided into either in vivo or ex vivo approaches.

Today, most in vivo therapies rely on DNA delivery with recombinant adeno-associated viral (rAAV) vectors. An AAV is a small, naturally occurring, non-pathogenic parvovirus, which is composed of a non-enveloped icosahedral capsid. It contains a linear, single stranded DNA genome of approximately 4.7 kb. The genome of wild-type AAV vectors carries two genes, rep and cap, which are flanked by inverted terminal repeats (ITRs). ITRs are necessary in cis for viral replication and packaging. The rep gene encodes for four different proteins, whose expression is driven by two alternative promoters, P5 and P19. Additionally different forms are generated by alternative splicing. The Rep proteins have multiple functions, such as, e.g., DNA binding, endonuclease and helicase activity. They play a role in gene regulation, site-specific integration, excision, replication and packaging. The cap gene codes for three capsid proteins and one assembly-activating protein. Differential expression of these proteins is accomplished by alternative splicing and alternative start codon usage and driven by a single promoter, P40, which is located in the coding region of the rep gene.

In engineered, therapeutic rAAV vectors, the viral genes are replaced with a transgene expression cassette, which remains flanked by the viral ITRs, but encodes a gene of interest under the control of a promoter of choice. Unlike the wild-type virus, the engineered rAAV vector does not undergo site-specific integration into the host genome, remaining predominantly episomal in the nucleus of transduced cells.

An AAV is not replication competent by itself but requires the function of helper genes. These are provided in nature by co-infected helper viruses, such as, e.g., adenovirus or herpes simplex virus. For instance, five adenoviral genes, i.e. ETA, E1B, E2A, E4 and VA, are known to be essential for AAV replication. In contrast to the other helper genes, which code for proteins, VA is a small RNA gene.

For the production of rAAV vectors, DNA carrying the transgene flanked by ITRs is introduced into a packaging host cell line, which also comprise rep and cap genes as well as the required helper genes. There are many ways of introducing these three groups of DNA elements into cells and ways of combining them on different DNA plasmids (see, e.g., Robert, M. A., et al. Biotechnol. J. 12 (2017) 1600193).

Two general production methods are widely used. In the triple transfection method, HEK293 cells, which already express adenovirus E1A and E1B, are transiently co-transfected with an adenovirus helper plasmid (pHELPER) carrying E2A, E4 and VA, a plasmid comprising rep/cap and a plasmid comprising the rAAV-transgene.

Alternatively, rep/cap and viral helper genes can be combined on one larger plasmid (dual transfection method). The second method encompasses the infection of insect cells (Sf9) with two baculoviruses, one carrying the rAAV genome and the other carrying rep and cap. In this systems helper functions are provided by the baculovirus vector itself. In the same way, herpes simplex virus is used in combination with HEK293 cells or BHK cells. More recently Mietzsch et al. (Hum. Gene Ther. 25 (2014) 212-222; Hum. Gene Ther. Methods 28 (2017) 15-22) engineered Sf9 cells with rep and cap stably integrated into the genome. With these cells a single baculovirus carrying the rAAV transgene is sufficient to produce rAAV vectors. Clark et al. (Hum. Gene Ther. 6 (1995) 1329-1341) generated a HeLa cell line with rep/cap genes and a rAAV transgene integrated in its genome. By transfecting the cells with wild-type adenovirus, rAAV vector production is induced and mixed stocks of rAAV vectors and adenovirus are produced.

No mammalian cell line with helper genes stably integrated into its genome have been described so far. Expression of rep as well as viral helper genes is toxic to cells and needs to be tightly controlled (see, e.g., Qiao, C., et al., J. Virol. 76 (2002) 1904-1913).

For rep genes such a control has been accomplished by introducing an intron into the rep gene that contains a polyadenylation sites flanked by LoxP sites. After introducing Cre-recombinase with the help of a recombinant adenovirus, the polyadenylation sites are removed and the intron is spliced out (see, e.g., Yuan, Z., et al., Hum. Gene Ther. 22 (2011) 613-624; Qiao, C., et al., supra).

WO 97/9441 (EP 0 850 313 B1) reported a method for producing recombinant adeno-associated virus (AAV), which comprises the steps of: (1) culturing a composition comprising cells which have been transiently transfected with: (a) an AAV helper plasmid comprising nucleic acids encoding AAV rep and cap proteins; (b) an adenoviral helper plasmid comprising essential adenovirus helper genes, said essential adenovirus helper genes present in said plasmid being selected from the group consisting of E1A, E1B, E2A, E4, E40RF6, E40RF6/7, VA RNA and combinations thereof, and (c) an AAV plasmid comprising first and second AAV inverted terminal repeats (ITRs), wherein said first and second AAV ITRs flank a DNA encoding a polypeptide of interest, said DNA being operably linked to a promoter DNA; in the absence of adenovirus particles; and (2) purifying recombinant AAV produced therefrom.

WO 2001/36615 (EP 1 230 354 B1) reported a permanent amniocytic cell line comprising at least one nucleic acid which brings about expression of the gene products of the adenovirus E1A and E1B regions.

WO 2004/29219 reported vectors and methods for controlling the temporal and spatial expression of a shRNA construct in cells and organisms. Such vectors may be retroviral vectors, such as lentiviral vectors. In preferred embodiments, expression of a shRNA is regulated by an RNA polymerase III promoter; such promoters are known to produce efficient silencing. While essentially any polIII promoter may be used, desirable examples include the human U6 snRNA promoter, the mouse U6 snRNA promoter, the human and mouse H1 RNA promoter and the human tRNA-val promoter.

Ventura, A., et al. reported Cre-lox-regulated conditional RNA interference from transgenes (Proc. Natl. Acad. Sci. USA 101 (2004) 10380-10385). The authors have generated two lentiviral vectors for conditional, Cre-lox-regulated RNA interference. One vector allows for conditional activation, whereas the other permits conditional inactivation of short hairpin RNA (shRNA) expression. The former is based on a strategy in which the mouse U6 promoter has been modified by including a hybrid between a LoxP site and a TATA box.

Kawabe, Y., et al. reported a gene integration system for antibody production using recombinant Chinese hamster ovary (CHO) cells (Cytotechnol. 64 (2012) 267-279). An exchange cassette flanked by wild-type and mutated LoxP sites was integrated into the chromosome of CHO cells for the establishment of recipient founder cells. Then, a donor plasmid including a marker-antibody-expression cassette flanked by a compatible pair of LoxP sites and also comprising an internal not-paired LoxP site between the expression cassette for the selection marker and the expression cassette of the antibody was prepared. The donor plasmid and a Cre-recombinase expression plasmid were co-transfected into the founder CHO cells to give rise to RMCE in the CHO genome, resulting in site-specific integration of the antibody gene restoring the original wild-type LoxP site and generating an inactive double-mutated LoxP site that no longer participates in RMCE. The RMCE procedure was repeated to increase the copy numbers of the integrated gene whereby in each step the expression cassette for the selection marker present in the cell was excised and removed.

US 2013/58871 reported the generation of a Cre-recombinase-mediated switchable inversion plasmid by using two mutant LoxP sites (Lox66 and Lox71) oriented in a head-to-head position. When Cre-recombinase is present, the gene flanked by the two mutant LoxP sites is inverted, forming one LoxP and one double-mutated LoxP site. Because the double-mutated LoxP site shows very low affinity for Cre-recombinase, the favorable one-step inversion is nearly irreversible, allowing the gene to be stably switched 'on' and 'off' as desired. Leakiness of expression in the absence of Cre-recombinase was minimized by eliminating sequences containing false TATA boxes and start codons at the sides of the floxed gene.

Crawford, Y., et al. (Biotechnol. Prog. 29 (2013) 1307-1315) reported the fast identification of reliable hosts for targeted cell line development from a limited-genome screening using combined phiC31 integrase and CRE-Lox technologies.

WO 2016/57800 reported a TGG or DRG promoter operably linked to a Cre-recombinase and a LOX-stop-LOX inducible RNA polymerase III promoter operably linked to an inhibitory RNA. In vivo, the authors have found that a single T to C mutation at position 4 of the central spacer region in the distal (3') LoxP site completely inhibited the recombination reaction in two conditional mouse models.

WO 2019/126634 reported targeted integration (TI) host cells suitable for the expression of recombinant proteins, as well as methods of producing and using said TI host cells.

SUMMARY OF THE INVENTION

Herein are reported novel deoxyribonucleic acids comprising an adenoviral VA RNA and methods using the same. The novel deoxyribonucleic acids according to the current invention are useful in the production of recombinant adeno-associated virus particles.

Thus, one aspect of the current invention is an adenoviral VA RNA nucleic acid. In the adenoviral VA RNA nucleic acid reported herein, the VA RNA coding sequence is operably linked at its 5'-terminus to a variant type 2 polymerase III promoter, or a type 3 polymerase III promoter or variant thereof, such as, e.g., the U6-snRNA promoter, or a polymerase II promoter.

In the adenoviral VA RNA nucleic acid according to the current invention the VA RNA coding sequence is operably linked at its 5'-terminus to the U6-snRNA promoter.

In the adenoviral VA RNA nucleic acid according to the current invention the VA RNA coding sequence is operably linked at its 5'-terminus to an inducible promoter.

In one preferred embodiment, the adenoviral VA RNA coding sequence has the sequence of SEQ ID NO: 38.

In one embodiment of all aspects and embodiments, the adenoviral VA RNA nucleic acid comprises a precise transcription start site located 3' to the promoter. In one embodiment, the precise transcription start site comprises in 5'- to 3'-direction at least the six 5'-terminal nucleotides of an adenoviral VA RNAI gene comprising the transcription start site (TSS) (to prevent by-passing of the subsequent polymerase III (pol III) terminator) and a functional polymerase III terminator (to prevent transcription from the constitutively active upstream promoter).

In one embodiment of all aspects and embodiments, the adenoviral VA RNA nucleic acid comprises a polymerase III terminator at its 3'-terminus.

In one embodiment of all aspects and embodiments, all elements of the adenoviral VA RNA nucleic acid are arranged in an operably linked form.

In one embodiment of all aspects and embodiments, the adenoviral VA RNA nucleic acid is functional.

Without being bound by this theory it is assumed that an improved control of adenoviral VA RNA transcription and thereby AAV particle production can be achieved with the nucleic acid according to the current invention.

Another aspect of the current invention is a packaging cell (line) for rAAV particle production, wherein rep/cap genes as well as adenoviral helper genes are (stably) integrated into the genome and wherein the adenoviral VA RNA nucleic acid comprises an adenoviral VA RNA nucleic acid according to the current invention.

In one preferred embodiment of this aspect, the rAAV plasmid, comprising the ITRs and the transgene, is also integrated in the packaging cell's genome. Thereby a packaging cell line is turned into a rAAV vector and particle producing cell line. Likewise, in certain embodiments, the rAAV plasmid/genome is introduced transiently.

After recombination, the cells of the producing cell line are genetically uniform and express all genes that are required for replication and packaging of the rAAV in the correct stoichiometry (in contrast thereto, in triple or dual transfection methods some cells may receive suboptimal doses of one or the other plasmids). Thus, without being bound by this theory, a stable rAAV vector/particle packaging or producing cell may result in higher product quality compared to transient packaging or producing cells.

One independent aspect of the current invention is a DNA (molecule) comprising an adenoviral VA RNA nucleic acid according to the current invention, a first DNA element, optionally a second DNA element, optionally a third DNA element, and optionally a rep or/and cap open reading frame.

In one dependent embodiment of this aspect the first DNA element comprises an E1A open reading frame and an E1B open reading frame; and the second DNA element, if present, comprises an E2A open reading frame and an E4 or E4orf6 open reading frame, or vice versa.

One independent aspect of the current invention is a mammalian or insect cell comprising an adenoviral VA RNA nucleic acid or a DNA (element) according to the current invention.

One independent aspect of the current invention is a method for producing a recombinant adeno-associated virus (rAAV) vector or particle comprising the following steps:

cultivating/propagating a cell according to the current invention (under conditions suitable for cell division), and recovering the rAAV vector or particle from the cells or the cultivation medium.

A further independent aspect of the current invention is an adenoviral VA RNA nucleic acid or a DNA (molecule) according to the current invention for the production of recombinant adeno-associated virus vectors or particles.

One independent aspect of the current invention is an adenoviral VA RNA nucleic acid, wherein the wild-type type 2 polymerase III promoter has been inactivated/deleted/removed, and the U6-snRNA promoter has been added. In one embodiment, further a precise transcription start site has been added.

One independent aspect of the invention is a method of generating/for producing a recombinant adeno-associated virus (rAAV) vector or particle, wherein the method comprises:

generating/providing a mammalian, in suspension growing cell, which comprises either stably integrated into its genome or transiently present a transgene expression cassette interspaced between two AAV ITRs;

open reading frames encoding adenoviral E1A, E1B, E2A, E4 or E4orf6 proteins and an adenoviral VA RNA nucleic acid according to the current invention;

open reading frames encoding adeno-associated Rep/Cap proteins;

propagating/cultivating the mammalian cell (under conditions to allow cell division); and isolating the rAAV vector or particle from the cell or the cultivation medium and thereby producing the rAAV vector or particle.

DETAILED DESCRIPTION OF EMBODIMENTS OF THE INVENTION

Herein are reported novel nucleic acids and DNA elements as well as methods using the same. The nucleic acids according to the current invention are useful in the recombinant production of AAV particles. The current invention uses a deliberate arrangement of promoter and coding sequence to provide a novel adenoviral VA RNA nucleic acid.

Definitions

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and 11 (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation of derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

Deoxyribonucleic acids comprise a coding and a non-coding strand. The terms “5'-” and “3'-” when used herein refer to the position on the coding strand.

The term “3'-flanking sequence” denotes a sequence located at the 3'-end (downstream of, below) a nucleotide sequence.

The term “5'-flanking sequence” denotes a sequence located at the 5'-end (upstream of, above) a nucleotide sequence.

It must be noted that as used herein and in the appended claims, the singular forms “a”, “an”, and “the” include plural reference unless the context clearly dictates otherwise. Thus, for example, reference to “a cell” includes a plurality of such cells and equivalents thereof known to those skilled in the art, and so forth. As well, the terms “a” (or “an”), “one or more” and “at least one” can be used interchangeably herein. It is also to be noted that the terms “comprising”, “including”, and “having” can be used interchangeably.

The term “AAV helper functions” denotes AAV-derived coding sequences (proteins) which can be expressed to provide AAV gene products and AAV particles that, in turn, function in trans for productive AAV replication and packaging. Thus, AAV helper functions include AAV open reading frames (ORFs), including rep and cap and others such as AAP for certain AAV serotypes. The rep gene expression products have been shown to possess many functions, including, among others: recognition, binding and nicking of the AAV origin of DNA replication; DNA helicase activity; and modulation of transcription from AAV (or other heterologous) promoters. The cap gene expression products (capsids) supply necessary packaging functions. AAV helper functions are used to complement AAV functions in trans that are missing from AAV vector genomes.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "comprising" also encompasses the term "consisting of".

The terms "empty capsid" and "empty particle" refer to an AAV particle that has an AAV protein shell but that lacks in whole or part a nucleic acid that encodes a protein or is transcribed into a transcript of interest flanked by AAV ITRs, i.e. a vector. Accordingly, the empty capsid does not function to transfer a nucleic acid that encodes a protein or is transcribed into a transcript of interest into the host cell.

The term "endogenous" denotes that something is naturally occurring within a cell; naturally produced by a cell; likewise, an "endogenous gene locus/cell-endogenous gene locus" is a naturally occurring locus in a cell.

As used herein, the term "exogenous" indicates that a nucleotide sequence does not originate from a specific cell and is introduced into said cell by DNA delivery methods, e.g., by transfection, electroporation, or transduction by viral vectors. Thus, an exogenous nucleotide sequence is an artificial sequence wherein the artificiality can originate, e.g., from the combination of subsequences of different origin (e.g. a combination of a recombinase recognition sequence with an SV40 promoter and a coding sequence of green fluorescent protein is an artificial nucleic acid) or from the deletion of parts of a sequence (e.g. a sequence coding only the extracellular domain of a membrane-bound receptor or a cDNA) or the mutation of nucleobases. The term "endogenous" refers to a nucleotide sequence originating from a cell. An "exogenous" nucleotide sequence can have an "endogenous" counterpart that is identical in base compositions, but where the sequence is becoming an "exogenous" sequence by its introduction into the cell, e.g., via recombinant DNA technology.

As used herein, the term "flanking" denotes that a first nucleotide sequence is located at either a 5'- or 3'-end, or both ends of a second nucleotide sequence. The flanking nucleotide sequence can be adjacent to or at a defined distance from the second nucleotide sequence. There is no specific limit of the length of a flanking nucleotide sequence beside practical requirements. For example, a flanking sequence can be a few base pairs or a few thousand base pairs. The term "flanking nucleotide sequence" denotes a sequence segment of a nucleic acid that precedes or follows the sequence to be inserted (=target sequence).

The term "gene locus" denotes the location of a gene on a chromosome, i.e. the position of a gene in the genome, i.e. the gene location.

An "isolated" composition is one, which has been separated from one or more component(s) of its natural environment. In some embodiments, a composition is purified to greater than 95% or 99% purity as determined by, for example, electrophoretic (e.g., SDS-PAGE, isoelectric focusing (IEF), capillary electrophoresis, CE-SDS) or chromatographic (e.g., size exclusion chromatography or ion exchange or reverse phase HPLC). For review of methods for assessment of e.g. antibody purity, see, e.g., Flatman, S. et al., J. Chrom. B 848 (2007) 79-87.

An "isolated" nucleic acid refers to a nucleic acid molecule that has been separated from one or more component (s) of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated" polypeptide or antibody refers to a polypeptide molecule or antibody molecule that has been separated from one or more component(s) of its natural environment.

The term "integration site" denotes a nucleic acid sequence within a cell's genome into which an exogenous nucleotide sequence is/has been inserted. In certain embodiments, an integration site is between two adjacent nucleotides in the cell's genome. In certain embodiments, an integration site includes a stretch of nucleotides. In certain embodiments, the integration site is located within a specific locus of the genome of a mammalian cell. In certain embodiments, the integration site is within an endogenous gene of a mammalian cell.

The term "LoxP site" denotes a nucleotide sequence of 34 bp in length consisting of two palindromic 13 bp sequences (inverted repeats) at the termini (ATAACTTCGTATA (SEQ ID NO: 01) and TATACGAAGTTAT (SEQ ID NO: 02), respectively) and a central 8 bp core (not symmetric) spacer sequence. The spacer sequences determine the orientation of the LoxP site. Depending on the relative orientation and location of two LoxP sites with respect to each other, the intervening DNA is either excised (LoxP sites oriented in the same direction) or inverted (LoxP sites orientated in opposite directions). The term "floxed" denotes a DNA sequence located between two LoxP sites. If there are two floxed sequences, i.e. a target floxed sequence in the genome and a floxed sequence in a donor nucleic acid, both sequences can be exchanged with each other. This is called "recombinase-mediated cassette exchange".

Exemplary LoxP sites are shown in the following Table:

| name | core sequence | SEQ ID NO: |
|---|---|---|
| LoxP | ATGTATGC | 03 |
| L3 | AAGTCTCC | 04 |
| L2 (inverted) | GCATACAT | 05 |
| LoxFas | TACCTTTC | 06 |
| Lox511 | ATGTATAC | 07 |
| Lox5171 | ATGTGTAC | 08 |
| Lox2272 | AAGTATCC | 09 |
| Loxm2 | AGAAACCA | 10 |
| Loxm3 | TAATACCA | 11 |
| Loxm7 | AGATAGAA | 12 |

The term "mammalian cell comprising an exogenous nucleotide sequence" encompasses cells into which one or more exogenous nucleic acid(s) have been introduced, including the progeny of such cells. These can be the starting point for further genetic modification. Thus, the term "a mammalian cell comprising an exogenous nucleotide sequence" encompasses a cell comprising an exogenous nucleotide sequence integrated at a single site within a locus of the genome of said mammalian cell, wherein the exogenous nucleotide sequence comprises at least a first and a second recombination recognition site (these recombination recognition sites are different) flanking at least one first selection marker. In certain embodiments, the mammalian cell comprising an exogenous nucleotide sequence is a cell comprising an exogenous nucleotide sequence integrated at a single site within a locus of the genome of said cell, wherein the exogenous nucleotide sequence comprises a first and a second recombination recognition sequence flanking at least one first selection marker, and a third recombination recognition sequence located between the first and the second recombination recognition sequence, and all the recombination recognition sequences are different.

A "mammalian cell comprising an exogenous nucleotide sequence" and a "recombinant cell" are both "transfected cells". This term includes the primary transfected cell as well as progeny derived therefrom without regard to the number of passages. Progeny, e.g., may not be completely identical in nucleic acid content to a parent cell, but may contain mutations. Mutant progeny that has the same function or biological activity as the originally transfected cell are encompassed.

The "nucleic acids encoding AAV packaging proteins" refer generally to one or more nucleic acid molecule(s) that includes nucleotide sequences providing AAV functions deleted from an AAV vector, which is(are) to be used to produce a transduction competent recombinant AAV particle. The nucleic acids encoding AAV packaging proteins are commonly used to provide expression of AAV rep and/or cap genes to complement missing AAV functions that are necessary for AAV replication; however, the nucleic acid constructs lack AAV ITRs and can neither replicate nor package themselves. Nucleic acids encoding AAV packaging proteins can be in the form of a plasmid, phage, transposon, cosmid, virus, or particle. A number of nucleic acid constructs have been described, such as the commonly used plasmids pAAV/Ad and pIM29+45, which encode both rep and cap gene expression products (see, e.g., Samulski et al. (1989) J. Virol. 63:3822-3828; and McCarty et al. (1991) J. Virol. 65:2936-2945). A number of plasmids have been described which encode rep and/or cap gene expression products (e.g., U.S. Pat. Nos. 5,139,941 and 6,376,237). Any one of these nucleic acids encoding AAV packaging proteins can comprise the DNA element or nucleic acid according to the invention.

The term "nucleic acids encoding helper proteins" refers generally to one or more nucleic acid molecule(s) that include nucleotide sequences encoding proteins that provide adenoviral helper function(s). A plasmid with nucleic acid(s) encoding helper protein(s) can be transfected into a suitable cell, wherein the plasmid is then capable of supporting AAV particle production in said cell. Any one of these nucleic acids encoding helper proteins can comprise the DNA element or nucleic acid according to the invention. Expressly excluded from the term are infectious viral particles, as they exist in nature, such as adenovirus, herpesvirus or vaccinia virus particles.

As used herein, the term "operably linked" refers to a juxtaposition of two or more components, wherein the components are in a relationship permitting them to function in their intended manner. For example, a promoter and/or an enhancer is operably linked to a coding sequence/open reading frame/gene if the promoter and/or enhancer acts to modulate the transcription of the coding sequence/open reading frame/gene. In certain embodiments, DNA sequences that are "operably linked" are contiguous. In certain embodiments, e.g., when it is necessary to join two protein encoding regions, such as a secretory leader and a polypeptide, the sequences are contiguous and in the same reading frame. In certain embodiments, an operably linked promoter is located upstream of the coding sequence/open reading frame/gene and can be adjacent to it. In certain embodiments, e.g., with respect to enhancer sequences modulating the expression of a coding sequence/open reading frame/gene, the two components can be operably linked although not adjacent. An enhancer is operably linked to a coding sequence/open reading frame/gene if the enhancer increases transcription of the coding sequence/open reading frame/gene. Operably linked enhancers can be located upstream, within, or downstream of coding sequences/open reading frames/genes and can be located at a considerable distance from the promoter of the coding sequence/open reading frame/gene.

The term "packaging proteins" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-I) and vaccinia virus.

As used herein, "AAV packaging proteins" refer to AAV-derived sequences, which function in trans for productive AAV replication. Thus, AAV packaging proteins are encoded by the major AAV open reading frames (ORFs), rep and cap. The rep proteins have been shown to possess many functions, including, among others: recognition, binding and nicking of the AAV origin of DNA replication; DNA helicase activity; and modulation of transcription from AAV (or other heterologous) promoters. The cap (capsid) proteins supply necessary packaging functions. AAV packaging proteins are used herein to complement AAV functions in trans that are missing from AAV vectors.

A "plasmid" is a form of nucleic acid or polynucleotide that typically has additional elements for expression (e.g., transcription, replication, etc.) or propagation (replication) of the plasmid. A plasmid as used herein also can be used to reference such nucleic acid or polynucleotide sequences. Accordingly, in all aspects the inventive compositions and methods are applicable to nucleic acids, polynucleotides, as well as plasmids, e.g., for producing cells that produce viral (e.g., AAV) vectors, to produce viral (e.g., AAV) particles, to produce cell culture medium that comprises viral (e.g., AAV) particles, etc.

The term "recombinant cell" as used herein denotes a cell after final genetic modification, such as, e.g., a cell producing an AAV particle of interest and that can be used for the production of said AAV particle of interest at any scale. For example, "a mammalian cell comprising an exogenous nucleotide sequence" that has been subjected to recombinase mediated cassette exchange (RMCE) whereby the coding sequences for a polypeptide of interest have been introduced into the genome of the host cell is a "recombinant cell". Although the cell is still capable of performing further RMCE reactions, it is not intended to do so.

A "recombinant AAV vector" is derived from the wild-type genome of a virus, such as AAV, by using molecular biological methods to remove the wild-type genome from the virus (e.g., AAV), and replacing it with a non-native nucleic acid, such as a nucleic acid transcribed into a transcript or that encodes a protein. Typically, for AAV one or both inverted terminal repeat (ITR) sequences of the wild-type AAV genome are retained in the recombinant AAV vector. A "recombinant" AAV vector is distinguished from a wild-type viral AAV genome, since all or a part of the viral genome has been replaced with a non-native (i.e., heterologous) sequence with respect to the viral genomic nucleic acid. Incorporation of a non-native sequence therefore defines the viral vector (e.g., AAV) as a "recombinant" vector, which in the case of AAV can be referred to as a "rAAV vector."

A recombinant vector (e.g., AAV) sequence can be packaged—referred to herein as a "particle"—for subsequent infection (transduction) of a cell, ex vivo, in vitro or in vivo. Where a recombinant vector sequence is encapsulated or packaged into an AAV particle, the particle can also be referred to as a "rAAV". Such particles include proteins that encapsulate or package the vector genome. Particular examples include viral envelope proteins, and in the case of AAV, capsid proteins, such as AAV VP1, VP2 and VP3.

A "recombination recognition site" (RRS) is a nucleotide sequence recognized by a recombinase and is necessary and sufficient for recombinase-mediated recombination events. A RRS can be used to define the position where a recombination event will occur in a nucleotide sequence.

As used herein, the term "selection marker" denotes a gene that allows cells carrying the gene to be specifically selected for or against, in the presence of a corresponding selection agent. For example, but not by way of limitation, a selection marker can allow the host cell transformed with the selection marker gene to be positively selected for in the presence of the respective selection agent (selective cultivation conditions); a non-transformed host cell would not be capable of growing or surviving under the selective cultivation conditions. Selection markers can be positive, negative or bi-functional. Positive selection markers can allow selection for cells carrying the marker, whereas negative selection markers can allow cells carrying the marker to be selectively eliminated. A selection marker can confer resistance to a drug or compensate for a metabolic or catabolic defect in the host cell. In prokaryotic cells, amongst others, genes conferring resistance against ampicillin, tetracycline, kanamycin or chloramphenicol can be used. Resistance genes useful as selection markers in eukaryotic cells include, but are not limited to, genes for aminoglycoside phosphotransferase (APH) (e.g., hygromycin phosphotransferase (HYG), neomycin and G418 APH), dihydrofolate reductase (DHFR), thymidine kinase (TK), glutamine synthetase (GS), asparagine synthetase, tryptophan synthetase (indole), histidinol dehydrogenase (histidinol D), and genes encoding resistance to puromycin, blasticidin, bleomycin, phleomycin, chloramphenicol, Zeocin, and mycophenolic acid. Further marker genes are described in WO 92/08796 and WO 94/28143.

Beyond facilitating a selection in the presence of a corresponding selection agent, a selection marker can alternatively be a molecule normally not present in the cell, e.g., green fluorescent protein (GFP), enhanced GFP (eGFP), synthetic GFP, yellow fluorescent protein (YFP), enhanced YFP (eYFP), cyan fluorescent protein (CFP), mPlum, mCherry, tdTomato, mStrawberry, J-red, DsRed-monomer, mOrange, mKO, mCitrine, Venus, YPet, Emerald, CyPet, mCFPm, Cerulean, and T-Sapphire.

Cells expressing such a molecule can be distinguished from cells not harboring this gene, e.g., by the detection or absence, respectively, of the fluorescence emitted by the encoded polypeptide.

As used herein, the term "serotype" is a distinction based on AAV capsids being serologically distinct. Serologic distinctiveness is determined based on the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

The terms "transduce" and "transfect" refer to introduction of a molecule such as a nucleic acid (viral vector, plasmid) into a cell. A cell has been "transduced" or "transfected" when exogenous nucleic acid has been introduced inside the cell membrane. Accordingly, a "transduced cell" is a cell into which a "nucleic acid" or "polynucleotide" has been introduced, or a progeny thereof in which an exogenous nucleic acid has been introduced. In particular embodiments, a "transduced" cell (e.g., in a mammal, such as a cell or tissue or organ cell) has a genetic change following incorporation of an exogenous molecule, for example, a nucleic acid (e.g., a transgene). A "transduced" cell(s) can be propagated and the introduced nucleic acid transcribed and/or protein expressed.

In a "transduced" or "transfected" cell, the nucleic acid (viral vector, plasmid) may or may not be integrated into genomic nucleic acid. If an introduced nucleic acid becomes integrated into the nucleic acid (genomic DNA) of the recipient cell or organism, it can be stably maintained in that cell or organism and further passed on to or inherited by progeny cells or organisms of the recipient cell or organism. Finally, the introduced nucleic acid may exist in the recipient cell or host organism extrachromosomally, or only transiently. A number of techniques are known, see, e.g., Graham et al. (1973) Virology, 52:456; Sambrook et al. (1989) Molecular Cloning, a laboratory manual, Cold Spring Harbor Laboratories, New York; Davis et al. (1986) Basic Methods in Molecular Biology, Elsevier; and Chu et al. (1981) Gene 13:197. Such techniques can be used to introduce one or more exogenous DNA moieties into suitable host cells.

The term "transgene" is used herein to conveniently refer to a nucleic acid that is intended or has been introduced into a cell or organism. Transgenes include any nucleic acid, such as a gene that is transcribed into a transcript or that encodes a polypeptide or protein.

A "vector" refers to the portion of the recombinant plasmid sequence ultimately packaged or encapsulated, either directly or in form of a single strand or RNA, to form a viral (e.g., AAV) particle. In cases recombinant plasmids are used to construct or manufacture recombinant viral particles, the viral particle does not include the portion of the "plasmid" that does not correspond to the vector sequence of the recombinant plasmid. This non-vector portion of the recombinant plasmid is referred to as the "plasmid backbone", which is important for cloning and amplification of the plasmid, a process that is needed for propagation and recombinant virus production, but is not itself packaged or encapsulated into viral (e.g., AAV) particles. Thus, a "vector" refers to the nucleic acid that is packaged in or encapsulated by a virus particle (e.g., AAV).

Recombinant Cell Line Generation

Generally, for efficient as well as large-scale production of a proteinaceous compound of interest, such as e.g. a rAAV particle or a therapeutic polypeptide, a cell stably expressing and, if possible, also secreting said proteinaceous compound is required. Such a cell is termed "recombinant cell" or "recombinant production cell". The process for generating such a recombinant cell is termed "cell line development" (CLD).

In a first step, a suitable host cell is transfected with the required nucleic acid sequences encoding said proteinaceous compound of interest. Transfection of additional helper polypeptides may be necessary. In a second step, a cell stably expressing the proteinaceous compound of interest is selected. This can be done, e.g., based on the co-expression of a selection marker, which had been co-transfected with the nucleic acid sequences encoding the proteinaceous compound of interest, or be the expression of the proteinaceous compound itself.

For expression of a coding sequence, i.e. of an open reading frame, additional regulatory elements, such as a promoter and polyadenylation signal (sequence), are necessary. Thus, an open reading frame is operably linked to said additional regulatory elements for transcription. This can be achieved by integrating it into a so-called expression cassette. The minimal regulatory elements required for an expression cassette to be functional in a mammalian cell are a promoter functional in said mammalian cell, which is located upstream, i.e. 5', to the open reading frame, and a polyadenylation signal (sequence) functional in said mammalian cell, which is located downstream, i.e. 3', to the open reading frame. Additionally a terminator sequence may be present 3' to the polyadenylation signal (sequence). For expression, the promoter, the open reading frame/coding region and the polyadenylation signal sequence have to be arranged in an operably linked form.

Likewise, a nucleic acid that is transcribed into a non-protein coding RNA is called "RNA gene". Also for expression of an RNA gene, additional regulatory elements, such as a promoter and a transcription termination signal or polyadenylation signal (sequence), are necessary. The nature and localization of such elements depends on the RNA polymerase that is intended to drive the expression of the RNA gene. Thus, an RNA gene is normally also integrated into an expression cassette.

In case the proteinaceous compound of interest is a heteromultimeric polypeptide, which is composed of different (monomeric) polypeptides, not only a single expression cassette is required but one for each of the different polypeptides, i.e. open reading frames/coding sequences, as well as RNA genes, if present. These expression cassettes differ at least in the contained open reading frame/coding sequences but can also differ in the promoter and/or polyadenylation signal sequence.

For example, in case the proteinaceous compound of interest is a full length antibody, which is a heteromultimeric polypeptide comprising two copies of a light chain as well as two copies of a heavy chain, two different expression cassettes are required, one for the light chain and one for the heavy chain. If, for example, the full-length antibody is a bispecific antibody, i.e. the antibody comprises two different binding sites specifically binding to two different antigens, each of the light chains as well as each of the heavy chains are also different from each other. Thus, a bispecific full-length antibody is composed of four different polypeptides and, therefore, four expression cassettes containing the four different open reading frames encoding the four different polypeptides are required.

In case the proteinaceous compound of interest is an AAV particle, which is composed of different (monomeric) polypeptides and a single stranded DNA molecule and which in addition requires other co-factors for production and encapsulation, a multitude of expression cassettes differing in the contained open reading frames/coding sequences are required. In this case, at least an expression cassette for each of the transgene, the different polypeptides forming the capsid of the AAV vector, for the required helper functions as well as the VA RNA are required. Thus, individual expression cassettes for each of the helper E1A, E1B, E2A, E4orf6, the VA RNA, the rep and cap genes are required.

As outlined in the previous paragraphs, the more complex the proteinaceous compound of interest or the higher the number of additional required helper polypeptides and/or RNAs, respectively, the higher is the number of required, different expression cassettes. Inherently with the number of expression cassettes, also the size of the nucleic acid to be integrated into the genome of the host cell increases. However, there is a practical upper limit to the size of a nucleic acid that can be transferred, which is in the range of about 15 kbps (kilo-base-pairs). Above this limit handling and processing efficiency profoundly drops. This issue can be addressed by using two or more separate nucleic acids. Thereby the different expression cassettes are allocated to different nucleic acids, whereby each nucleic acid comprises only some of the expression cassettes.

For cell line development random integration (RI) of the nucleic acid(s) carrying the expression cassettes for the proteinaceous compound of interest can be used. In general, by using RI the nucleic acids or fragments thereof integrate into the host cell's genome at random.

Alternatively, to RI, targeted integration (TI) can be used for CLD. In TI CLD, one or more nucleic acid(s) comprising the different expression cassettes is/are introduced at a predetermined locus in the host cell's genome.

In TI either homologous recombination or a recombinase mediated cassette exchange reaction (RMCE) can be employed for the integration of the nucleic acid(s) comprising the respective expression cassettes into the specific locus in the genome of the TI host cell.

In certain embodiments, a method for targeted integration of a single deoxyribonucleic acid into the genome of a (host) mammalian cell (i.e. a method for producing a recombinant mammalian cell), which thereafter comprises a nucleic acid encoding a proteinaceous compound and which thereafter produces said proteinaceous compound, comprising the following steps is provided:

a) providing a mammalian cell comprising an exogenous nucleotide sequence integrated at a defined (optionally single) site within a locus of the genome of the mammalian cell, wherein the exogenous nucleotide sequence comprises a first and a second recombination sequence flanking at least one first selection marker, whereby all recombination sequences are different or/and non-compatible (i.e. these do not result in cross-exchange reactions);

b) introducing into the mammalian cell provided in a) a deoxyribonucleic acid comprising two different recombination sequences and one to eight expression cassettes, wherein said deoxyribonucleic acid comprises in 5'- to 3'-direction, a first recombination sequence, one to eight expression cassette(s), whereof one expression cassette encodes one second selection marker, and a second recombination sequence, wherein the first and the second recombination sequence of the deoxyribonucleic acid are matching the first and the second recombination sequence on the integrated exogenous nucleotide sequence;

c) optionally introducing into or activating in said mammalian cell obtained in step b) a recombinase functional with said first and second recombination sequence (resulting in the exchange of the part of said exogenous nucleotide sequence between the first and second recombination sequence with the part of said deoxyribonucleic acid between the first and second recombination sequence and thereby integration of the latter into the genome said mammalian cell);

d) optionally selecting for cells expressing said second selection marker and producing the proteinaceous compound encoded by the introduced deoxyribonucleic acid, thereby producing a recombinant mammalian cell comprising a nucleic acid encoding a proteinaceous compound and producing said proteinaceous compound.

In certain embodiments, a method for simultaneous targeted integration of two deoxyribonucleic acids into the genome of a (host) mammalian cell (i.e. a method for producing a recombinant mammalian cell), which comprise nucleic acids encoding a proteinaceous compound and which optionally expresses said proteinaceous compound, comprising the following steps is provided:

a) providing a mammalian cell comprising an exogenous nucleotide sequence integrated at a defined (optionally single) site within a locus of the genome of the mammalian cell, wherein the exogenous nucleotide sequence comprises a first and a second recombination sequence flanking at least one first selection marker, and a third recombination sequence located between the first and the second recombination sequence, and all the recombination sequences are different or/and non-compatible (i.e. these do not result in cross-exchange reactions);

b) introducing into the cell provided in a) a composition of two deoxyribonucleic acids comprising three different recombination sequences and one to eight expression cassettes, wherein the first deoxyribonucleic acid comprises in 5'- to 3'-direction, a first recombination sequence, one or more (in one preferred embodiment up to four) expression cassette(s), a 5'-terminal part of an expression cassette encoding one second selection marker, and a first copy of a third recombination sequence, and the second deoxyribonucleic acid comprises in 5'- to 3'-direction a second copy of the third recombination sequence, a 3'-terminal part of an expression cassette encoding the one second selection marker, one or more (in one preferred embodiment up to four) expression cassette(s), and a second recombination sequence, wherein the first to third recombination sequences of the first and second deoxyribonucleic acids are matching the first to third recombination sequence on the integrated exogenous nucleotide sequence, wherein the 5'-terminal part and the 3'-terminal part of the expression cassette encoding the one second selection marker when taken together form a functional expression cassette of the one second selection marker;

c) optionally introducing into or activating in said mammalian cell obtained in step b) a recombinase functional with said first, second and third recombination sequence (resulting in the exchange of the part of said exogenous nucleotide sequence between the first and third as well as the part between the third and second recombination sequence with the part of said deoxyribonucleic acids between the first and third as well as the third and second recombination sequence and thereby integration of the latter into the genome said mammalian cell);

d) optionally selecting for cells expressing the second selection marker and optionally producing the proteinaceous product encoded by the introduced deoxyribonucleic acids, thereby producing a recombinant mammalian cell comprising a nucleic acid encoding said proteinaceous compound.

In order to increase the selection pressure the first selection marker is a negative selection marker, such as, e.g., in one embodiment, a thymidine kinase from herpes simplex virus (rendering cells sensitive to thymidine analogues, such as 5-iodo-2'-fluoro-2'-deoxy-1-β-D-arabino-furonosyl uracil (FIAU) or ganciclovir) or the diphtheria toxin fragment A from Corynebacterium diphtheria (causing toxicity by inhibiting protein synthesis; for example by phosphoglycerate kinase promoter (PGK)-driven expression of diphtheria toxin A fragment gene). During exchange with the introduced deoxyribonucleic acid, the negative selection marker is removed. This allows the discrimination between correct targeted integration and non-correct random integration.

In one embodiment of all aspects and embodiments, each of the expression cassettes comprise in 5'-to-3' direction a promoter, an open reading frame/coding sequence or an RNA gene and a polyadenylation signal sequence, and/or a terminator sequence. In one embodiment, the open reading frame encodes a polypeptide and the expression cassette comprises a polyadenylation signal sequence with or without additional terminator sequence. In one embodiment, the expression cassette comprises a RNA gene, the promoter is a polII promoter and a polyadenylation signal sequence or a polyU terminator is present. See, e.g., Song et al. Biochemical and Biophysical Research Communications 323 (2004) 573-578. In one embodiment, the expression cassette comprises a RNA nucleic acid, the promoter is a polIII promoter and a polyU terminator sequence.

In one embodiment of all aspects and embodiments, the open reading frame encodes a polypeptide, the promoter is the human CMV promoter with or without intron A, the polyadenylation signal sequence is the bGH (bovine growth hormone) polyA signal sequence and the terminator is the hGT (human gastrin terminator).

In one embodiment of all aspects and embodiments the promoter is the human CMV promoter with intron A, the polyadenylation signal sequence is the bGH polyadenylation signal sequence and the terminator is the hGT, except for the expression cassette of the RNA nucleic acid and the expression cassette of the selection marker, wherein for the selection marker the promoter is the SV40 promoter and the polyadenylation signal sequence is the SV40 polyadenylation signal sequence and a terminator is absent, and wherein for the RNA nucleic acid the promoter is a variant type 2 polymerase III promoter or a type 3 polymerase III promoter such as the U6-snRNA promoter and the terminator is a polymerase II or III terminator.

In one embodiment of all previous aspects and embodiments, the human CMV promoter has the sequence of SEQ ID NO: 13. In one embodiment, the human CMV promoter has the sequence of SEQ ID NO: 14. In one embodiment, the human CMV promoter has the sequence of SEQ ID NO: 15.

In one embodiment of all previous aspects and embodiments, the BGH polyadenylation signal sequence is SEQ ID NO: 16.

In one embodiment of all previous aspects and embodiments, the hGT has the sequence of SEQ ID NO: 17.

In one embodiment of all previous aspects and embodiments, the SV40 promoter has the sequence of SEQ ID NO: 18.

In one embodiment of all previous aspects and embodiments, the SV40 polyadenylation signal sequence is SEQ ID NO: 19.

It has to be pointed out that the current invention does not encompass permanent human cell lines comprising a nucleic acid sequence for the adenoviral gene functions E1A and E1B and the nucleic acid sequence for the SV40 large T-antigen or the Epstein-Barr virus (EBV) nuclear antigen 1 (EBNA-1).

Homologous Recombination

In certain embodiments, the targeted integration is mediated by homologous recombination.

Targeted integration by homologous recombination is an established technology in the art. For example, for more than 30 years homologous recombination has been used to introduce specific genetic modifications in a site-specific manner in murine embryonic stem cells (Doetschman, T., et al., Nature 330 (1987) 576-578; Thomas, K. R. and Capecchi, M. R., Cell 51 (1987) 503-512; Thompson, S., et al., Cell 56 (1989) 313-321; Zijlstra, M., et al., Nature 342 (1989) 435-438; Bouabe, H. and Okkenhaug, K., Meth. Mol. Biol. 1064 (2013) 315-336).

In case of the use of homologous recombination for targeted integration, the recombination sequences are sequences homologous to the exogenous nucleic acid sequence and are termed "homology arms". In this case, the deoxyribonucleic acid introduced into the host cell comprises as first recombination sequence a sequence that is homologous to the sequence 5' (upstream) to the exogenous nucleic acid sequence (i.e. the landing site) and as second recombination sequence a sequence that is homologous to the sequence 3' (downstream) to the exogenous nucleic acid sequence. Generally, the targeted integration frequency increases with the length as well as with the isogenicity of the homology arms. Ideally, the homology arms are derived from genomic DNA prepared from the respective host cell.

Nucleases

In certain embodiments, the targeted integration is by homologous recombination mediated by a site-specific nuclease.

In one embodiment, the site-specific nuclease is selected from Zink finger nuclease (ZFN), transcription activator-like effector nucleases (TALENs) and the clustered regularly interspaced short palindromic repeats (CRISPR)/CRISP-Rassociated protein-9 nuclease (Cas9) system.

Nuclease-encoding genes can be delivered into cells by plasmid DNA, viral vectors, or in vitro transcribed mRNA. Transfection of plasmid DNA or mRNA can be done by electroporation or cationic lipid-based reagents. Integrase-deficient lentiviral vectors can be used for delivering nucleases into transfection-resistant cell types. AAV vectors can also be used for nuclease delivery.

Recombinases

Recombination systems, such as Cre/LoxP or Flp/FRT, can be used for the exchange of partial nucleic acid sequences between different nucleic acid molecules, the excision of nucleic acid fragments from nucleic acid molecules, or the inversion of parts within a nucleic acid molecule. The result of the action of the recombinase can be permanent using a single on/off-event, it can be for a defined, but limited, period of time, and it can be adjusted to a defined, and thereby, specific cell type or tissue.

Flp-Recombinase

The Flp/FRT site-specific recombination system involves recombination of sequences between the flippase recognition target (FRT) sites by the recombinase flippase (Flp). Flippase originates from Saccharomyces cerevisiae. The sequence of Flp is available, e.g., from UniProt P03870. The 34 bp FRT site has the sequence of GAAGTTCCTATTCtctagaaaGAATAGGAACTTC (SEQ ID NO: 20; central spacer sequence in lower case letters), wherein the Flp-recombinase binds to the inverted 13 bp repeats of GAAGTTCCTATTC (forward SEQ ID NO: 21; inverse SEQ ID NO: 22) flanking the 8 bp central spacer sequence.

Exemplary FRT sites are shown in the following Table (see Branda and Dymecki, Dev. Cell 6 (2004) 7-28):

| name | spacer sequence | SEQ ID NO: |
|---|---|---|
| wild-type | TCTAGAAA | 23 |
| F3 | TTCAAATA | 24 |
| F5 | TTCAAAAG | 25 |

Cre-Recombinase

The Cre/LoxP site-specific recombination system has been widely used in many biological experimental systems. Cre-recombinase is a 38-kDa site-specific DNA recombinase that recognizes 34 bp LoxP sequences. Cre-recombinase is derived from bacteriophage P1 and belongs to the tyrosine family site-specific recombinase. Cre-recombinase can mediate both intra- and intermolecular recombination between LoxP sequences. The canonical LoxP sequence is composed of an 8 bp non-palindromic spacer sequence flanked by two 13 bp inverted repeats. Cre-recombinase binds to the 13 bp repeat thereby mediating recombination within the 8 bp spacer sequence. Cre/LoxP-mediated recombination occurs at a high efficiency and does not require other host factors. If two LoxP sequences are placed in the same orientation on the same nucleotide sequence, Cre-recombinase-mediated recombination will excise the DNA sequence located between the two LoxP sequences as a covalently closed circle. If two LoxP sequences are placed in an inverted/reciprocal orientation with respect to each other on the same nucleotide sequence, Cre-recombinase-mediated recombination will invert the orientation of the DNA sequences located between the two LoxP sequences. If two LoxP sequences are on two different DNA molecules and if one DNA molecule is circular, Cre-recombinase-mediated recombination will result in integration of the circular DNA sequence.

Cre-recombinase can be introduced into or activated inside cells with any known method. For example, using liposome-based gene delivery (WO 93/24640; Mannino and Gould-Fogerite, BioTechniques 6 (1988) 682-691; U.S. Pat. No. 5,279,833; WO 91/06309; Feigner et al., Proc. Natl. Acad. Sci. USA 84 (9871) 7413-7414), or viral vectors such as papilloma viral, retro viral and adeno-associated viral vectors (e.g., Berns et al., Ann. NY Acad. Sci. 772 (1995) 95-104; Ali et al., Gene Ther. 1 (1994) 367-384; Haddada et al., Curr. Top. Microbiol. Immunol. 199 (1995) 297-306; Buchscher et al., J. Virol. 66 (1992) 2731-2739; Johann et al., J. Virol. 66 (1992) 1635-1640; Sommerfelt et al., Virol. 176 (1990) 58-59; Wilson et al., J. Virol. 63 (1989) 2374-2378; Miller et al., J. Virol. 65 (1991) 2220-2224; WO 94/26877; Rosenburg and Fauci in Fundamental Immunology, Third Edition Paul (ed.) Raven Press, Ltd., New York (1993) and the references therein; West et al., Virology 160 (1987) 38-47; U.S. Pat. No. 4,797,368; WO 93/24641; Kotin, Human Gene Therapy 5 (1994) 793-801; Muzyczka, J. Clin. Invest. 94 (1994) 1351; U.S. Pat. No. 5,173,414; Tratschin et al., Mol. Cell. Biol. 5 (1985) 3251-3260; Tratschin et al., Mol. Cell. Biol. 4 (1984) 2072-2081; Hermonat and Muzyczka, Proc. Natl. Acad. Sci. USA 81 (1984) 6466-6470; Samulski et al., J. Virol. 63 (1989) 3822-3828).

For example, a recombinant AAV vector of serotype 2 expressing Cre-recombinase has been described by Li, X., et al. (PLOS ONE 7 (2012) e50063) and Scammell, E., et al. (J. Neurosci. 23 (2003) 5762-5770). Using this rAAV-Cre a very complete recombination of the target LoxP sites could be induced. For rAAV vector-based delivery, see also, Muzyczka, Curr. Top. Microbiol. Immunol. 158 (1992) 97-129; U.S. Pat. No. 4,797,368; WO 91/18088; Samulski, Current Opinion in Genetic and Development 3 (1993) 74-80.

For example, a Cre-recombinase expression plasmid can be used.

For example, Cre-recombinase encoding mRNA can be used.

A large number of functional LoxP sites are known, such as, e.g., Lox511, Lox66, Lox11, Lox76, Lox75, Lox43, Lox44 (see, e.g., Hoess, R., et al., Nucl. Acids Res. 14 (1986) 2287-2300; Albert, H., et al., Plant J. 7 (1995) 649-659).

For example, if Cre-recombinase is used the sequence to be exchanged is defined by the position of the two LoxP sites in the genome as well as in the donor nucleic acid. These LoxP sites are recognized by the Cre-recombinase. Nothing more is required, i.e. no ATP etc.

The Cre/LoxP-system operates in different cell types, like mammals, plants, bacteria and yeast.

Targeted Integration Using Recombinases

In certain embodiments, the targeted integration is by a recombinase mediated cassette exchange reaction (RMCE).

RMCE is an enzymatic process wherein a sequence at the site of integration in the genome is exchanged for a donor nucleic acid. Any recombinase can be used for this process, such as Cre-recombinase, Flp-recombinase, Bxbl-integrase, pSRT-recombinase, or cφC31-integrase.

One specific TI method is double recombinase mediated cassette exchange (double RMCE).

Double RMCE is a method for producing a recombinant mammalian cell comprising a deoxyribonucleic acid encoding a proteinaceous compound of interest by recombinase-mediated introduction of two nucleic acid sequences into the host cell's genome at a single locus. After integration, the two nucleic acid sequences are operably linked to each other.

For example, but not by way of limitation, an integrated exogenous nucleotide sequence, i.e. the TI landing site, could comprise two recombination recognition sites (RRSs), while the (donor) nucleic acid sequence comprises two RRSs matching the RRSs on the integrated exogenous nucleotide sequence. Such single-plasmid RMCE strategies allow for the introduction of multiple open reading frames by incorporating the appropriate number of expression cassettes in the respective sequence between the pair of RRSs.

For example, but not by way of limitation, an integrated exogenous nucleotide sequence, i.e. the TI landing site, could comprise three recombination recognition sites (RRSs), e.g., an arrangement where the third RRS ("RRS3") is present between the first RRS ("RRS1") and the second RRS ("RRS2"), while a first (donor) nucleic acid comprises two RRSs matching the first and the third RRS on the integrated exogenous nucleotide sequence, and a second (donor) nucleic acid comprises two RRSs matching the third and the second RRS on the integrated exogenous nucleotide sequence. Such double RMCE strategy allows for the introduction of multiple genes by incorporation of the appropriate number of expression cassettes in the respective sequence between each pair of RRSs.

In addition, two selection markers are needed in the two-plasmid RMCE. One selection marker expression cassette is split into two parts. The first (front) nucleic acid could contain the promoter followed by the translation start codon and the RRS3 sequence. The second (back) nucleic acid correspondingly comprises the RRS3 sequence fused to the N-terminus of the selection marker coding sequence, minus the translation start codon (e.g. ATG). Additional nucleotides may need to be inserted between the RRS3 site and the selection marker coding sequence to ensure in frame translation from the fused gene, i.e. operable linkage. Only when both nucleic acids (front and back) are correctly inserted, the full expression cassette of the selection marker will be assembled and, thus, rendering cells resistance to the respective selection agent.

Both single and double RMCE allow for integration of one or more donor DNA molecule(s) into a pre-determined site of a mammalian cell's genome by precise exchange of a DNA sequence present on the donor DNA with a DNA sequence in the mammalian cell's genome where the integration site resides. These DNA sequences are characterized by two heterospecific RRSs flanking i) at least one selection marker or as in certain two-plasmid RMCEs a "split selection marker"; and/or ii) at least one exogenous gene of interest.

RMCE involves a recombinase-catalyzed, double recombination crossover event between the two heterospecific RRSs within the target genomic locus and the donor DNA molecule. Double RMCE is designed to introduce a copy of the DNA sequences from the front- and back-nucleic acid in combination into the pre-determined locus of a mammalian cell's genome. The RMCE procedure can be repeated with multiple DNA sequences.

In certain embodiments, targeted integration is achieved by double RMCE, wherein two different DNA sequences, each comprising at least one expression cassette encoding a part of a proteinaceous compound of interest and/or at least one selection marker or part thereof flanked by two heterospecific RRSs, are both integrated into a pre-determined site of the genome of a mammalian cell suitable for TI. In certain embodiments, targeted integration is achieved by multiple RMCEs, wherein DNA sequences from multiple nucleic acids, each comprising at least one expression cassette encoding a part of a proteinaceous compound of interest and/or at least one selection marker or part thereof flanked by two heterospecific RRSs, are all integrated into a predetermined site of the genome of a mammalian cell suitable for TI. In certain embodiments, the selection marker can be partially encoded on the first nucleic acid (front) and partially encoded on the second nucleic acid (back) such that only the correct integration of both nucleic acids by double RMCE allows for the expression of the selection marker.

For single RMCE and double RMCE the method for the targeted integration of a donor nucleic acid into the genome of a recipient/target cell as well as the method for the simultaneous targeted integration of two donor nucleic acids into the genome of a recipient/target cell as outlined above comprises the additional step of introducing/activating the recombinase.

Thus, in one embodiment, the recombination sequences are recombination recognition sequences and the method further comprises the following step:

c) introducing or activating
  - i) either simultaneously with the introduction of the deoxyribonucleic acid of b); or
  - ii) sequentially thereafter a recombinase, wherein the recombinases recognize the recombination recognition sequences of the first and the second deoxyribonucleic acid; (and optionally wherein the one or more recombinases perform a recombinase mediated cassette exchange).

In certain embodiments, a RRS is selected from the group consisting of a LoxP sequence, a L3 sequence, a 2L sequence, a LoxFas sequence, a Lox511 sequence, a Lox2272 sequence, a Lox2372 sequence, a Lox5171 sequence, a Loxm2 sequence, a Lox71 sequence, a Lox66 sequence, a FRT sequence, a F3 sequence, a F5 sequence, a Bxbl attP sequence, a Bxbl attB sequence, a φC31 attP sequence, and a φC31 attB sequence. If multiple RRSs have to be present, the selection of each of the sequences is dependent on the other insofar as non-identical RRSs are chosen.

In certain embodiments, a RRS can be recognized by a Cre-recombinase. In certain embodiments, a RRS can be recognized by an Flp-recombinase. In certain embodiments, a RRS can be recognized by a Bxbl-integrase. In certain embodiments, a RRS can be recognized by a φC31-integrase. In certain embodiments, a RRS can be recognized by a pSR1-recombinase.

In certain embodiments when the RRS is a LoxP site, the cell requires the Cre-recombinase to perform the recombination.

In certain embodiments when the RRS is a FRT site, the cell requires the Flp-recombinase to perform the recombination.

In certain embodiments when the RRS is a Bxbl attP or a Bxbl attB site, the cell requires the Bxbl-integrase to perform the recombination.

In certain embodiments when the RRS is a φC31 attP or a φC31 attB site, the cell requires the φC31-integrase to perform the recombination.

In certain embodiments when the RRS is a recognition site for the pSR1-recombinase of *Zygosaccharomyces rouxii*, the cell requires the pSR1-recombinase to perform the recombination.

Recombinase-encoding genes can be delivered into cells as DNA, by viral vectors, or as mRNA. Transfection of DNA or mRNA can be done by electroporation or cationic lipid-based reagents. Integrase-deficient lentiviral vectors can be used for delivering recombinases into transfection-resistant cell types. AAV vectors can also be used for recombinase delivery. Recombinase protein can also be introduced by means of nonovesicle.

In one embodiment of all aspects and embodiments, the recombinase is introduced as mRNA into the cell.

In one embodiment of all aspects and embodiments, the recombinase is introduced as DNA into the host cell. In one embodiment, the DNA is a recombinase encoding sequence comprised in an expression cassette.

In one embodiment of all aspects and embodiments, the recombinase is Cre-recombinase and the Cre-recombinase is introduced as Cre-recombinase encoding mRNA, which encodes a polypeptide that has the amino acid sequence of SEQ ID NO: 26, into the cell.

In one embodiment of all aspects and embodiments, the Cre-recombinase mRNA encodes a polypeptide comprising the amino acid sequence of SEQ ID NO: 26 and that further comprises at its N- or C-terminus or at both a nuclear localization sequence. In one embodiment, the Cre-recombinase mRNA encodes a polypeptide that has the amino acid sequence of SEQ ID NO: 26 and further comprises at its N- or C-terminus or at both independently of each other one to five nuclear localization sequences.

In one embodiment of all aspects and embodiments, the Cre-recombinase encoding mRNA comprises the nucleotide sequence of SEQ ID NO: 27 or a variant thereof with different codon usage. In one embodiment of all aspects and embodiments, the Cre-recombinase encoding mRNA comprises the nucleotide sequence of SEQ ID NO: 27 or a variant thereof with different codon usage and further comprises at its 5'- or 3'-end or at both a further nucleic acid encoding a nuclear localization sequence. In one embodiment of all aspects and embodiments, the Cre-recombinase encoding mRNA comprises the nucleotide sequence of SEQ ID NO: 27 or a variant thereof with different codon usage and further comprises at its 5'- or 3'-end or at both independently of each other one to five nucleic acids encoding nuclear localization sequences.

In certain embodiments, a LoxP sequence is a wild-type LoxP sequence. In certain embodiments, a LoxP sequence is a mutant LoxP sequence. Mutant LoxP sequences have been developed to increase the efficiency of Cre-recombinase-mediated integration or replacement. In certain embodiments, a mutant LoxP sequence is selected from the group consisting of a L3 sequence, a 2L sequence, a LoxFas sequence, a Lox511 sequence, a Lox2272 sequence, a Lox2372 sequence, a Lox5171 sequence, a Loxm2 sequence, a Lox71 sequence, and a Lox66 sequence. For example, the Lox71 sequence has 5 bp mutated in the left 13 bp repeat. The Lox66 sequence has 5 bp mutated in the right 13 bp repeat. Both the wild-type and the mutant LoxP sequences can mediate Cre-recombinase-dependent recombination.

The term "matching RRSs" indicates that a recombination occurs between the two matching RRSs. In certain embodiments, the two matching RRSs are the same. In certain embodiments, both RRSs are wild-type LoxP sequences. In certain embodiments, both RRSs are mutant LoxP sequences. In certain embodiments, both RRSs are wild-type FRT sequences. In certain embodiments, both RRSs are mutant FRT sequences. In certain embodiments, the two matching RRSs are different sequences but can be recognized by the same recombinase. In certain embodiments, the first matching RRS is a Lox71 sequence and the second matching RRS is a Lox66 sequence. In certain embodiments, the first matching RRS is a Bxbl attP sequence and the second matching RRS is a Bxbl attB sequence. In certain embodiments, the first matching RRS is a (φC31 attB sequence and the second matching RRS is a (φC31 attB sequence.

In one embodiment of all aspects and embodiments, the recombination recognition sites in the double RMCE are L3, 2L and LoxFas. In one embodiment, L3 comprises as spacer sequence the sequence of SEQ ID NO: 04, 2L comprises as spacer sequence the sequence of SEQ ID NO: 05 and LoxFas comprises as spacer sequence has the sequence of SEQ ID NO: 06. In one embodiment the first recombination recognition site is L3, the second recombination recognition site is 2L and the third recombination recognition site is LoxFas.

In one embodiment of all aspects and embodiments, the expression cassette encoding for a selection marker is located partly 5' and partly 3' to the third recombination recognition site, wherein the 5'-located part of said expression cassette comprises the promoter and a translation start-codon and the 3'-located part of said expression cassette comprises the coding sequence without a translation start-codon and a polyA signal sequence.

In one embodiment of all aspects and embodiments, the 5'-located part of the expression cassette encoding the selection marker comprises a promoter sequence operably linked to a translation start-codon, whereby the promoter sequence is flanked upstream by (i.e. is positioned downstream to) the second, third or fourth, respectively, expression cassette and the start-codon is flanked downstream by (i.e. is positioned upstream of) the third recombination recognition sequence; and the 3'-located part of the expression cassette encoding the selection marker comprises a nucleic acid encoding the selection marker lacking a translation start-codon and is flanked upstream by the third recombination recognition sequence and downstream by a polyA signal sequence and thereafter by the third, fourth, or fifth, respectively, expression cassette.

Any known or future mammalian cell suitable for targeted integration comprising an exogenous nucleic acid ("landing site") as described herein can be used in the current invention.

In one preferred embodiment of all aspects and embodiments, the mammalian cell comprising an exogenous nucleotide sequence integrated at a single site within a locus of the genome of the mammalian cell is a hamster cell or a human cell, in one embodiment a CHO cell.

An exemplary mammalian cell comprising an exogenous nucleotide sequence integrated at a single site within a locus of its genome that is suitable for use in the current invention is a CHO cell or a HEK293 cell or a Per.C6 cell harboring a landing site (=exogenous nucleotide sequence integrated at a single site within a locus of the genome of the mammalian cell) comprising three heterospecific LoxP sites for Cre-recombinase mediated cassette exchange. These heterospecific LoxP sites are, in one embodiment, L3, LoxFas and 2L (see e.g. Lanza et al., Biotechnol. J. 7 (2012) 898-908; Wong et al., Nucleic Acids Res. 33 (2005) e147), whereby L3 and 2L flank the landing site at the 5'-end and 3'-end, respectively, or vice versa, and LoxFas is located between the L3 and 2L sites. In certain embodiments of all aspects and embodiments, the landing site further contains a bicistronic unit linking the expression of a selection marker via an IRES to the expression of green fluorescent protein (GFP) allowing to stabilize the landing site by positive selection as well as to select for the absence of the site after transfection and Cre-recombinase-mediated recombination (negative selection). An exemplary GFP has the sequence of SEQ ID NO: 28.

Such a configuration of the landing site as outlined in the previous paragraphs allows for the simultaneous integration of two nucleic acids comprised in different plasmids, a so called front nucleic acid with an L3 and a LoxFas site and a back nucleic acid harboring a LoxFas and an 2L site. The functional elements of a selection marker gene different from that present in the landing site are distributed between both nucleic acids: promoter and translation start codon are located on the front nucleic acid whereas coding region and poly A signal are located on the back nucleic acid. Only correct Cre-recombinase-mediated integration of both said nucleic acids induces resistance against the respective selection agent.

Generally, a mammalian cell suitable for TI is a mammalian cell comprising an exogenous nucleotide sequence integrated within a locus of its genome, wherein the exogenous nucleotide sequence comprises a first and a second recombination recognition site flanking at least one first selection marker, and a third recombination recognition site located between the first and the second recombination recognition site, and all the recombination recognition sites are different. Said exogenous nucleotide sequence is called a "landing site".

The presently disclosed subject matter uses a mammalian cell suitable for TI of exogenous nucleotide sequences. In certain embodiments, the mammalian cell suitable for TI comprises an exogenous nucleotide sequence integrated at an integration site in the genome of the mammalian cell. Such a mammalian cell suitable for TI can be denoted also as a "TI host cell".

In certain embodiments of all aspects and embodiments, the mammalian cell suitable for TI is a hamster cell, a human cell, a rat cell, or a mouse cell comprising a landing site. In certain embodiments, the mammalian cell suitable for TI is a Chinese hamster ovary (CHO) cell, a CHO K1 cell, a CHO K1SV cell, a CHO DG44 cell, a CHO DUKXB-11 cell, a CHO K1S cell, a CHO KIM cell, a human cell, a HEK293 cell, or a Per.C6 cell comprising a respective landing site.

In certain embodiments of all aspects and embodiments, a mammalian cell suitable for TI comprises an integrated exogenous nucleotide sequence, wherein the exogenous nucleotide sequence comprises one or more recombination recognition sites (RRS). In certain embodiments, the exogenous nucleotide sequence comprises at least two RRSs. The RRS can be recognized by a recombinase, for example, a Cre-recombinase, an Flp-recombinase, a Bxbl-integrase, or a φC31-integrase. The RRS can be selected from the group consisting of a LoxP site, a L3 site, a 2L site, a LoxFas site, a Lox511 site, a Lox2272 site, a Lox2372 site, a Lox5171 site, a Loxm2 site, a Lox71 site, a Lox66 site, a FRT site, a F3 site, a F5 site, a Bxbl attP site, a Bxbl attB site, a φC31 attP site, and a φC31 attB site.

In one embodiment of all aspects and embodiments, the selection marker is independently of each other selected from the group consisting of an aminoglycoside phosphotransferase (APH) (e.g., hygromycin phosphotransferase (HYG), neomycin and G418 APH), dihydrofolate reductase (DHFR), thymidine kinase (TK), glutamine synthetase (GS), asparagine synthetase, tryptophan synthetase (indole), histidinol dehydrogenase (histidinol D), and genes encoding resistance to puromycin, blasticidin, bleomycin, phleomycin, chloramphenicol, Zeocin, and mycophenolic acid. The selection marker(s) can also be a fluorescent protein selected from the group consisting of green fluorescent protein (GFP), enhanced GFP (eGFP), a synthetic GFP, yellow fluorescent protein (YFP), enhanced YFP (eYFP), cyan fluorescent protein (CFP), mPlum, mCherry, tdTomato, mStrawberry, J-red, DsRed-monomer, mOrange, mKO, mCitrine, Venus, YPet, Emerald6, CyPet, mCFPm, Cerulean, and T-Sapphire.

An exogenous nucleotide sequence is a nucleotide sequence that does not originate from a specific cell but can be introduced into said cell by DNA delivery methods, such as, e.g., by transfection, transduction, electroporation, or transformation methods. In certain embodiments of all aspects and embodiments, a mammalian cell suitable for TI comprises at least one exogenous nucleotide sequence integrated at a more integration site in the mammalian cell's genome. In certain embodiments, the exogenous nucleotide sequence is integrated at an integration sites within a specific a locus of the genome of the mammalian cell.

In certain embodiments of all aspects and embodiments, an integrated exogenous nucleotide sequence comprises one or more recombination recognition sites (RRS), wherein the RRS can be recognized by a recombinase. In certain embodiments, the integrated exogenous nucleotide sequence comprises at least two RRSs. In certain embodiments, an integrated exogenous nucleotide sequence comprises three RRSs, wherein the third RRS is located between the first and the second RRS. In certain embodiments, the first and the second RRS are the same and the third RRS is different from the first or the second RRS. In certain embodiments, all three RRSs are different. In certain embodiments, the RRSs are selected independently of each other from the group consisting of a LoxP site, a L3 site, a 2L site, a LoxFas site, a Lox511 site, a Lox2272 site, a Lox2372 site, a Lox5171 site, a Loxm2 site, a Lox71 site, a Lox66 site, a FRT site, a F3 site, a F5 site, a Bxbl attP site, a Bxbl attB site, a φC31 attP site, and a φC31 attB site.

In certain embodiments of all aspects and embodiments, the integrated exogenous nucleotide sequence comprises at least one selection marker. In certain embodiments, the integrated exogenous nucleotide sequence comprises a first, a second and a third RRS, and at least one selection marker. In certain embodiments, a selection marker is located between the first and the second RRS. In certain embodiments, two RRSs flank at least one selection marker, i.e., a first RRS is located 5' (upstream) and a second RRS is located 3' (downstream) of the selection marker. In certain embodiments, a first RRS is adjacent to the 5'-end of the selection marker and a second RRS is adjacent to the 3'-end of the selection marker.

In certain embodiments of all aspects and embodiments, a selection marker is located between a first and a second RRS and the two flanking RRSs are different. In certain embodiments, the first flanking RRS is a L3 sequence and the second flanking RRS is a 2L sequence. In certain embodiments, a L3 sequenced is located 5' of the selection marker and a 2L sequence is located 3' of the selection marker.

In certain embodiments of all aspects and embodiments, the first flanking RRS is a LoxP sequence with wild-type inverted repeats and the second flanking RRS is a LoxP sequence with one mutated inverted repeat. In certain embodiments, the first flanking RRS is a LoxP sequence with a first mutated inverted repeat and the second flanking RRS is a LoxP sequence with a second mutated inverted repeat that is the same or different from the first mutated inverted repeat. In certain embodiments, the first flanking RRS is a LoxP sequence with wild-type inverted repeats and the third RRS is a LoxP sequence with one mutated inverted repeat. In certain embodiments, the second flanking RRS is a LoxP sequence with wild-type inverted repeats and the third RRS is a LoxP sequence with one mutated inverted repeat. In certain embodiments, the first flanking RRS is a LoxP sequence with a first mutated inverted repeat and the third RRS is a LoxP sequence with a second mutated inverted repeat.

In certain embodiments of all aspects and embodiments, the second flanking RRS is a LoxP sequence with a first mutated inverted repeat and the third RRS is a LoxP sequence with a second mutated inverted repeat.

In certain embodiments of all aspects and embodiments, the first flanking RRS is a wild-type FRT sequence and the second flanking RRS is a mutant FRT sequence. In certain embodiments, the first flanking RRS is a first mutant FRT sequence and the second flanking RRS is a second mutant FRT sequence.

In certain embodiments of all aspects and embodiments, the first flanking RRS is a Bxbl attP sequence and the second flanking RRS is a Bxbl attB sequence.

In certain embodiments of all aspects and embodiments, the first flanking RRS is a φC31 attP sequence and the second flanking RRS is a φC31 attB sequence.

In certain embodiments of all aspects and embodiments, the integrated exogenous nucleotide sequence comprises a first and a second selection marker, which are flanked by two RRSs, wherein the first selection marker is different from the second selection marker. In certain embodiments, the two selection markers are both independently of each other selected from the group consisting of a glutamine synthetase selection marker, a thymidine kinase selection marker, a HYG selection marker, and a puromycin resistance selection marker. In certain embodiments, the integrated exogenous nucleotide sequence comprises a thymidine kinase selection marker and a HYG selection marker. In certain embodiments, the first selection maker is selected from the group consisting of an aminoglycoside phosphotransferase (APH) (e.g., hygromycin phosphotransferase (HYG), neomycin and G418 APH), dihydrofolate reductase (DHFR), thymidine kinase (TK), glutamine synthetase (GS), asparagine synthetase, tryptophan synthetase (indole), histidinol dehydrogenase (histidinol D), and genes encoding resistance to puromycin, blasticidin, bleomycin, phleomycin, chloramphenicol, Zeocin, and mycophenolic acid, and the second selection maker is selected from the group consisting of a GFP, an eGFP, a synthetic GFP, a YFP, an eYFP, a CFP, an mPlum, an mCherry, a tdTomato, an mStrawberry, a J-red, a DsRed-monomer, an mOrange, an mKO, an mCitrine, a Venus, a YPet, an Emerald, a CyPet, an mCFPm, a Cerulean, and a T-Sapphire fluorescent protein. In certain embodiments, the first selection marker is a glutamine synthetase selection marker and the second selection marker is a GFP fluorescent protein. In certain embodiments, the two RRSs flanking both selection markers are different.

In certain embodiments of all aspects and embodiments, the selection marker is operably linked to a promoter sequence. In certain embodiments, the selection marker is operably linked to an SV40 promoter. In certain embodiments, the selection marker is operably linked to a human Cytomegalovirus (CMV) promoter.

Independent of the method used for the introduction of the donor deoxyribonucleic acid, successfully transfected cells can be selected based on the introduced second selection marker.

It has to be pointed out that when the DNA element, the DNA molecule, or the VA RNA nucleic acid according to the current invention is used in combination with recombinase-mediated cassette exchange reactions, different recombinases are used for the RMCE and the RMCI.

For example, the Cre/LoxP-system is used for the recombinase-mediated cassette exchange reaction (RMCE) and the Flp/FRT-system is used for the recombinase-mediated cassette inversion (RMCI) in the DNA element, the DNA molecule, or the VA RNA according to the current invention. Likewise, the Flp/FRT-system is used for the recombinase-mediated cassette exchange reaction (RMCE) and the Cre/LoxP-system is used for the recombinase-mediated cassette inversion (RMCI) in the DNA element, the DNA molecule, or the VA RNA according to the current invention.

Adeno-Associated Viral Vectors

For a general review of AAVs and of the adenovirus or herpes helper functions see, Bems and Bohensky, Advances in Virus Research, Academic Press., 32 (1987) 243-306. The genome of AAV is described in Srivastava et al., J. Virol., 45 (1983) 555-564. In U.S. Pat. No. 4,797,368 design considerations for constructing recombinant AAV vectors are described (see also WO 93/24641). Additional references describing AAV vectors are West et al., Virol. 160 (1987) 38-47; Kotin, Hum. Gene Ther. 5 (1994) 793-801; and Muzyczka J. Clin. Invest. 94 (1994) 1351. Construction of recombinant AAV vectors described in U.S. Pat. No. 5,173,414; Lebkowski et al., Mol. Cell. Biol. 8 (1988) 3988-3996; Tratschin et al., Mol. Cell. Biol. 5 (1985) 3251-3260; Tratschin et al., Mol. Cell. Biol., 4 (1994) 2072-2081; Hermonat and Muzyczka Proc. Natl. Acad. Sci. USA 81 (1984) 6466-6470; Samulski et al. J. Virol. 63 (1989) 3822-3828.

An adeno-associated virus (AAV) is a replication-deficient parvovirus. It can replicate only in cells, in which certain viral functions are provided by a co-infecting helper virus, such as adenoviruses, herpesviruses and, in some cases, poxviruses such as vaccinia. Nevertheless, an AAV can replicate in virtually any cell line of human, simian or rodent origin provided that the appropriate helper viral functions are present.

Without helper viral genes being present, an AAV establishes latency in its host cell. Its genome integrates into a specific site in chromosome 19 [(Chr) 19 (q13.4)], which is termed the adeno-associated virus integration site 1 (AAVS1). For specific serotypes, such as AAV-2 other integration sites have been found, such as, e.g., on chromosome 5 [(Chr) 5 (p13.3)], termed AAVS2, and on chromosome 3 [(Chr) 3 (p24.3)], termed AAVS3.

AAVs are categorized into different serotypes. These have been allocated based on parameters, such as hemagglutination, tumorigenicity and DNA sequence homology. Up to now, more than 10 different serotypes and more than a hundred sequences corresponding to different clades of AAV have been identified.

The capsid protein type and symmetry determines the tissue tropism of the respective AAV. For example, AAV-2, AAV-4 and AAV-5 are specific to retina, AAV-2, AAV-5, AAV-8, AAV-9 and AAVrh-10 are specific for brain, AAV-1, AAV-2, AAV-6, AAV-8 and AAV-9 are specific for cardiac tissue, AAV-1, AAV-2, AAV-5, AAV-6, AAV-7, AAV-8, AAV-9 and AAV-10 are specific for liver, AAV-1, AAV-2, AAV-5 and AAV-9 are specific for lung.

Pseudotyping denotes a process comprising the cross packaging of the AAV genome between various serotypes, i.e. the genome is packaged with differently originating capsid proteins.

The wild-type AAV genome has a size of about 4.7 kb. The AAV genome further comprises two overlapping genes named rep and cap, which comprise multiple open reading frames (see, e.g., Srivastava et al., J. Viral., 45 (1983) 555-564; Hermonat et al., J. Viral. 51 (1984) 329-339; Tratschin et al., J. Virol., 51 (1984) 611-619). The Rep protein encoding open reading frame provides for four proteins of different size, which are termed Rep78, Rep68, Rep52 and Rep40. These are involved in replication, rescue and integration of the AAV. The Cap protein encoding open reading frame provides four proteins, which are termed VP1, VP2, VP3, and AAP. VP1, VP2 and VP3 are part of the proteinaceous capsid of the AAV particles. The combined rep and cap open reading frames are flanked at their 5'- and 3'-ends by so-called inverted terminal repeats (ITRs). For replication, an AAV requires in addition to the Rep and Cap proteins the products of the genes E1A, E1B, E4orf6, E2A and VA of an adenovirus or corresponding factors of another helper virus.

In the case of an AAV of the serotype 2 (AAV-2), for example, the ITRs each have a length of 145 nucleotides and flank a coding sequence region of about 4470 nucleotides. Of the ITR's 145 nucleotides 125 nucleotides have a palindromic sequence and can form a T-shaped hairpin structure. This structure has the function of a primer during viral replication. The remaining 20, non-paired, nucleotides are denoted as D-sequence.

The AAV genome, harbors three transcription promoters P5, P19, and P40 (Laughlin et al., Proc. Natl. Acad. Sci. USA 76 (1979) 5567-5571) for the expression of the rep and cap genes.

The ITR sequences have to be present in cis to the coding region. The ITRs provide a functional origin of replication (ori), signals required for integration into the target cell's genome, and efficient excision and rescue from host cell chromosomes or recombinant plasmids. The ITRs further comprise origin of replication like-elements, such as a Rep-protein binding site (RBS) and a terminal resolution site (TRS). It has been found that the ITRs themselves can have the function of a transcription promoter in an AAV vector (Flotte et al., J. Biol. Chem. 268 (1993) 3781-3790; Flotte et al., Proc. Natl. Acad. Sci. USA 93 (1993) 10163-10167).

For replication and encapsidation, respectively, of the viral single-stranded DNA genome an in trans organization of the rep and cap gene products are required.

The rep gene locus comprises two internal promoters, termed P5 and P19. It comprises open reading frames for four proteins. Promoter P5 is operably linked to a nucleic acid sequence providing for non-spliced 4.2 kb mRNA encoding the Rep protein Rep78 (chromatin nickase to arrest cell cycle), and a spliced 3.9 kb mRNA encoding the Rep protein Rep68 (site-specific endonuclease). Promoter P19 is operably linked to a nucleic acid sequence providing for a non-spliced mRNA encoding the Rep protein Rep52 and a spliced 3.3 kb mRNA encoding the Rep protein Rep40 (DNA helicases for accumulation and packaging).

The two larger Rep proteins, Rep78 and Rep68, are essential for AAV duplex DNA replication, whereas the smaller Rep proteins, Rep52 and Rep40, seem to be essential for progeny, single-strand DNA accumulation (Chejanovsky & Carter, Virology 173 (1989) 120-128).

The larger Rep proteins, Rep68 and Rep78, can specifically bind to the hairpin conformation of the AAV ITR. They exhibit defined enzyme activities, which are required for resolving replication at the AAV termini. Expression of Rep78 or Rep68 could be sufficient for infectious particle formation (Holscher, C., et al. J. Virol. 68 (1994) 7169-7177 and 69 (1995) 6880-6885).

It is deemed that all Rep proteins, primarily Rep78 and Rep68, exhibit regulatory activities, such as induction and suppression of AAV genes as well as inhibitory effects on cell growth (Tratschin et al., Mol. Cell. Biol. 6 (1986) 2884-2894; Labow et al., Mol. Cell. Biol., 7 (1987) 1320-1325; Khleif et al., Virology, 181 (1991) 738-741).

Recombinant overexpression of Rep78 results in phenotype with reduced cell growth due to the induction of DNA damage. Thereby the host cell is arrested in the S phase, whereby latent infection by the virus is facilitated (Berthet, C., et al., Proc. Natl. Acad. Sci. USA 102 (2005) 13634-13639).

Tratschin et al. reported that the P5 promoter is negatively auto-regulated by Rep78 or Rep68 (Tratschin et al., Mol. Cell. Biol. 6 (1986) 2884-2894). Due to the toxic effects of expression of the Rep protein, only very low expression has been reported for certain cell lines after stable integration of AAV (see, e.g., Mendelson et al., Virol. 166 (1988) 154-165).

The cap gene locus comprises one promoter, termed P40. Promoter P40 is operably linked to a nucleic acid sequence providing for 2.6 kb mRNA, which, by alternative splicing and use of alternative start codons, encodes the Cap proteins VP1 (87 kDa, non-spliced mRNA transcript), VP2 (72 kDa, from the spliced mRNA transcript), and VP3 (61 kDa, from alternative start codon). VP1 to VP3 constitute the building blocks of the viral capsid. The capsid has the function to bind to a cell surface receptor and allow for intracellular trafficking of the virus. VP3 accounts for about 90% of total viral particle protein. Nevertheless, all three proteins are essential for effective capsid production.

It has been reported that inactivation of all three capsid proteins VP1 to VP3 prevents accumulation of single-strand progeny AAV DNA. Mutations in the VP1 amino-terminus (“Lip-negative” or “Inf-negative”) still allows for assembly of single-stranded DNA into viral particles whereby the infectious titer is greatly reduced.

The AAP open reading frame is encoding the assembly activating protein (AAP). It has a size of about 22 kDa and transports the native VP proteins into the nucleolar region for capsid assembly. This open reading frame is located upstream of the VP3 protein encoding sequence.

In individual AAV particles, only one single-stranded DNA molecule is contained. This may be either the “plus” or “minus” strand. AAV viral particles containing a DNA molecule are infectious. Inside the infected cell, the parental infecting single strand is converted into a double strand, which is subsequently amplified. The amplification results in a large pool of double stranded DNA molecules from which single strands are displaced and packaged into capsids.

Adeno-associated viral (AAV) vectors can transduce dividing cells as well as resting cells. It can be assumed that a transgene introduced using an AAV vector into a target cell will be expressed for a long period. One drawback of using an AAV vector is the limitation of the size of the transgene that can be introduced into cells.

Carter et al. have shown that the entire rep and cap open reading frames can be deleted and replaced with a transgene (Carter, B. J., in “Handbook of Parvoviruses”, ed. by P. Tijssen, CRC Press, pp. 155-168 (1990)). Further, it has been reported that the ITRs have to be maintained to retain the function of replication, rescue, packaging, and integration of the transgene into the genome of the target cell.

When cells comprising the respective viral helper genes are transduced by an AAV vector, or, vice versa, when cells comprising an integrated AAV provirus are transduced by a suitable helper virus, then the AAV provirus is activated and enters a lytic infection cycle again (Clark, K. R., et al., Hum. Gene Ther. 6 (1995) 1329-1341; Samulski, R. J., Curr. Opin. Genet. Dev. 3 (1993) 74-80).

E1A is the first viral helper gene that is expressed after adenoviral DNA enters the cell nucleus. The E1A gene encodes the 12S and 13S proteins, which are based on the same E1A mRNA by alternative splicing. Expression of the 12S and 13S proteins results in the activation of the other viral functions E1B, E2, E3 and E4. Additionally, expression of the 12S and 13S proteins force the cell into the S phase of the cell cycle. If only the ETA-derived proteins are expressed, the cell will dye (apoptosis).

E1B is the second viral helper gene that is expressed. It is activated by the E1A-derived proteins 12S and 135. The E1B gene derived mRNA can be spliced in two different ways resulting in a first 55 kDa transcript and a second 19 kDa transcript.

The E1B 55 kDa protein is involved in the modulation of the cell cycle, the prevention of the transport of cellular mRNA in the late phase of the infection, and the prevention of ETA-induced apoptosis. The E1B 19 kDa protein is involved in the prevention of ETA-induced apoptosis of cells.

The E2 gene encodes different proteins. The E2A transcript codes for the single strand-binding protein (SSBP), which is essential for AAV replication Also the E4 gene encodes several proteins. The E4 gene derived 34 kDa protein (E4orf6) prevents the accumulation of cellular mRNAs in the cytoplasm together with the E1B 55 kDa protein, but also promotes the transport of viral RNAs from the cell nucleus into the cytoplasm.

Generally, to produce recombinant AAV particles, different, complementing plasmids are co-transfected into a host cell. One of the plasmids comprises the transgene sandwiched between the two cis acting AAV ITRs. The missing AAV elements required for replication and subsequent packaging of progeny recombinant genomes, i.e. the open reading frames for the Rep and Cap proteins, are contained in trans on a second plasmid. The overexpression of the Rep proteins results in inhibitory effects on cell growth (Li, J., et al., J. Virol. 71 (1997) 5236-5243). Additionally, a third plasmid comprising the genes of a helper virus, i.e. E1, E4orf6, E2A and VA from adenovirus, is required for AAV replication.

To reduce the number of required plasmids, Rep, Cap and the adenovirus helper genes may be combined on a single plasmid.

Alternatively, the host cell may already stably express the E1 gene products. Such a cell is a HEK293 cell. The human embryonic kidney clone denoted as 293 was generated back in 1977 by integrating adenoviral DNA into human embryonic kidney cells (HEK cells) (Graham, F. L., et al., J. Gen. Virol. 36 (1977) 59-74). The HEK293 cell line comprises base pair 1 to 4344 of the adenovirus serotype 5 genome. This encompasses the E1A and E1B genes as well as the adenoviral packaging signals (Louis, N., et al., Virology 233 (1997) 423-429).

When using HEK293 cells the missing E2A, E4orf6 and VA genes can be introduced either by co-infection with an adenovirus or by co-transfection with an E2A-, E4orf6- and VA-expressing plasmid (see, e.g., Samulski, R. J., et al., J.

Virol. 63 (1989) 3822-3828; Allen, J. M., et al., J. Virol. 71 (1997) 6816-6822; Tamayose, K., et al., Hum. Gene Ther. 7 (1996) 507-513; Flotte, T. R., et al., Gene Ther. 2 (1995) 29-37; Conway, J. E., et al., J. Virol. 71 (1997) 8780-8789; Chiorini, J. A., et al., Hum. Gene Ther. 6 (1995) 1531-1541; Ferrari, F. K., et al., J. Virol. 70 (1996) 3227-3234; Salvetti, A., et al., Hum. Gene Ther. 9 (1998) 695-706; Xiao, X., et al., J. Virol. 72 (1998) 2224-2232; Grimm, D., et al., Hum. Gene Ther. 9 (1998) 2745-2760; Zhang, X., et al., Hum. Gene Ther. 10 (1999) 2527-2537). Alternatively, adenovirus/AAV or herpes simplex virus/AAV hybrid vectors can be used (see, e.g., Conway, J. E., et al., J. Virol. 71 (1997) 8780-8789; Johnston, K. M., et al., Hum. Gene Ther. 8 (1997) 359-370; Thrasher, A. J., et al., Gene Ther. 2 (1995) 481-485; Fisher, J. K., et al., Hum. Gene Ther. 7 (1996) 2079-2087; Johnston, K. M., et al., Hum. Gene Ther. 8 (1997) 359-370).

Thus, cell lines in which the rep gene is integrated and expressed tend to grow slowly or express Rep proteins at very low levels.

A big safety issue is the contamination of the rAAV particle preparation by replication-competent adenoviruses (RCA). RCAs are produced when the vector genome and the adenoviral DNA integrated into the host cell recombine during viral replication by homologous recombination (Lochmueller, H., et al., Hum. Gene Ther. 5 (1994) 1485-1491; Hehir K. M., et al., J. Virol. 70 (1996) 8459-8467). Therefore, HEK 293 cells are not suitable for producing adenoviral vectors for pharmaceutical application.

In order to limit the transgene activity to specific tissues, i.e. to limit the site of integration the transgene can be operably linked to an inducible or tissue specific promoter (see, e.g., Yang, Y., et al. Hum. Gene. Ther. 6 (1995) 1203-1213).

Until today, the main difficulty in the production of rAAV particles is the inefficient packaging of the rAAV vector, resulting in low titers. Packaging has been difficult for several reasons including

- preferred encapsidation of wild-type AAV genomes if they are present;
- difficulty in generating sufficient complementing functions such as those provided by the wild-type rep and cap genes due to the inhibitory effect associated with the rep gene products;
- the limited efficiency of the co-transfection of the plasmid constructs.

All these problems are based on the biological properties of the Rep proteins. Especially the inhibitory (cytostatic and cytotoxic) properties of the Rep proteins as well as the ability to reverse the immortalized phenotype of cultured cells is problematic. Additionally, Rep proteins down-regulate their own expression when the widely used AAV P5 promoter is employed (see, e.g., Tratschin et al., Mol. Cell. Biol. 6 (1986) 2884-2894).

Exemplary Compounds and Compositions According to the Current Invention

Herein are reported novel nucleic acids and methods of using the same. The novel nucleic acids according to the current invention are useful in the production of recombinant adeno-associated virus particles.

Thus, one aspect of the current invention is a novel adenoviral VA RNA nucleic acid. In the VA RNA nucleic acid according to the current invention, the VA RNA coding sequence comprises at its 5'-terminus or is linked at its 5'-terminus to a variant type 2 polymerase III promoter, or a type 3 polymerase III promoter, or a variant type 3 polymerase III promoter, such as, e.g., in one preferred embodiment the U6-snRNA promoter, or a polymerase II promoter. In certain embodiments, the VA RNA nucleic acid further comprises a precise transcription start site located 3' to the promoter and 5' to the VA RNA coding sequence. In certain embodiments, the VA RNA nucleic acid further comprises a polymerase III terminator at its 3'-terminus. In certain embodiments, the precise transcription start site comprises in 5'- to 3'-direction at least the six 5'-terminal nucleotides of an adenoviral VA RNAI gene comprising the transcription start site (TSS) (to prevent by-passing of the subsequent polymerase III (poly III) terminator) and a functional polymerase III terminator (to prevent transcription from the constitutively active upstream promoter). In certain embodiments of all aspects and embodiments, all elements in/of the adenoviral VA RNA nucleic acid according to the invention are arranged in an operably linked form.

To further increase the advantageous effects of the adenoviral VA RNA nucleic acid according to the current invention the employed promoter can be chosen to be activatable too, especially in the case of a polymerase II promoter. Thus, the transcription of the VA RNA coding sequence can be turned on only by further specific promoter activation. This results on the one hand in an improved control of the transcription of the VA RNA coding sequence and on the other hand in the possibility to turn the transcription off again. By the combination of the adenoviral VA RNA nucleic acid according to the current invention with an inducible promoter, potential leakiness of the inducible promoter when used in isolation can be further tightened. Inducible systems are known in the art, such as the Tet-on/off-system.

The presently disclosed subject matter not only provides methods for nucleic acids suitable for producing recombinant mammalian rAAV packaging or producing cell lines, optionally with inducible transcription of the VA RNA, but also for stable large-scale production of rAAV particle as well. Likewise, recombinant stable mammalian rAAV production cells that have high productivity of rAAV particles can be obtained.

Thus, in certain embodiments of all aspects and embodiments, the promoter is an inducible promoter. In certain embodiments, the inducible promoter is selected from the group of inducible promoters consisting of a tetracycline-controlled promoter, a cumate-controlled promoter, an FKBP12-mTOR-controlled promoter, a rapamycin-controlled promoter, an FKCsA-controlled promoter, an abscisic acid-controlled promoter, a tamoxifen-controlled promoter, and a riboswitch-controlled promoter (FKCsA=heterodimer of FK506 and cyclosporine A).

For a review of inducible promoters see, e.g., Kallunki, T., et al., Cells 8 (2019) 796.

In certain embodiments of all aspects and embodiments, the promoter is a repressible promoter. In certain embodiments, the repressible promoter is selected from the group of repressible promoters comprising a tetracycline-controlled promoter, a GAL4/UAS-controlled promoter, and a LexA/lexAop-controlled promoter.

Recombinant AAV Particles

For the generation of recombinant AAV particles, expression of the Rep and Cap proteins, the helper proteins ETA, E1B, E2A and E4orf6, as well as the adenoviral VA RNA in a single mammalian cell is required. The helper proteins ETA, E1B, E2A and E4orf6 can be expressed using any promoter as shown by Matsushita et al. (Gene Ther. 5 (1998) 938-945), especially the CMV IE promoter. Thus, in the following any promoter can be used.

DNA According to the Invention Comprising E1A, E1B, E2A, E4orf6 Open Reading Frames One independent aspect of the invention is a DNA (molecule) comprising an adenoviral VA RNA nucleic acid according to the current invention, a first DNA element, and optionally a rep or/and cap open reading frame.

In one dependent embodiment the first DNA element comprises an E1A open reading frame and an E1B open reading frame; or the first DNA element comprises an E2A open reading frame and an E4 or E4orf6 open reading frame; or the first DNA element comprises a Rep protein open reading frame and a Cap protein open reading frame.

One independent aspect of the current invention is a mammalian or insect cell comprising an adenoviral VA RNA nucleic acid or a DNA (element) according to the current invention.

One independent aspect according to the current invention is a method for producing recombinant adeno-associated virus (rAAV) particles comprising the following steps:

cultivating/propagating a cell according to the current invention (under conditions suitable for cell division), and recovering the rAAV particles from the cells or the cultivation medium.

Thus, one independent aspect of the current invention is an adenoviral VA RNA nucleic acid or a DNA (molecule) according to the current invention for the production of recombinant adeno-associated virus particles.

One independent aspect of the invention is a method of generating/for producing recombinant adeno-associated virus (rAAV) particle, the method comprising:

providing a mammalian, in suspension growing cell, which comprises either stably integrated or transiently present a transgene expression cassette interspaced between two AAV ITRs;

open reading frames encoding adenoviral E1A, E1B, E2A, E4 or E4orf6 proteins and an adenoviral VA RNA nucleic acid according to the current invention;

open reading frames encoding adeno-associated Rep and Cap proteins;

propagating/cultivating the mammalian cell (under conditions suitable for cell division); and isolating the rAAV particles from the cell or the cultivation medium and thereby producing the rAAV particles.

In certain embodiments of all aspects and embodiments, each open reading frame is within an expression cassette, i.e. operably linked to a promoter and a polyadenylation signal sequence and/or transcription termination element.

The coding sequences of E1A and E1B (open reading frames) are in certain embodiments of all aspects and embodiments derived from a human adenovirus, such as, e.g., in particular of human adenovirus serotype 2 or 5. An exemplary sequence of human Ad5 (adenovirus serotype 5) can be found in GenBank entry X02996 and that of human Ad2 can be found in GenBank entry AC_000007. In certain embodiments of all aspects and embodiments, nucleotides 505 to 3522 comprise the nucleic acid sequences encoding E1A and E1B of human adenovirus serotype 5. Plasmid pSTK146 as reported in EP 1 230 354 B1, as well as plasmids pGS119 and pGS122 as reported in WO 2007/056994, can also be used a source for the E1A and E1B open reading frames.

DNA According to the Invention Comprising Rep and Cap Open Reading Frames

Except for the P5 promoter, the promoters, which are driving the rep and cap open reading frame expression are located within the Rep-polypeptide coding sequence.

One independent aspect of the invention is a DNA (molecule) comprising an adenoviral VA RNA nucleic acid according to the current invention, a first DNA element, and optionally one or more or all of an ETA, E1B, E2, E4 and E4orf6 reading frame.

In certain embodiments of all aspects and embodiments, the first DNA element comprises a rep open reading frame or/and a cap open reading frame.

In certain embodiments of all aspects and embodiments, the first DNA element comprises one, two, three or four different Rep protein encoding open reading frames.

In certain embodiments of all aspects and embodiments, the first DNA element comprises one rep open reading frame comprising a coding sequence, which encodes either exclusively the Rep78 protein or exclusively the Rep68 protein, but not both, wherein the internal P40 promoter has been inactivated and splice donor as well as acceptor sites have been removed.

In certain embodiments of all aspects and embodiments, the rep open reading frame is operably linked at its 5'-terminus to the adeno-associated viral promoter P5 or a functional fragment thereof or a variant thereof.

In certain embodiments of all aspects and embodiments, the first DNA element comprises two rep open reading frames, wherein the first rep open reading frame comprises a coding sequence, which encodes either exclusively the Rep78 protein or exclusively the Rep68 protein, but not both, wherein the internal P40 promoter has been inactivated and splice donor as well as acceptor sites have been removed, and the second rep open reading frame comprises a coding sequence encoding Rep52/Rep40 proteins.

In certain embodiments of all aspects and embodiments, the first DNA element comprises two rep open reading frames, wherein the first rep open reading frame comprises a coding sequence, which encodes either exclusively the Rep78 protein or exclusively the Rep68 protein, but not both, wherein the internal P40 promoter has been inactivated and splice donor as well as acceptor sites have been removed, and the second rep open reading frame comprises a coding sequence encoding Rep52 protein.

In certain embodiments of all aspects and embodiments, the first DNA element comprises two rep open reading frames, wherein the first rep open reading frame comprises a coding sequence, which encodes either exclusively the Rep78 protein or exclusively the Rep68 protein, but not both, wherein the internal P40 promoter has been inactivated and splice donor as well as acceptor sites have been removed, and the second rep open reading frame comprises a coding sequence encoding Rep52/Rep40 proteins and Cap proteins including a common polyadenylation signal.

In certain embodiments of all aspects and embodiments, the first rep open reading frame is operably linked at its 5'-terminus to the adeno-associated viral promoter P5 or a functional fragment thereof or a variant thereof.

In certain embodiments of all aspects and embodiments, the second rep open reading frame is operably linked at its 5'-terminus to the adeno-associated viral promoter P19 or a functional fragment thereof or a variant thereof.

One independent aspect of the current invention is a mammalian or insect cell comprising an adenoviral VA RNA nucleic acid or a DNA (element) according to the current invention.

One independent aspect according to the current invention is a method for producing recombinant adeno-associated virus (rAAV) particles comprising the following steps:

cultivating/propagating a cell according to the current invention (under conditions suitable for cell division), and recovering the rAAV particles from the cells or the cultivation medium.

Thus, one independent aspect of the current invention is an adenoviral VA RNA nucleic acid or a DNA (molecule) according to the current invention for the production of recombinant adeno-associated virus particles.

One aspect of the invention is a method of generating/for producing recombinant adeno-associated virus (rAAV) particles, the method comprising:

providing a mammalian, in suspension growing cell, which comprises either stably integrated or transiently present a transgene expression cassette interspaced between two AAV ITRs;

open reading frames encoding adenoviral E1A, E1B, E2A, E4 or E4orf6 proteins and an adenoviral VA RNA nucleic acid according to the current invention;

open reading frames encoding adeno-associated Rep/Cap proteins;

propagating/cultivating the mammalian cell (under conditions suitable for cell division); and isolating the rAAV particles from the cell or the cultivation medium and thereby producing the rAAV particles.

In certain embodiments of all aspects and embodiments, each open reading frames is within an expression cassette, i.e. operably linked to a promoter and a polyadenylation signal sequence and/or transcription termination element.

Adenoviral VA RNA Nucleic Acid According to the Current Invention

VA RNA genes are driven by type 2 polymerases III promoters, which comprise two intragenic elements, the A-box and the B-box. Snouwaert et al. (Nucl. Acids Res. 15 (1987) 8293-8303) identified mutants of the VA RNAI B-box that completely abrogate promoter activity. These mutations are unlikely to affect binding of VA RNAI to PKR and related functions (Clark, K. R., et al., Hum. Gene Ther. 6 (1995) 1329-1341).

The current inventors have found that to enable stringent control of the VA RNA transcription it is advantageous to inactivate the wild-type type 2 polymerase III promoter of the VA RNA gene and replaced it by a different promoter, such as, e.g. a type 3 polymerase III promoter, such as, in one preferred embodiment, the U6-snRNA promoter, or a polymerase II promoter or an inducible promoter.

Thus, one aspect according to the current invention is an AAV adenoviral VA RNA coding sequence under the control of a type 3 polymerase III promoter. In one preferred embodiment, the type 3 polymerase III promoter is the human U6-snRNA promoter.

Thus, one aspect according to the current invention is an AAV adenoviral VA RNA coding sequence under the control of a polymerase II promoter.

Type 3 polymerase III promoters comprise two extragenic elements named the proximal sequence element (PSE) and the TATA box. In this regard, type 3 polymerase III promoters resemble polymerase II promoters driving protein gene expression. The spacing requirements between the two elements as well as between the elements and the transcription start site (TSS) are very stringent and the distances are rather short. The PSE of the human U6 promoter extents from position −66 to −47 and the TATA box from −29 to −23. In general, transcription starts at a G, or less preferred at an A nucleotide that resides within a window of +3 and −3 of these distances (Goomer and Kunkel, 1992).

The adenoviral VA RNA nucleic acid according to the current invention enables amongst other things tight transcription control. In certain embodiments, the VA RNA nucleic acid transcription is driven by a type 3 polymerase III promoter, such as, e.g., the human U6-snRNA promoter, or a polymerase II promoter or an inducible promoter.

A specific aspect of the invention is shown in FIG. 2.

In certain embodiments of all aspects and embodiments, the promoter driving the transcription of the adenoviral VA RNA according to the current invention is the human U6 promoter. In certain embodiments, this promoter has the sequence of SEQ ID NO: 42.

In certain embodiments of all aspects and embodiments, the promoter driving the transcriptional adenoviral VA RNA according to the invention is the murine U6 promoter. In certain embodiments, this promoter has the sequence of SEQ ID NO: 43.

In certain embodiments of all aspects and embodiments, the promoter driving the transcription of the adenoviral VA RNA according to the invention is the human H1 pRNA promoter. In certain embodiments, this promoter has the sequence of SEQ ID NO: 44.

In certain embodiments of all aspects and embodiments, the promoter driving the transcription of the adenoviral VA RNA according to the invention is the human tRNA val promoter. In certain embodiments, this promoter has the sequence of SEQ ID NO: 44.

In certain embodiments of all aspects and embodiments, a precise transcription start site is introduced into the non-coding, i.e. regulatory, elements of the adenoviral VA RNA according to the invention.

The viral associated RNA (VA RNA) is a non-coding RNA of adenovirus (Ad), regulating translation. The adenoviral genome comprises two independent copies: VAI (VA RNAI) and VAII (VA RNAII). Both are transcribed by RNA polymerase III (see, e.g., Machitani, M., et al., J. Contr. Rel. 154 (2011) 285-289).

The structure, function, and evolution of adenovirus-associated RNA using a phylogenetic approach was investigated by Ma, Y. and Mathews, M. B. (J. Virol. 70 (1996) 5083-5099). They provided alignments as well as consensus VA RNA sequences based on 47 known human adenovirus serotypes. Said disclosure is herewith incorporated by reference in its entirety into the current application.

VA RNAs, VAI and VAII, are consisting of 157-160 nucleotides (nt).

Depending on the serotype, adenoviruses contain one or two VA RNA genes. VA RNAI is believed to play the dominant pro-viral role, while VA RNAII can partially compensate for the absence of VA RNAI (Vachon, V. K. and Conn, G. L., Virus Res. 212 (2016) 39-52).

The VA RNAs are not essential, but play an important role in efficient viral growth by overcoming cellular antiviral machinery. That is, although VA RNAs are not essential for viral growth, VA RNA-deleted adenovirus cannot grow during the initial step of vector generation, where only a few copies of the viral genome are present per cell, possibly because viral genes other than VA RNAs that block the cellular antiviral machinery may not be sufficiently expressed (see Maekawa, A., et al. Nature Sci. Rep. 3 (2013) 1136).

The A- and B-boxes, which constitute the internal control regions (or promoter) for RNA polymerase III, have been defined experimentally for adenoviral serotype 2 (Ad 2) VA RNAI. These are well conserved. All of the VA RNAs have both boxes at similar positions. The B-box homology is very high. The A-boxes, located 34 to 40 nt upstream of the B-box, are slightly less homologous in some of the VA RNAs. A pair of mutually complementary tetranucleotides, CCGG (SEQ ID NO: 29) and (U/C)CCGG (SEQ ID NO: 30), that forms part of the apical stem of the VA RNA is reasonably well conserved in VA RNA sequences. The first CCGG, which includes the first two bases of the B-box, is invariant. All of the VA RNA genes but one have sequences in the 5' half homologous to the tRNA transcription initiation elements, the A- and B-box consensus sequences RRYNNARYGG (SEQ ID NO: 31) and GWTCRANNC (SEQ ID NO: 32), respectively. The A-box homology in the VA RNAII genes is generally weaker than that in the VA RNAI genes, in accord with the finding that the A-box is less important for VA RNA transcription than the B-box. At the end of the VA RNA coding sequences is a run of T residues flanked by the nucleotides C and G, typical of polymerase III termination sites. The number of thymidines varies from a minimum of 4 to more than 10, and A residues are absent for at least 3 nt on either side of the T-rich run (except in Ad 12 and Ad 18, which have A residues in the middle of very long T runs) (Ma, Y. and Mathews, M. B., J. Virol. 70 (1996) 5083-5099).

The B-box sequences of the VA RNAI and VA RNAII have been found to be essential for the activity of the internal polymerase-III promoter.

Maekawa, A., et al. (Nature Sci. Rep. 3 (2013) 1136) reported efficient production of adenovirus vector lacking genes of virus-associated RNAs that disturb cellular RNAi machinery, wherein HEK293 cells that constitutively and highly express flippase recombinase were infected to obtain VA RNA-deleted adenovirus by FLP recombinase-mediated excision of the VA RNA locus.

The human adenovirus 2 VA RNAI (nucleotides 10586-10810 of GenBank entry AC_000007) sequence is shown in SEQ ID NO: 33; that of the G58T/G59T/C68A (consecutive residue numbering) in SEQ ID NO: 34. SEQ ID NO: 34 is also an aspect of the current invention. The human adenovirus 5 VA RNAI (nucleotides 10579-10820 of GenBank entry AC_000008) sequence is shown in SEQ ID NO: 35; that of the combined human adenovirus 5 VA RNAI and VA RNAII in SEQ ID NO: 36.

Hahn, S. (Nat. Struct. Mol. Biol. 11 (2004) 394-403) and Revyakin, A., et al. (Gen. Devel. 26 (2012) 1691-1702) reported about the structure and mechanism of the RNA polymerase II transcription machinery and Nikitina, T. V. and Tishchenko, L. I. (Mol. Biol. 39 (2005) 161-172) reviewed RNA polymerase III transcription machinery. These are summarized in the following.

Transcription, that is, RNA synthesis on a DNA template, is performed by DNA-dependent RNA polymerases (Pols, [EC 2.7.7.6]). Beside the RNA polymerase, additional factors, termed general transcription factors (GTF), are involved. These are required for recognition of the promoter sequences, the response to regulatory factors, and conformational changes needed for the activity of the polymerase during transcription.

A core promoter (the minimal DNA sequence needed to specify non-regulated or basal transcription) serves to position a Pol in a state termed the Pre-initiation Complex (PIC). In this state, Pol and the GTFs are all bound to the promoter but are not in an active conformation to begin transcription.

Eukaryotic cells contain three Pols, denoted as I, II, and III, which differ in subunit composition.

Genes transcribed by a particular Pol are assigned correspondingly to class I, II, or III.

Pol I transcribes genes for pre-rRNAs. Pol II transcribes all protein-coding genes and genes for snRNAs other than U6 snRNA. Pol III transcribes genes for the 5S rRNA, tRNAs, U6 snRNA, 7SK RNA, 7SL RNA; Alu repeats; some viral genes; and genes for small stable untranslated RNAs.

The genes of the different classes differ in promoter structure, which determines the basal (general) transcription factors and Pol involved in the formation of the PIC.

RNA polymerase II (Pol II) is responsible for the flow of genetic information from DNA to messenger RNA (mRNA) in eukaryotic cells. Studies have identified GTFs-TFIIA, TFIIB, TFIID, TFIIE, TFIIF, and TFIIH—that, together with Pol II, assemble at the promoter site into the PIC and direct transcription initiation at a basal activity level. Further modulation of transcription activity depends on cis control elements in the DNA template that are recognized by sequence-specific activators/repressors assisted by a co-activator.

Sequence elements found in a Pol II core promoters include the TATA element (TATA-binding protein (TBP) binding site), BRE (TFIIB recognition element), Inr (initiator element), and DPE (downstream promoter element). Most promoters contain one or more of these elements, but there is no one element that is absolutely essential for promoter function. The promoter elements are binding sites for subunits of the transcription machinery and serve to orient the transcription machinery at the promoter asymmetrically to direct unidirectional transcription.

The core domain of TBP consists of two imperfect repeats forming a molecule that binds the DNA at the 8-bp TATA element. At TATA-containing promoters, formation of this protein-DNA complex is the initial step in assembly of the transcription machinery. The TATA-like sequence is located about 30 bp upstream of the transcription start site.

RNA polymerase III (Pol III) has the most complex structure among all eukaryotic Pols: the enzyme consists of 17 subunits ranging from ~10 kDa to ~160 kDa and has a total molecular weight of 600-680 kDa.

Class III genes, transcribed by Pol III, comprise three structurally varied promoters, which mostly have an intragenic location. General transcription factors of the Pol III machinery are TFIIIA, TFIIIB, TFIIIC, and the small nuclear RNA-activating protein complex (SNAPc).

The assembly of PICs on different promoters of class III genes (type 1, 2, 3) requires one or more of the A-, B-, and C-boxes; internal control region (ICR); TATA box; distal (DSE) and proximal (PSE) sequence elements. Type 1 genes comprise an A-box at location +57 and a C-box at location +90 relative to the transcription start at +1. Type 2 genes comprise an A-box and a B-box. Type 3 genes comprise a DSE at location −250, a PSE at location −60 and a TATA box at location −27 relative to the transcription start at +1. An A-box may be present, but is not required.

The recruitment and transcription initiation of Pol III on all three types of promoters requires the action of the transcription factor IIIB (TFIIIB) and is highly regulated. The TFIIIB binding site is +/−8 nt around the TATA box. In addition, the TBP is required for transcription by all three polymerases (Han, Y., et al., Cell. Discover. 4 (2018) 40).

With respect to the three types of Pol III genes, Oler, A. J., et al. (Nat. Struct. Mol. Biol. 17 (2010) 620-628) outlined the factors required for directing Pol III to target genes and the three 'Types' of Pol III genes in humans based on 1) the presence and positions of cis regulatory elements, and 2) the requirement for particular basal or accessory transcription factors. Briefly, 5S rRNA is the sole Type 1 gene, uniquely requiring TFIIIA. Type 1 and Type 2 genes both require TFIIIC, a basal factor and targeting complex, which recognizes gene-internal A-box and B-box elements at Type 2, but not Type 1 genes. The TFIIIB complex includes the TBP, needed for TATA/promoter recognition and Pol III initiation. Type 2 and 3 genes utilize alternative assemblies of TFIIIB: BRF1 (TFIIIB-related factor 1) for Type 2 and BRF2 (TFIIIB-related factor 2) for Type 3 genes. Type 3 genes lack an internal A- or B-box, and lack reliance on TFIIIC—relying instead on upstream PSE and DSE and specific factors (OCT1, SNAPc, others) for targeting. Notably, Type 3 Pol III promoters resemble Pol II genes in their architecture, which utilizes upstream regulatory elements rather than gene-internal elements.

The adenoviral VA RNA nucleic acid according to the current invention comprises in certain embodiment in 5'- to 3'-direction at its 5'-end (in the absence of a promoter) or between the promoter and the VA RNA coding sequence (in the presence of a promoter)

at least the six 5'-terminal nucleotides of an adenoviral VA RNAI gene comprising the transcription start site (TSS) (to prevent by-passing of the subsequent polymerase III (poly III) terminator);

a functional polymerase III terminator (to prevent transcription of the VA RNA from the constitutively active upstream promoter), and an adenoviral VA RNAI sequence.

In certain embodiments of all aspects and embodiments, the adenoviral VA RNA nucleic acid according to the current invention further comprises operably linked to its 5'-end a polymerase promoter. In certain embodiments, the promoter is a type 2 polymerase III promoter or a variant thereof, or a type 3 polymerase III promoter or variant thereof, or a polymerase II promoter or a variant thereof or an inducible promoter. In one preferred embodiment of all aspects and embodiments, the promoter is the human U6-snRNA promoter.

In all aspects and embodiments of the invention, the recited elements are operably linked to each other.

In certain embodiments of all aspects and embodiments, the adenoviral VA RNA nucleic acid according to the invention comprises all or a part of the wild-type adenoviral VA RNAI sequence of SEQ ID NO: 37:

```
gggcactctt ccgtggtctg gtggataaat tcgcaagggt
atcatggcgg acgaccgggg ttcgaacccc ggatccggcc
gtccgccgtg atccatgcgg ttaccgcccg cgtgtcgaac
ccaggtgtgc gacgtcagac aacgggggag cgctcctttt
ggcttccttc caggcgcggc ggctgctgcg ctagcttttt
t.
```

In certain embodiments of all aspects and embodiments, the adenoviral VA RNA nucleic acid according to the invention comprises all or a part of the wild-type adenoviral VA RNAI sequence with the mutations G58T, G59T and C68A (sequential numbering) of SEQ ID NO: 38:

```
gggcactctt ccgtggtctg gtggataaat tcgcaagggt
atcatggcgg acgaccgttg ttcgaacacc ggatccggcc
gtccgccgtg atccatgcgg ttaccgcccg cgtgtcgaac
ccaggtgtgc gacgtcagac aacgggggag cgctcctttt
ggcttccttc caggcgcggc ggctgctgcg ctagcttttt
t.
```

FIG. 1 shows an alignment comprising the above sequences.

In certain embodiments, the adenoviral VA RNA nucleic acid according to the invention comprises the following sequences in 5'- to 3'-direction:

(1) a type 2 polymerase III promoter or a variant thereof, or a type 3 polymerase III promoter or variant thereof, in one preferred embodiment, the human U6-snRNA promoter, or a polymerase II promoter, or an inducible promoter; and

```
(2)
                                        (SEQ ID NO: 37)
gggcactctt ccgtggtctg gtggataaat tcgcaagggt
atcatggcgg acgaccgggg ttcgaacccc ggatccggcc
gtccgccgtg atccatgcgg ttaccgcccg cgtgtcgaac
ccaggtgtgc gacgtcagac aacgggggag cgctcctttt
ggcttccttc caggcgcggc ggctgctgcg ctagcttttt t.
```

In one preferred embodiment, the adenoviral VA RNA nucleic acid according to the invention comprises the sequence of

```
                               (SEQ ID NO: 39; FIG. 2)
aaggtcgggc aggaagaggg cctatttccc atgattcctt
catatttgca tatacgatac aaggctgtta gagagataat
tagaattaat ttgactgtaa acacaaagat attagtacaa
aatacgtgac gtagaaagta ataatttctt gggtagtttg
cagttttaaa attatgtttt aaaatggact atcatatgct
taccgtaact tgaaagtatt tcgatttctt ggctttatat
atcttgtgga aaggacgaaa caccgggcac tcttccgtgg
tctggtggat aaattcgcaa gggtatcatg gcggacgacc
ggggttcgaa ccccggatcc ggccgtccgc cgtgatccat
gcggttaccg cccgcgtgtc gaacccaggt gtgcgacgtc
agacaacggg ggagcgctcc ttttggcttc cttccaggcg
cggcggctgc tgcgctagct ttttt.
```

Exemplary Uses and Methods Comprising the Nucleic Acid and the DNA According to the Current Invention The adenoviral VA RNA nucleic acids as well as the DNA (elements) according to the invention can be used in the production of recombinant AAV vectors and recombinant AAV particles comprising the same.

Different methods that are known in the art for generating rAAV particles. For example, transfection using AAV vector and AAV helper sequences in conjunction with co-infection with one AAV helper virus (e.g., adenovirus, herpesvirus, or vaccinia virus) or transfection with a recombinant AAV plasmid, an AAV helper plasmid, and an helper function plasmid. Non-limiting methods for generating rAAV particles are described, for example, in U.S. Pat. Nos. 6,001,650, 6,004,797, WO 2017/096039, and WO 2018/226887. Following recombinant rAAV particle production (i.e. particle generation in cell culture systems), rAAV particles can be obtained from the host cells and cell culture supernatant and purified.

Aspects of the current invention are methods of transducing cells with a molecule, such as a nucleic acid (e.g., plasmid), according to the invention and production of the respective gene product. Additionally, such cells when transduced with sequences, such as plasmids that encode viral packaging proteins and/or helper proteins can produce recombinant viral particles that include the nucleic acid that encodes a protein of interest or comprises a sequence that is transcribed into a transcript of interest, whereof at least one comprises an adenoviral VA RNA nucleic acid or a DNA (element) according to the invention, which in turn produces recombinant viral particles at high yield.

The invention provides viral (e.g., AAV) particle production platform that includes features that distinguish it from current 'industry-standard' viral (e.g., AAV) particle production processes by using the nucleic acid or DNA (element) according to the invention.

In discussing nucleic acids (plasmids), a sequence or structure of a particular polynucleotide may be described herein according to the convention of providing the sequence in the 5' to 3' direction.

More generally, such cells transfected or transduced with a VA RNA nucleic acid or a DNA (element) according to the current invention can be referred to as "recombinant cell". Such a cell can be, for example, a yeast cell, an insect cell, or a mammalian cell, that has been used as recipient of a nucleic acid (plasmid) encoding packaging proteins, such as AAV packaging proteins, a nucleic acid (plasmid) encoding helper proteins, a nucleic acid (plasmid) that encodes a protein or is transcribed into a transcript of interest, i.e. a transgene placed between two AAV ITRs, or other transfer nucleic acid (plasmid), whereof at least one comprises an adenoviral VA RNA nucleic acid or a DNA (element) according to the current invention. The term includes the progeny of the original cell, which has been transduced or transfected. It is understood that the progeny of a single parental cell may not necessarily be completely identical in morphology or in genomic or total nucleic acid complement as the original parent, due to natural, accidental, or deliberate mutation.

Numerous cell growth medium appropriate for sustaining cell viability or providing cell growth and/or proliferation are commercially available or can be readily produced. Examples of such medium include serum free eukaryotic growth mediums, such as medium for sustaining viability or providing for the growth of mammalian (e.g., human) cells. Non-limiting examples include Ham's F12 or F12K medium (SIGMA-ALDRICH®), FreeStyle™ (FS) F17 medium (THERMO FISHER SCIENTIFIC), MEM, DMEM, RPMI-1640 (THERMO FISHER SCIENTIFIC) and mixtures thereof. Such medium can be supplemented with vitamins and/or trace minerals and/or salts and/or amino acids, such as essential amino acids for mammalian (e.g., human) cells.

Helper protein provision can be in the form of a plasmid, phage, transposon or cosmid. In particular, it has been demonstrated that the full-complement of adenovirus genes are not required for helper functions. For example, adenovirus mutants incapable of DNA replication and late gene synthesis have been shown to be permissive for AAV replication. Ito et al., J. Gen. Virol. 9 (1970) 243; Ishibashi et al, Virology 45 (1971) 317.

Mutants within the E2B and E3 regions have been shown to support AAV replication, indicating that the E2B and E3 regions are probably not involved in providing helper function. Carter et al., Virology 126 (1983) 505. However, adenoviruses defective in the E1 region, or having a deleted E4 region, are unable to support AAV replication. Thus, for adenoviral helper proteins, E1A and E4 regions are likely required for AAV replication, either directly or indirectly (see, e.g., Laughlin et al., J. Virol. 41 (1982) 868; Janik et al., Proc. Natl. Acad. Sci. USA 78 (1981) 1925; Carter et al., Virology 126 (1983) 505). Other characterized adenoviral mutants include: E1B (Laughlin et al. (1982), supra; Janik et al. (1981), supra; Ostrove et al., Virology 104 (1980) 502); E2A (Handa et al., J. Gen. Virol. 29 (1975) 239; Strauss et al., J. Virol. 17 (1976) 140; Myers et al., J. Virol. 35 (1980) 665; Jay et al., Proc. Natl. Acad. Sci. USA 78 (1981) 2927; Myers et al., J. Biol. Chem. 256 (1981) 567); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)).

Studies of the helper proteins provided by adenoviruses having mutations in the E1B have reported that the E1B 55 kDa protein is required for AAV particle production, while the E1B 19 kDa protein is not. In addition, WO 97/17458 and Matshushita et al. (Gene Therapy 5 (1998) 938-945) described helper function plasmids encoding various adenoviral genes. An example of a helper plasmid comprises an adenovirus VA RNA coding region, an adenovirus E4 ORF6 coding region, an adenovirus E2A 72 kDa coding region, an adenovirus E1A coding region, and an adenovirus E1B region lacking an intact E1B 55 kDa coding region (see, e.g., WO 01/83797).

Thus, herein is provided a method for producing recombinant AAV vectors or AAV particles comprising said recombinant AAV vectors, which comprise a nucleic acid that encodes a protein or is transcribed into a transcript of interest, using an adenoviral VA RNA nucleic acid or a DNA (element) according to the current invention.

One aspect of the current invention is a method for producing recombinant AAV vectors or AAV particles comprising said recombinant AAV vectors, which comprise a nucleic acid that encodes a protein or is transcribed into a transcript of interest, comprises the steps of (i) providing one or more plasmids comprising nucleic acids encoding AAV packaging proteins and/or nucleic acids encoding helper proteins, whereof at least one comprises an adenoviral VA RNA nucleic acid or a DNA (element) according to the current invention;
(ii) providing a plasmid comprising a nucleic acid that encodes a protein of interest or is transcribed into a transcript of interest;
(iii) contacting one or more mammalian cells with the provided plasmids;
(iv) either further adding a transfection reagent and optionally incubating the plasmid/transfection reagent/cell mixture; or providing a physical means, such as an electric current, to introduce the nucleic acid into the cells;
(v) cultivating the transfected cells and inducing the RMCI at a certain point/cultivation time during the cultivation;

(vi) harvesting the cultivated cells and/or culture medium from the cultivated cells to produce a cell and/or culture medium harvest; and (vii) isolating and/or purifying recombinant AAV vector or AAV particle from the cell and/or culture medium harvest thereby producing recombinant AAV vector or AAV particle comprising a nucleic acid that encodes a protein of interest or is transcribed into a transcript of interest.

One aspect of the current invention is a method for producing recombinant AAV vectors or AAV particles comprising said recombinant AAV vectors, which comprise a nucleic acid that encodes a protein or is transcribed into a transcript of interest, comprises the steps of (i) providing one or more plasmids comprising nucleic acids encoding AAV packaging proteins and/or nucleic acids encoding helper proteins, whereof at least one comprises an adenoviral VA RNA nucleic acid or a DNA (element) according to the current invention;

(ii) providing a plasmid comprising a nucleic acid that encodes a protein of interest or is transcribed into a transcript of interest;

(iii) contacting one or more mammalian cells with the provided plasmids of (i);

(iv) either further adding a transfection reagent and optionally incubating the plasmid/transfection reagent/cell mixture; or providing a physical means, such as an electric current, to introduce the nucleic acid into the cells;

(v) selecting a stably transfected cell;

(vi) contacting the selected cell of (v) with the provided plasmids of (ii);

(vii) either further adding a transfection reagent and optionally incubating the plasmid/transfection reagent/cell mixture; or providing a physical means, such as an electric current, to introduce the nucleic acid into the cells;

(viii) cultivating the transfected cells of (viii) and inducing the RMCI at a certain point/cultivation time during the cultivation;

(ix) harvesting the cultivated cells and/or culture medium from the cultivated cells to produce a cell and/or culture medium harvest; and (x) isolating and/or purifying recombinant AAV vector or AAV particle from the cell and/or culture medium harvest thereby producing recombinant AAV vector or AAV particle comprising a nucleic acid that encodes a protein of interest or is transcribed into a transcript of interest.

One aspect of the current invention is a method for producing recombinant AAV vectors or AAV particles comprising said recombinant AAV vectors, which comprise a nucleic acid that encodes a protein or is transcribed into a transcript of interest, comprises the steps of (i) providing a mammalian cell comprising nucleic acids encoding AAV packaging proteins and/or nucleic acids encoding helper proteins, whereof at least one comprises an adenoviral VA RNA nucleic acid or a DNA (element) according to the current invention;

(ii) providing a plasmid comprising a nucleic acid that encodes a protein of interest or is transcribed into a transcript of interest;

(iii) contacting the cell of (i) with the provided plasmid of (ii);

(iv) either further adding a transfection reagent and optionally incubating the plasmid/transfection reagent/cell mixture; or providing a physical means, such as an electric current, to introduce the nucleic acid into the cell;

(v) selecting a stably transfected cell;

(vi) cultivating the stably transfected cell of (v) and inducing the RMCI at a certain point/cultivation time during the cultivation;

(vii) harvesting the cultivated cells and/or culture medium from the cultivated cells to produce a cell and/or culture medium harvest; and (viii) isolating and/or purifying recombinant AAV vector or AAV particle from the cell and/or culture medium harvest thereby producing recombinant AAV vector or AAV particle comprising a nucleic acid that encodes a protein of interest or is transcribed into a transcript of interest.

The introduction of the nucleic acid comprising an adenoviral VA RNA nucleic acid or a DNA (element) according to the current invention into cells can be done in multiple ways.

Diverse methods for the DNA transfer into mammalian cells have been reported in the art. These are all useful in the methods according to the current invention. In certain embodiments of all aspects and embodiments, electroporation, nucleofection, or microinjection for nucleic acid transfer/transfection is used. In certain embodiments of all aspects and embodiments, an inorganic substance (such as, e.g., calcium phosphate/DNA co-precipitation), a cationic polymer (such as, e.g., polyethylenimine, DEAE-dextran), or a cationic lipid (lipofection) is used for nucleic acid transfer/transfection is used. Calcium phosphate and polyethylenimine are the most commonly used reagents for transfection for nucleic acid transfer in larger scales (see, e.g., Baldi et al., Biotechnol. Lett. 29 (2007) 677-684), whereof polyethylenimine is preferred.

In certain embodiments of all aspects and embodiments, the nucleic acid comprising an adenoviral VA RNA nucleic acid or a DNA (element) according to the current invention is provided in a composition in combination with polyethylenimine (PEI), optionally in combination with cells. In certain embodiments, the composition includes a plasmid/PEI mixture, which has a plurality of components: (a) one or more plasmids comprising nucleic acids encoding AAV packaging proteins and/or nucleic acids encoding helper proteins whereof at least one comprises an adenoviral VA RNA nucleic acid or a DNA (element) according to the invention; (b) a plasmid comprising a nucleic acid that encodes a protein or is transcribed into a transcript of interest; and (c) a polyethylenimine (PEI) solution. In certain embodiments, the plasmids are in a molar ratio range of about 1:0.01 to about 1:100, or are in a molar ratio range of about 100:1 to about 1:0.01, and the mixture of components (a), (b) and (c) has optionally been incubated for a period of time from about 10 seconds to about 4 hours.

In certain embodiments of all aspects and embodiments, the compositions further comprise cells. In certain embodiments, the cells are in contact with the plasmid/PEI mixture of components (a), (b) and/or (c).

In certain embodiments of all aspects and embodiments, the composition, optionally in combination with cells, further comprise free PEI. In certain embodiments, the cells are in contact with the free PEI.

In certain embodiments of all aspects and embodiments, the cells have been in contact with the mixture of components (a), (b) and/or (c) for at least about 4 hours, or about 4 hours to about 140 hours, or for about 4 hours to about 96 hours. In one preferred embodiment, the cells have been in contact with the mixture of components (a), (b) and/or (c) and optionally free PEI, for at least about 4 hours.

Beside a nucleic acid, comprising the adenoviral VA RNA or a DNA (element) according to the invention the composition may comprise further plasmids. Such plasmids and cells may be in contact with free PEI. In certain embodiments, the plasmids and/or cells have been in contact with the free PEI for at least about 4 hours, or about 4 hours to about 140 hours, or for about 4 hours to about 96 hours.

The invention also provides methods for producing transfected cells using a nucleic acid comprising an adenoviral VA RNA nucleic acid or a DNA (element) according to the current invention. The method includes the steps of providing a nucleic acid comprising an adenoviral VA RNA nucleic acid or a DNA (element) according to the current invention and optionally one or more additional plasmids; providing a solution comprising polyethylenimine (PEI); and mixing the nucleic acid and optionally the plasmid(s) with the PEI solution to produce a nucleic acid/plasmid/PEI mixture. In certain embodiments, such mixtures are incubated for a period in the range of about 10 seconds to about 4 hours. In such methods, cells are then contacted with the nucleic acid/plasmid/PEI mixture to produce a nucleic acid/plasmid/PEI cell culture; then free PEI is added to the nucleic acid/plasmid/PEI cell culture produced to produce a free PEI/nucleic acid/plasmid/PEI cell culture; and then the free PEI/nucleic acid/plasmid/PEI cell culture produced is incubated for at least about 4 hours, thereby producing transfected cells. In certain embodiments, the plasmid comprises a nucleic acid that encodes a protein or is transcribed into a transcript of interest.

Further provided are methods for producing transfected cells that produce recombinant AAV vector or AAV particle, which include providing one or more plasmids comprising nucleic acids encoding AAV packaging proteins and/or nucleic acids encoding helper proteins, wherein at least one thereof comprises an adenoviral VA RNA nucleic acid or a DNA (element) according to the current invention; providing a plasmid comprising a nucleic acid that encodes a protein or is transcribed into a transcript of interest; providing a solution comprising polyethylenimine (PEI); mixing the aforementioned plasmids with the PEI solution, wherein the plasmids are in a molar ratio range of about 1:0.01 to about 1:100, or are in a molar ratio range of about 100:1 to about 1:0.01, to produce a plasmid/PEI mixture (and optionally incubating the plasmid/PEI mixture for a period in the range of about 10 seconds to about 4 hours); contacting cells with the plasmid/PEI mixture, to produce a plasmid/PEI cell culture; adding free PEI to the plasmid/PEI cell culture produced to produce a free PEI/plasmid/PEI cell culture; and incubating the free PEI/plasmid/PEI cell culture for at least about 4 hours, thereby producing transfected cells that produce recombinant AAV vector or particle comprising a nucleic acid that encodes a protein or is transcribed into a transcript of interest.

Additionally provided are methods for producing recombinant AAV vector or AAV particle comprising a nucleic acid that encodes a protein or is transcribed into a transcript of interest, which includes providing one or more plasmids comprising nucleic acids encoding AAV packaging proteins and/or nucleic acids encoding helper proteins whereof at least one comprises an adenoviral VA RNA nucleic acid or a DNA (element) according to the current invention; providing a plasmid comprising a nucleic acid that encodes a protein of interest or is transcribed into a transcript of interest; providing a solution comprising polyethylenimine (PEI); mixing the aforementioned plasmids with the PEI solution, wherein the plasmids are in a molar ratio range of about 1:0.01 to about 1:100, or are in a molar ratio range of about 100:1 to about 1:0.01, to produce a plasmid/PEI mixture (and optionally incubating the plasmid/PEI mixture for a period of time in the range of about 10 seconds to about 4 hours); contacting cells with the plasmid/PEI mixture produced as described to produce a plasmid/PEI cell culture; adding free PEI to the plasmid/PEI cell culture produced as described to produce a free PEI/plasmid/PEI cell culture; incubating the plasmid/PEI cell culture or the free PEI/plasmid/PEI cell culture produced for at least about 4 hours to produce transfected cells; harvesting the transfected cells produced and/or culture medium from the transfected cells produced to produce a cell and/or culture medium harvest; and isolating and/or purifying recombinant AAV vector or particle from the cell and/or culture medium harvest produced thereby producing recombinant AAV vector or particle comprising a nucleic acid that encodes a protein or is transcribed into a transcript of interest.

Methods for producing recombinant AAV vectors or AAV particles using the adenoviral VA RNA or DNA (element) according to the current invention can include one or more further steps or features. An exemplary step or feature includes, but is not limited to, a step of harvesting the cultivated cells produced and/or harvesting the culture medium from the cultivated cells produced to produce a cell and/or culture medium harvest. An additional exemplary step or feature includes, but is not limited to isolating and/or purifying recombinant AAV vector or AAV particle from the cell and/or culture medium harvest thereby producing recombinant AAV vector or AAV particle comprising a nucleic acid that encodes a protein or is transcribed into a transcript of interest.

In certain embodiments of all aspects and embodiments, PEI is added to the plasmids and/or cells at various time points. In certain embodiments, free PEI is added the cells before, at the same time as, or after the plasmid/PEI mixture is contacted with the cells.

In certain embodiments of all aspects and embodiments, the cells are at particular densities and/or cell growth phases and/or viability when contacted with the plasmid/PEI mixture and/or when contacted with the free PEI. In one preferred embodiment, cells are at a density in the range of about 1×10E5 cells/mL to about 1×10E8 cells/mL when contacted with the plasmid/PEI mixture and/or when contacted with the free PEI. In certain embodiments, viability of the cells when contacted with the plasmid/PEI mixture or with the free PEI is about 60% or greater than 60%, or wherein the cells are in log phase growth when contacted with the plasmid/PEI mixture, or viability of the cells when contacted with the plasmid/PEI mixture or with the free PEI is about 90% or greater than 90%, or wherein the cells are in log phase growth when contacted with the plasmid/PEI mixture or with the free PEI.

Encoded AAV packaging proteins include, in certain embodiments of all aspects and embodiments, AAV rep and/or AAV cap. Such AAV packaging proteins include, in certain embodiments of all aspects and embodiments, AAV rep and/or AAV cap proteins of any AAV serotype.

Encoded helper proteins include, in certain embodiments of all aspects and embodiments, adenovirus E2 and/or E4, and/or non-AAV helper proteins.

In certain embodiments of all aspects and embodiments, the nucleic acids (plasmids) are used at particular amounts or ratios. In certain embodiments, the total amount of plasmid comprising the nucleic acid that encodes a protein or is transcribed into a transcript of interest and the one or more plasmids comprising nucleic acids encoding AAV packaging proteins and/or nucleic acids encoding helper proteins, whereof at least one comprises an adenoviral VA RNA nucleic acid or a DNA (element) according to the current invention, is in the range of about 0.1 μg to about 15 μg per mL of cells. In certain embodiments, the molar ratio of the plasmid comprising the nucleic acid that encodes a protein or is transcribed into a transcript of interest to the one or more plasmids comprising nucleic acids encoding AAV packaging proteins and/or nucleic acids encoding helper proteins, whereof at least one comprises an adenoviral VA RNA nucleic acid or a DNA (element) according to the invention, is in the range of about 1:5 to about 1:1, or is in the range of about 1:1 to about 5:1.

Plasmids can include nucleic acids on different or the same plasmids. In certain embodiments of all aspects and embodiments, a first plasmid comprises the nucleic acids encoding AAV packaging proteins and a second plasmid comprises the nucleic acids encoding helper proteins. At least one of these nucleic acids further comprises an adenoviral VA RNA nucleic acid or a DNA (element) according to the current invention.

In certain embodiments of all aspects and embodiments, the molar ratio of the plasmid comprising the nucleic acid that encodes a protein or is transcribed into a transcript of interest to a first plasmid comprising the nucleic acids encoding AAV packaging proteins to a second plasmid comprising the nucleic acids encoding helper proteins is in the range of about 1-5:1:1, or 1: 1-5:1, or 1:1:1-5 in co-transfection.

In certain embodiments of all aspects and embodiments, the cell is a eukaryotic cell. In certain embodiments, the eukaryotic cell is a mammalian cell. In one preferred embodiment, the cell is a HEK293 cell or a CHO cell.

The cultivation can be performed using the generally used conditions for the cultivation of eukaryotic cells of about 37° C., 95% humidity and 8 vol.-% $CO_2$. The cultivation can be performed in serum containing or serum free medium, in adherent culture or in suspension culture. The suspension cultivation can be performed in any fermentation vessel, such as, e.g., in stirred tank reactors, wave reactors, in shaker vessels or spinner vessels or in so called roller bottles. Transfection can be performed in high throughput format and screening, respectively, e.g. in a 96 or 384 well format.

Methods according to the current invention include AAV particles of any serotype, or a variant thereof. In certain embodiments of all aspects and embodiments, a recombinant AAV particle comprises any of AAV serotypes 1-12, an AAV VP1, VP2 and/or VP3 capsid protein, or a modified or variant AAV VP1, VP2 and/or VP3 capsid protein, or wild-type AAV VP1, VP2 and/or VP3 capsid protein. In certain embodiments of all aspects and embodiments, an AAV particle comprises an AAV serotype or an AAV pseudotype, where the AAV pseudotype comprises an AAV capsid serotype different from an ITR serotype.

Methods according to the invention that provide or include AAV vectors or particles can also include other elements. Examples of such elements include but are not limited to: an intron, an expression control element, one or more adeno-associated virus (AAV) inverted terminal repeats (ITRs) and/or a filler/stuffer polynucleotide sequence. Such elements can be within or flank the nucleic acid that encodes a protein or is transcribed into a transcript of interest, or the expression control element can be operably linked to nucleic acid that encodes a protein or is transcribed into a transcript of interest, or the AAV ITR(s) can flank the 5'- or 3'-terminus of nucleic acid that encodes a protein or is transcribed into a transcript of interest, or the filler polynucleotide sequence can flank the 5'- or 3'-terminus of nucleic acid that encodes a protein or is transcribed into a transcript of interest.

Expression control elements include constitutive or regulatable control elements, such as a tissue-specific expression control element or promoter (e.g. that provides for expression in liver).

ITRs can be any of: AAV2 or AAV6 or AAV8 or AAV9 serotypes, or a combination thereof. AAV particles can include any VP1, VP2 and/or VP3 capsid protein having 75% or more sequence identity to any of AAV1, AAV2, AAV3, AAV4, AAV5, AAV6, AAV10, AAV11, AAV-2i8 or AAV rh74 VP1, VP2 and/or VP3 capsid proteins, or comprises a modified or variant VP1, VP2 and/or VP3 capsid protein selected from any of AAV1, AAV2, AAV3, AAV4, AAV5, AAV6, AAV10, AAV11, AAV-2i8 and AAV rh74 AAV serotypes.

Following production of recombinant viral (e.g., AAV) particles as set forth herein, if desired, the viral (e.g., rAAV) particles can be purified and/or isolated from host cells using a variety of conventional methods. Such methods include column chromatography, CsCl gradients, and the like. For example, a plurality of column purification steps such as purification over an anion exchange column, an affinity column and/or a cation exchange column can be used. (See, e.g., WO 02/12455 and US 2003/0207439). Alternatively, or in addition, CsCl gradient steps can be used (see, e.g., US 2012/0135515; and US 2013/0072548). Further, if the use of infectious virus is employed to express the packaging and/or helper proteins, residual virus can be inactivated, using various methods. For example, adenovirus can be inactivated by heating to temperatures of approximately 60° C. for, e.g., 20 minutes or more. This treatment effectively inactivates the helper virus since AAV is heat stable while the helper adenovirus is heat labile.

Recombinant AAV vectors, as well as methods and uses thereof, include any viral strain or serotype. As a non-limiting example, a recombinant AAV vector can be based upon any AAV genome, such as AAV-1, -2, -3, -4, -5, -6, -7, -8, -9, -10, -11-12, 2i8, or AAV rh74 for example. Such vectors can be based on the same strain or serotype (or subgroup or variant), or be different from each other. As a non-limiting example, a recombinant AAV vector based upon one serotype genome can be identical to one or more of the capsid proteins that package the vector. In addition, a recombinant AAV vector genome can be based upon an AAV (e.g., AAV2) serotype genome distinct from one or more of the AAV capsid proteins that package the vector. For example, the AAV vector genome can be based upon AAV2, whereas at least one of the three capsid proteins could be an AAV1, AAV3, AAV4, AAV5, AAV6, AAV7, AAV8, AAV9, AAV10, AAV11, AAV12, AAV-2i8, or AAV rh74 or variant thereof, for example. AAV variants include variants and chimeras of AAV1, AAV2, AAV3, AAV4, AAV5, AAV6, AAV7, AAV8, AAV9, AAV10, AAV11, AAV12, AAV-2i8 and AAV rh74 capsids.

In certain embodiments of all aspects and embodiments, adeno-associated virus (AAV) vectors include AAV1, AAV2, AAV3, AAV4, AAV5, AAV6, AAV7, AAV8, AAV9, AAV10, AAV11, AAV12, AAV-2i8, and AAV rh74, as well as variants (e.g., capsid variants, such as amino acid insertions, additions, substitutions and deletions) thereof, for example, as set forth in WO 2013/158879, WO 2015/013313 and US 2013/0059732 (disclosing LK01, LK02, LK03, etc.).

AAV and AAV variants (e.g., capsid variants) serotypes (e.g., VP1, VP2, and/or VP3 sequences) may or may not be distinct from other AAV serotypes, including, for example, AAV1-AAV12 (e.g., distinct from VP1, VP2, and/or VP3 sequences of any of AAV1-AAV12 serotypes).

In certain embodiments of all aspects and embodiments, an AAV particle related to a reference serotype has a polynucleotide, polypeptide or subsequence thereof that includes or consists of a sequence at least 80% or more (e.g., 85%, 90%, 95%, 96%, 97%, 98%, 99%, 99.1%, 99.2%, 99.3%, 99.4%, 99.5%, etc.) identical to one or more AAV1, AAV2, AAV3, AAV4, AAV5, AAV6, AAV7, AAV8, AAV9, AAV10, AAV11, AAV12, AAV-2i8 or AAV rh74 (e.g., such as an ITR, or a VP1, VP2, and/or VP3 sequences).

Compositions, methods and uses of the invention include AAV sequences (polypeptides and nucleotides), and subsequences thereof that exhibit less than 100% sequence identity to a reference AAV serotype such as AAV1, AAV2, AAV3, AAV4, AAV5, AAV6, AAV7, AAV8, AAV9, AAV10, AAV11, AAV12, AAV-2i8, or AAV rh74, but are distinct from and not identical to known AAV genes or proteins, such as AAV1, AAV2, AAV3, AAV4, AAV5, AAV6, AAV7, AAV8, AAV9, AAV10, AAV11, AAV12, AAV-2i8, or AAV rh74, genes or proteins, etc. In certain embodiment of all aspects and embodiments, an AAV polypeptide or subsequence thereof includes or consists of a sequence at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to any reference AAV sequence or subsequence thereof, such as AAV1, AAV2, AAV3, AAV4, AAV5, AAV6, AAV7, AAV8, AAV9, AAV10, AAV11, AAV12, AAV-2i8, or AAV rh74 (e.g., VP1, VP2 and/or VP3 capsid or ITR). In certain aspects, an AAV variant has 1, 2, 3, 4, 5, 5-10, 10-15, 15-20 or more amino acid substitutions.

Recombinant AAV particles, including AAV1, AAV2, AAV3, AAV4, AAV5, AAV6, AAV7, AAV8, AAV9, AAV10, AAV11, AAV12, AAV-2i8, or AAV rh74, and variant, related, hybrid and chimeric sequences, can be constructed using recombinant techniques that are known to the skilled artisan, to include one or more nucleic acid sequences (transgenes) flanked with one or more functional AAV ITR sequences.

Recombinant particles (e.g., rAAV particles) can be incorporated into pharmaceutical compositions. Such pharmaceutical compositions are useful for, among other things, administration and delivery to a subject in vivo or ex vivo. In certain embodiments, pharmaceutical compositions contains a pharmaceutically acceptable carrier or excipient. Such excipients include any pharmaceutical agent that does not itself induce an immune response harmful to the individual receiving the composition, and which may be administered without undue toxicity.

Protocols for the generation of adenoviral vectors have been described in U.S. Pat. Nos. 5,998,205; 6,228,646; 6,093,699; 6,100,242; WO 94/17810 and WO 94/23744, which are incorporated herein by reference in their entirety.

Despite the pathogenicity for humans, an objective in the rAAV vector production and purification systems is to implement strategies to minimize/control the generation of production related impurities such as proteins, nucleic acids, and vector-related impurities, including wild-type/pseudo wild-type AAV species (wtAAV) and AAV-encapsulated residual DNA impurities.

Considering that the rAAV particle represents only a minor fraction of the biomass, rAAV particles need to be purified to a level of purity, which can be used as a clinical human gene therapy product (see, e.g., Smith P. H., et al., Mo. Therapy 7 (2003) 8348; Chadeuf G., et al, Mo. Therapy 12 (2005) 744; report from the CHMP gene therapy expert group meeting, European Medicines Agency EMEA/CHMP 2005, 183989/2004).

As an initial step, typically the cultivated cells that produce the rAAV particles are harvested, optionally in combination with harvesting cell culture supernatant (medium) in which the cells (suspension or adherent) producing rAAV particles have been cultured. The harvested cells and optionally cell culture supernatant may be used as is, as appropriate, or concentrated. Further, if infection is employed to express helper functions, residual helper virus can be inactivated. For example, adenovirus can be inactivated by heating to temperatures of approximately 60° C. for, e.g., 20 minutes or more, which inactivates only the helper virus since AAV is heat stable while the helper adenovirus is heat labile.

Cells and/or supernatant of the harvest are lysed by disrupting the cells, for example, by chemical or physical means, such as detergent, microfluidization and/or homogenization, to release the rAAV particles. Concurrently during cell lysis or subsequently after cell lysis, a nuclease, such as, e.g., benzonase, is added to degrade contaminating DNA. Typically, the resulting lysate is clarified to remove cell debris, e.g. by filtering or centrifuging, to render a clarified cell lysate. In a particular example, lysate is filtered with a micron diameter pore size filter (such as a 0.1-10.0 μm pore size filter, for example, a 0.45 μm and/or pore size 0.2 μm filter), to produce a clarified lysate.

The lysate (optionally clarified) contains AAV particles (comprising rAAV vectors as well as empty capsids) and production/process related impurities, such as soluble cellular components from the host cells that can include, inter alia, cellular proteins, lipids, and/or nucleic acids, and cell culture medium components. The optionally clarified lysate is then subjected to purification steps to purify AAV particles (comprising rAAV vectors) from impurities using chromatography. The clarified lysate may be diluted or concentrated with an appropriate buffer prior to the first chromatography step.

After cell lysis, optional clarifying, and optional dilution or concentration, a plurality of subsequent and sequential chromatography steps can be used to purify rAAV particles.

A first chromatography step may be cation exchange chromatography or anion exchange chromatography. If the first chromatography step is cation exchange chromatography the second chromatography step can be anion exchange chromatography or size exclusion chromatography (SEC). Thus, in certain embodiments of all aspects and embodiments, rAAV particle purification is via cation exchange chromatography, followed by purification via anion exchange chromatography.

Alternatively, if the first chromatography step is cation exchange chromatography the second chromatography step can be size exclusion chromatography (SEC). Thus, in certain embodiments of all aspects and embodiments, rAAV particle purification is via cation exchange chromatography, followed by purification via size exclusion chromatography (SEC).

Still alternatively, a first chromatography step may be affinity chromatography. If the first chromatography step is affinity chromatography the second chromatography step can be anion exchange chromatography. Thus, in certain embodiments of all aspects and embodiments, rAAV particle purification is via affinity chromatography, followed by purification via anion exchange chromatography.

Optionally, a third chromatography can be added to the foregoing chromatography steps. Typically, the optional third chromatography step follows cation exchange, anion exchange, size exclusion or affinity chromatography.

Thus, in certain embodiments of all aspects and embodiments, rAAV particle purification is via cation exchange chromatography, followed by purification via anion exchange chromatography, followed by purification via size exclusion chromatography (SEC).

In addition, in certain embodiments of all aspects and embodiments, further rAAV particle purification is via cation exchange chromatography, followed by purification via size exclusion chromatography (SEC), followed by purification via anion exchange chromatography.

In yet further embodiments of all aspects and embodiments, rAAV particle purification is via affinity chromatography, followed by purification via anion exchange chromatography, followed by purification via size exclusion chromatography (SEC).

In yet further embodiments of all aspects and embodiments, rAAV particle purification is via affinity chromatography, followed by purification via size exclusion chromatography (SEC), followed by purification via anion exchange chromatography.

Cation exchange chromatography functions to separate the AAV particles from cellular and other components present in the clarified lysate and/or column eluate from an affinity or size exclusion chromatography. Examples of strong cation exchange resins capable of binding rAAV particles over a wide pH range include, without limitation, any sulfonic acid based resin as indicated by the presence of the sulfonate functional group, including aryl and alkyl substituted sulfonates, such as sulfopropyl or sulfoethyl resins. Representative matrices include but are not limited to POROS HS, POROS HS 50, POROS XS, POROS SP, and POROS S (strong cation exchangers available from THERMO FISHER SCIENTIFIC, Inc., Waltham, MA, USA). Additional examples include Capto S, Capto S ImpAct, Capto S ImpRes (strong cation exchangers available from GE HealthCare, Marlborough, MA, USA), and commercial DOWEX®, AMBERLITE®, and AMBERLYST® families of resins available from Aldrich Chemical Company (Milwaukee, WI, USA). Weak cation exchange resins include, without limitation, any carboxylic acid based resin.

Exemplary cation exchange resins include carboxymethyl (CM), phospho (based on the phosphate functional group), methyl sulfonate (S) and sulfopropyl (SP) resins.

Anion exchange chromatography functions to separate AAV particles from proteins, cellular and other components present in the clarified lysate and/or column eluate from an affinity or cation exchange or size exclusion chromatography. Anion exchange chromatography can also be used to reduce and thereby control the amount of empty capsids in the eluate. For example, the anion exchange column having rAAV particle bound thereto can be washed with a solution comprising NaCl at a modest concentration (e.g., about 100-125 mM, such as 110-115 mM) and a portion of the empty capsids can be eluted in the flow through without substantial elution of the rAAV particles. Subsequently, rAAV particles bound to the anion exchange column can be eluted using a solution comprising NaCl at a higher concentration (e.g., about 130-300 mM NaCl), thereby producing a column eluate with reduced or depleted amounts of empty capsids and proportionally increased amounts of rAAV particles comprising an rAAV vector.

Exemplary anion exchange resins include, without limitation, those based on polyamine resins and other resins. Examples of strong anion exchange resins include those based generally on the quaternized nitrogen atom including, without limitation, quaternary ammonium salt resins such as trialkylbenzyl ammonium resins. Suitable exchange chromatography materials include, without limitation, MACRO PREP Q (strong anion-exchanger available from BioRad, Hercules, CA, USA); UNOSPHERE Q (strong anion-exchanger available from BioRad, Hercules, CA, USA); POROS 50HQ (strong anion-exchanger available from Applied Biosystems, Foster City, CA, USA); POROS XQ (strong anion-exchanger available from Applied Biosystems, Foster City, CA, USA); POROS SOD (weak anion-exchanger available from Applied Biosystems, Foster City, CA, USA); POROS 50PI (weak anion-exchanger available from Applied Biosystems, Foster City, CA, USA); Capto Q, Capto XQ, Capto Q ImpRes, and SOURCE 30Q (strong anion-exchanger available from GE healthcare, Marlborough, MA, USA); DEAE SEPHAROSE (weak anion-exchanger available from Amersham Biosciences, Piscataway, NJ, USA); Q SEPHAROSE (strong anion-exchanger available from Amersham Biosciences, Piscataway, NJ, USA). Additional exemplary anion exchange resins include aminoethyl (AE), diethylaminoethyl (DEAE), diethylaminopropyl (DEPE) and quaternary amino ethyl (QAE).

A manufacturing process to purify recombinant AAV particles intended as a product to treat human disease should achieve the following objectives: 1) consistent particle purity, potency and safety; 2) manufacturing process scalability; and 3) acceptable cost of manufacturing.

Exemplary processes for recombinant AAV particle purification are reported in WO 2019/006390.

The below outlined recombinant adeno-associated virus particle (rAAV particle) purification and production methods are scalable up to large scale. For example, to a suspension culture of 5, 10, 10-20, 20-50, 50-100, 100-200 or more liters volume. The recombinant adeno-associated virus particle purification and production methods are applicable to a wide variety of AAV serotypes/capsid variants.

In certain embodiments of all aspects and embodiments, the purification of rAAV particles comprises the steps of (a) harvesting cells and/or cell culture supernatant comprising rAAV particles to produce a harvest;
(b) optionally concentrating the harvest produced in step (a) to produce a concentrated harvest;
(c) lysing the harvest produced in step (a) or the concentrated harvest produced in step (b) to produce a lysate;
(d) treating the lysate produced in step (c) to reduce contaminating nucleic acid in the lysate thereby producing a nucleic acid reduced lysate;
(e) optionally filtering the nucleic acid reduced lysate produced in step (d) to produce a clarified lysate, and optionally diluting the clarified lysate to produce a diluted clarified lysate;
(f) subjecting the nucleic acid reduced lysate of step (d), the clarified lysate of step (e), or the diluted clarified lysate produced in step (e) to a cation exchange column chromatography to produce a column eluate comprising rAAV particles, thereby separating rAAV particles from protein impurities or other production/process related impurities, and optionally diluting the column eluate to produce a diluted column eluate;
(g) subjecting the column eluate or the diluted column eluate produced in step (f) to an anion exchange chromatography to produce a second column eluate comprising rAAV particles, thereby separating rAAV particles from protein impurities or production/process related impurities, and optionally concentrating the second column eluate to produce a concentrated second column eluate;

(h) subjecting the second column eluate or the concentrated second column eluate produced in step (g) to a size exclusion column chromatography (SEC) to produce a third column eluate comprising rAAV particles, thereby separating rAAV particles from protein impurities or production/process related impurities, and optionally concentrating the third column eluate to produce a concentrated third column eluate; and (i) filtering the third column eluate or the concentrated third column eluate produced in step (h), thereby producing purified rAAV particles.

In one embodiment, steps (a) to (f) are maintained and combined with the following steps:

(g) subjecting the column eluate or the concentrated column eluate produced in step (f) to a size exclusion column chromatography (SEC) to produce a second column eluate comprising rAAV particles, thereby separating rAAV particles from protein impurities or other production/process related impurities, and optionally diluting the second column eluate to produce a concentrated second column eluate;

(h) subjecting the second column eluate or the diluted second column eluate produced in step (g) to an anion exchange chromatography to produce a third column eluate comprising rAAV particles thereby separating rAAV particles from protein impurities production/process related impurities and optionally diluting the third column eluate to produce a diluted third column eluate; and (i) filtering the third column eluate or the concentrated third column eluate produced in step (h), thereby producing purified rAAV particles.

In one embodiment, steps (a) to (g) are maintained and combined with the following step:

(h) filtering the second column eluate or the concentrated second column eluate produced in step (g), thereby producing purified rAAV particles.

In embodiment, steps (a) to (e) are maintained and combined with the following steps:

(f) subjecting the nucleic acid reduced lysate in step (d), or clarified lysate or diluted clarified lysate produced in step (e) to an AAV affinity column chromatography to produce a column eluate comprising rAAV particles, thereby separating rAAV particles from protein impurities or other production/process related impurities, and optionally concentrating the column eluate to produce a concentrated column eluate;

(g) subjecting the column eluate or the concentrated column eluate produced in step (f) to a size exclusion column chromatography (SEC) to produce a second column eluate comprising rAAV particles, thereby separating rAAV particles from protein impurities or other production/process related impurities, and optionally diluting the second column eluate to produce a diluted second column eluate;

(h) optionally subjecting the second column eluate or the diluted second column eluate produced in step (g) to an anion exchange chromatography to produce a third column eluate comprising rAAV particles, thereby separating rAAV particles from protein impurities or other production/process related impurities, and optionally diluting the third column eluate to produce a diluted third column eluate; and (i) filtering the second column eluate or the diluted second column eluate produced in step (g), or filtering the third column eluate or the concentrated third column eluate produced in step (h), thereby producing purified rAAV particles.

In certain embodiments of all aspects and embodiments, concentrating of step (b) and/or step (f) and/or step (g) and/or step (h) is via ultrafiltration/diafiltration, such as by tangential flow filtration (TFF).

In certain embodiments of all aspects and embodiments, concentrating of step (b) reduces the volume of the harvested cells and cell culture supernatant by about 2-20 fold.

In certain embodiments of all aspects and embodiments, concentrating of step (f) and/or step (g) and/or step (h) reduces the volume of the column eluate by about 5-20 fold.

In certain embodiments of all aspects and embodiments, lysing of the harvest produced in step (a) or the concentrated harvest produced in step (b) is by physical or chemical means. Non-limiting examples of physical means include microfluidization and homogenization. Non-limiting examples of chemical means include detergents. Detergents include non-ionic and ionic detergents. Non-limiting examples of non-ionic detergents include Triton X-100. Non-limiting examples of detergent concentration is between about 0.1 and 1.0% (v/v) or (w/v), inclusive.

In certain embodiments of all aspects and embodiments, step (d) comprises treating with a nuclease thereby reducing contaminating nucleic acid. Non-limiting examples of a nuclease include benzonase.

In certain embodiments of all aspects and embodiments, filtering of the clarified lysate or the diluted clarified lysate of step (e) is via a filter. Non-limiting examples of filters are those having a pore diameter of between about 0.1 and 10.0 microns, inclusive.

In certain embodiments of all aspects and embodiments, diluting of the clarified lysate of step (e) is with an aqueous buffered phosphate, acetate or Tris solution. Non-limiting examples of solution pH are between about pH 4.0 and pH 7.4, inclusive. Non-limiting examples of Tris solution pH are greater than pH 7.5, such as between about pH 8.0 and pH 9.0, inclusive.

In certain embodiments of all aspects and embodiments, diluting of the column eluate of step (f) or the second column eluate of step (g) is with an aqueous buffered phosphate, acetate or Tris solution. Non-limiting examples of solution pH are between about pH 4.0 and pH 7.4, inclusive. Non-limiting examples of Tris solution pH are greater than pH 7.5, such as between about pH 8.0 and pH 9.0, inclusive.

In certain embodiments of all aspects and embodiments, the rAAV particles resulting from step (i) are formulated with a surfactant to produce a rAAV particle formulation.

In certain embodiments of all aspects and embodiments, the anion exchange column chromatography of step (f), (g) and/or (h) comprises polyethylene glycol (PEG) modulated column chromatography.

In certain embodiments of all aspects and embodiments, the anion exchange column chromatography of step (g) and/or (h) is washed with a PEG solution prior to elution of the rAAV particles from the column. In certain embodiments of all aspects and embodiments, the PEG has an average molecular weight in a range of about 1,000 g/mol to 80,000 g/mol, inclusive. In certain embodiments of all aspects and embodiments, the PEG is at a concentration of about 4% to about 10% (w/v), inclusive.

In certain embodiments of all aspects and embodiments, the anion exchange column of step (g) and/or (h) is washed with an aqueous surfactant solution prior to elution of the rAAV particles from the column.

In certain embodiments of all aspects and embodiments, the cation exchange column of step (f) is washed with a surfactant solution prior to elution of the rAAV particles from the column.

In certain embodiments of all aspects and embodiments, the PEG solution and/or the surfactant solution comprises an aqueous Tris-HCl/NaCl buffer, an aqueous phosphate/NaCl buffer, or an aqueous acetate/NaCl buffer.

In certain embodiments of all aspects and embodiments, NaCl concentration in the buffer or solution is in a range of between about 20-300 mM NaCl, inclusive, or between about 50-250 mM NaCl, inclusive.

In certain embodiments of all aspects and embodiments, the surfactant comprises a cationic or anionic surfactant.

In certain embodiments of all aspects and embodiments, the surfactant comprises a twelve carbon chained surfactant.

In certain embodiments of all aspects and embodiments, the surfactant comprises Dodecyltrimethylammonium chloride (DTAC) or Sarkosyl.

In certain embodiments of all aspects and embodiments, the rAAV particles are eluted from the anion exchange column of step (f), (g) and/or (h) with an aqueous Tris-HCl/NaCl buffer.

In certain embodiments of all aspects and embodiments, the Tris-HCl/NaCl buffer comprises 100-400 mM NaCl, inclusive, optionally at a pH in a range of about pH 7.5 to about pH 9.0, inclusive.

In certain embodiments of all aspects and embodiments, the anion exchange column of step (f), (g) and/or (h) is washed with an aqueous Tris-HCl/NaCl buffer.

In certain embodiments of all aspects and embodiments, the NaCl concentration in the aqueous Tris-HCl/NaCl buffer is in a range of about 75-125 mM, inclusive.

In certain embodiments of all aspects and embodiments, the aqueous Tris-HCl/NaCl buffer has a pH from about pH 7.5 to about pH 9.0, inclusive.

In certain embodiments of all aspects and embodiments, the anion exchange column of step (f), (g) and/or (h) is washed one or more times to reduce the amount of empty capsids in the second or third column eluate.

In certain embodiments of all aspects and embodiments, the anion exchange column wash removes empty capsids from the column prior to rAAV particle elution and/or instead of rAAV particle elution, thereby reducing the amount of empty capsids in the second or third column eluate.

In certain embodiments of all aspects and embodiments, the anion exchange column wash removes at least about 50% of the total empty capsids from the column prior to rAAV particle elution and/or instead of rAAV particle elution, thereby reducing the amount of empty capsids in the second or third column eluate by about 50%.

In certain embodiments of all aspects and embodiments, the NaCl concentration in the aqueous Tris-HCl/NaCl buffer is in a range of about 110-120 mM, inclusive.

In certain embodiments of all aspects and embodiments, ratios and/or amounts of the rAAV particles and empty capsids eluted are controlled by a wash buffer.

In certain embodiments of all aspects and embodiments, the rAAV particles are eluted from the cation exchange column of step (f) in an aqueous phosphate/NaCl buffer, or an aqueous acetate/NaCl buffer. Non-limiting NaCl concentration in a buffer is in a range of about 125-500 mM NaCl, inclusive. Non-limiting examples of buffer pH are between about pH 5.5 to about pH 7.5, inclusive.

In certain embodiments of all aspects and embodiments, the anion exchange column of step (f), (g) and/or (h) comprises a quaternary ammonium functional group such as quaternized polyethylenimine.

In certain embodiments of all aspects and embodiments, the size exclusion column (SEC) of step (g) and/or (h) has a separation/fractionation range (molecular weight) from about 10,000 g/mol to about 600,000 g/mol, inclusive.

In certain embodiments of all aspects and embodiments, the cation exchange column of step (f) comprises a sulfonic acid or functional group such as sulphopropyl.

In certain embodiments of all aspects and embodiments, the AAV affinity column comprises a protein or ligand that binds to AAV capsid protein. Non-limiting examples of a protein include an antibody that binds to AAV capsid protein. More specific non-limiting examples include a single-chain Llama antibody (Camelid) that binds to AAV capsid protein.

In certain embodiments of all aspects and embodiments, the method excludes a step of cesium chloride gradient ultracentrifugation.

In certain embodiments of all aspects and embodiments, the method recovers approximately 50-90% of the total rAAV particles from the harvest produced in step (a) or the concentrated harvest produced in step (b).

In certain embodiments of all aspects and embodiments, the method produces rAAV particles having a greater purity than rAAV particles produced or purified by a single AAV affinity column purification.

In certain embodiments of all aspects and embodiments, steps (c) and (d) are performed substantially concurrently.

In certain embodiments of all aspects and embodiments, the NaCl concentration is adjusted to be in a range of about 100-400 mM NaCl, inclusive, or in a range of about 140-300 mM NaCl, inclusive, after step (c) but prior to step (f).

In certain embodiments of all aspects and embodiments, the rAAV particles are derived from an AAV selected from the group consisting of AAV1, AAV2, AAV3, AAV4, AAV5, AAV6, AAV7, AAV8, AAV9, AAV10, Rh 10 and Rh74.

In certain embodiments of all aspects and embodiments, the rAAV particles comprise a capsid sequence having 70% or more sequence identity to an AAV1, AAV2, AAV3, AAV4, AAV5, AAV6, AAV7, AAV8, AAV9, AAV10, Rh 10, Rh74, SEQ ID NO: 75, or SEQ ID NO: 76 capsid sequence.

In certain embodiments of all aspects and embodiments, the rAAV particles comprise an ITR sequence having 70% or more sequence identity to an AAV1, AAV2, AAV3, AAV4, AAV5, AAV6, AAV7, AAV8, AAV9, AAV10, Rh 10, or Rh74 ITR sequence.

In certain embodiments of all aspects and embodiments, the cells are suspension growing or adherent growing cells.

In certain embodiments of all aspects and embodiments, the cells are mammalian cells. Non-limiting examples include HEK cells, such as HEK-293 cells, and CHO cells, such as CHO-K1 cells.

Methods to determine infectious titer of rAAV particles containing a transgene are known in the art (see, e.g., Zhen et al., Hum. Gene Ther. 15 (2004) 709). Methods for assaying for empty capsids and rAAV particles with packaged transgenes are known (see, e.g., Grimm et al., Gene Therapy 6 (1999) 1322-1330; Sommer et al., Malec. Ther. 7 (2003) 122-128).

To determine the presence or amount of degraded/denatured capsid, purified rAAV particle can be subjected to SDS-polyacrylamide gel electrophoresis, consisting of any gel capable of separating the three capsid proteins, for example, a gradient gel, then running the gel until sample is separated, and blotting the gel onto nylon or nitrocellulose membranes. Anti-AAV capsid antibodies are then used as primary antibodies that bind to denatured capsid proteins (see, e.g., Wobus et al., J. Viral. 74 (2000) 9281-9293). A secondary antibody that binds to the primary antibody contains a means for detecting the primary antibody. Binding between the primary and secondary antibodies is detected semi-quantitatively to determine the amount of capsids. Another method would be analytical HPLC with a SEC column or analytical ultracentrifuge.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

All references mentioned herein are incorporated herewith by reference.

The following examples, sequences and figures are provided to aid the understanding of the present invention, the true scope of which is set forth in the appended claims. It is understood that modifications can be made in the procedures set forth without departing from the spirit of the invention.

EXAMPLES

General Techniques

1) Recombinant DNA Techniques

Figure 1:
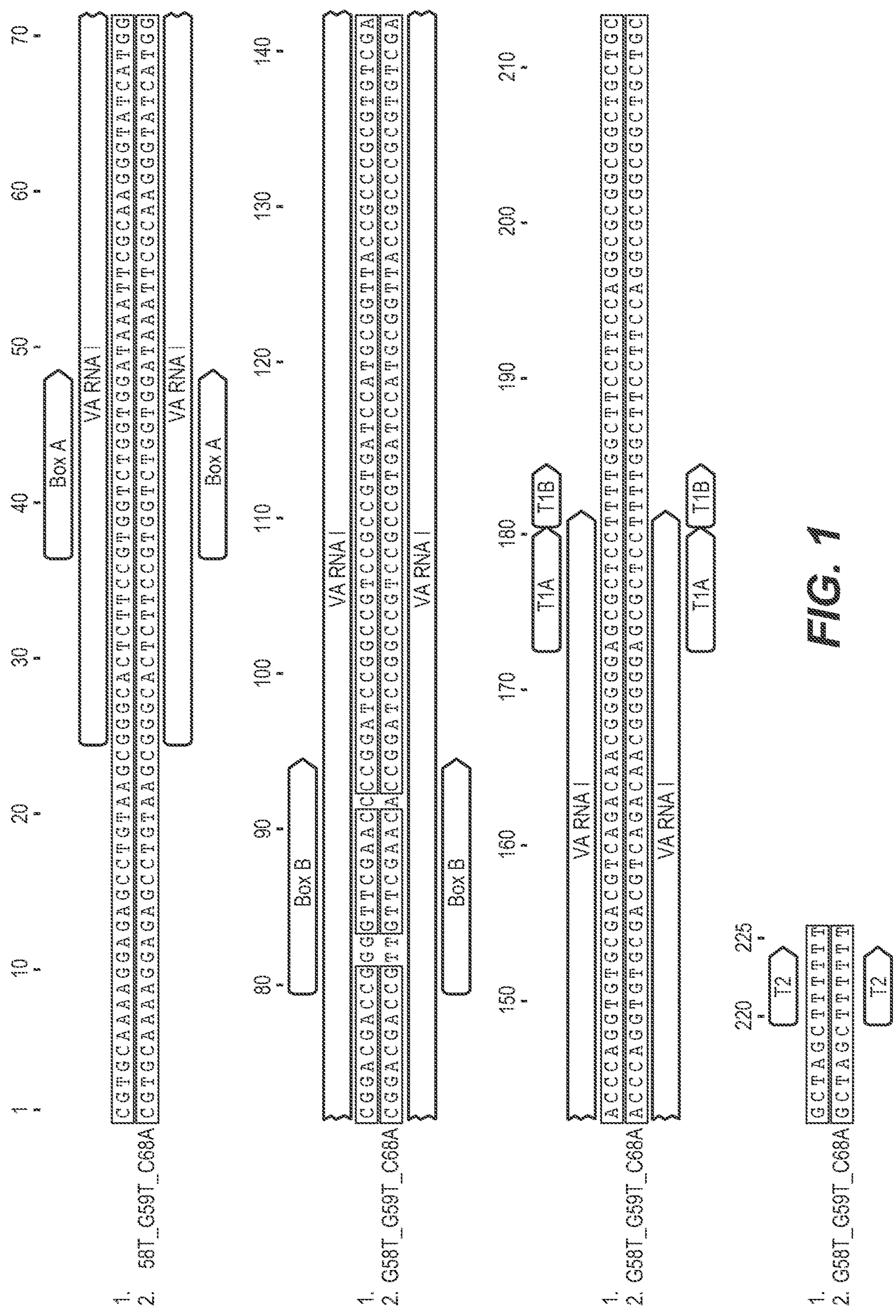
FIG. 1 Alignment of adenoviral VA RNA and adenoviral VA RNA G58T/G59T/C68A variant.

Standard methods are used to manipulate DNA as described in Sambrook et al., Molecular Cloning: A Laboratory Manual, Second Edition, Cold Spring Harbor Laboratory Press, Cold Spring Harbor, N.Y, (1989). The molecular biological reagents are used according to the manufacturer's instructions.

2) DNA and Protein Sequence Analysis and Sequence Data Management

The EMBOSS (European Molecular Biology Open Software Suite) software package, Invitrogen's Vector NTI and Geneious Prime and are used for sequence creation, mapping, analysis, annotation and illustration.

3) Gene and Oligonucleotide Synthesis

Desired gene segments are prepared by chemical synthesis at Geneart GmbH (Regensburg, Germany). The synthesized gene fragments are cloned into an *E. coli* plasmid for propagation/amplification. The DNA sequences of subcloned gene fragments are verified by DNA sequencing. Alternatively, short synthetic DNA fragments are assembled by annealing chemically synthesized oligonucleotides or via PCR. The respective oligonucleotides are prepared by metabion GmbH (Planegg-Martinsried, Germany).

4) Reagents

All commercial chemicals, antibodies and kits are used as provided according to the manufacturer's protocol if not stated otherwise.

5) Cultivation of TI Host Cell Line

TI CHO host cells are cultivated at 37° C. in a humidified incubator with 85% humidity and 5% $CO_2$. They are cultivated in a proprietary DMEM/F12-based medium containing 300 μg/ml Hygromycin B and 4 μg/ml of a second selection marker. The cells are splitted every 3 or 4 days at a concentration of 0.3×10E6 cells/ml in a total volume of 30 ml. For the cultivation 125 ml non-baffle Erlenmeyer shake flasks are used. Cells are shaken at 150 rpm with a shaking amplitude of 5 cm. The cell count is determined with Cedex HiRes Cell Counter (Roche). Cells are kept in culture until they reached an age of 60 days.

6) Cloning

General

Cloning with R-sites depends on DNA sequences next to the gene of interest (GOI) that are equal to sequences lying in following fragments. Like that, assembly of fragments is possible by overlap of the equal sequences and subsequent sealing of nicks in the assembled DNA by a DNA ligase. Therefore, a cloning of the single genes in particular preliminary plasmids containing the right R-sites is necessary. After successful cloning of these preliminary plasmids the gene of interest flanked by the R-sites is cut out via restriction digest by enzymes cutting directly next to the R-sites. The last step is the assembly of all DNA fragments in one step. In more detail, a 5'-exonuclease removes the 5'-end of the overlapping regions (R-sites). After that, annealing of the R-sites can take place and a DNA polymerase extends the 3'-end to fill the gaps in the sequence. Finally, the DNA ligase seals the nicks in between the nucleotides. Addition of an assembly master mix containing different enzymes like exonucleases, DNA polymerases and ligases, and subsequent incubation of the reaction mix at 50° C. leads to an assembly of the single fragments to one plasmid. After that, competent *E. coli* cells are transformed with the plasmid.

For some plasmids, a cloning strategy via restriction enzymes was used. By selection of suitable restriction enzymes, the wanted gene of interest can be cut out and afterwards inserted into a different plasmid by ligation. Therefore, enzymes cutting in a multiple cloning site (MCS) are preferably used and chosen in a smart manner, so that a ligation of the fragments in the correct array can be conducted. If plasmid and fragment are previously cut with the same restriction enzyme, the sticky ends of fragment and plasmid fit perfectly together and can be ligated by a DNA ligase, subsequently. After ligation, competent *E. coli* cells are transformed with the newly generated plasmid.

Cloning Via Restriction Digestion

For the digest of plasmids with restriction enzymes the following components are pipetted together on ice:

TABLE

Restriction Digestion Reaction Mix

| component | ng (set point) | μl |
|---|---|---|
| purified DNA | tbd | tbd |
| CutSmart Buffer (10×) | | 5 |
| Restriction Enzyme | | 1 |
| PCR-grade Water | | ad 50 |
| Total | | 50 |

If more enzymes are used in one digestion, 1 μl of each enzyme is used and the volume is adjusted by addition of more or less PCR-grade water. All enzymes are selected on the preconditions that they are qualified for the use with CutSmart buffer from new England Biolabs (100% activity) and have the same incubation temperature (all 37° C.).

Incubation is performed using thermomixers or thermal cyclers, allowing incubating the samples at a constant temperature (37° C.). During incubation, the samples are not agitated. Incubation time is set at 60 min. Afterwards the samples are directly mixed with loading dye and loaded onto an agarose electrophoresis gel or stored at 4° C./on ice for further use.

A 1% agarose gel is prepared for gel electrophoresis. Therefor 1.5 g of multi-purpose agarose are weighed into a 125 Erlenmeyer shake flask and filled up with 150 ml TAE-buffer. The mixture is heated up in a microwave oven until the agarose is completely dissolved. 0.5 μg/ml ethidium bromide are added into the agarose solution. Thereafter the gel is cast in a mold. After the agarose is set, the mold is placed into the electrophoresis chamber and the chamber is filled with TAE-buffer. Afterwards the samples are loaded. In the first pocket (from the left), an appropriate DNA molecular weight marker is loaded, followed by the samples. The gel is run for around 60 minutes at <130 V. After electrophoresis, the gel is removed from the chamber and analyzed in an UV-Imager.

The target bands are cut and transferred to 1.5 ml Eppendorf tubes. For purification of the gel, the QIAquick Gel Extraction Kit from Qiagen is used according to the manufacturer's instructions. The DNA fragments are stored at −20° C. for further use.

The fragments for the ligation are pipetted together in a molar ratio of 1:2, 1:3 or 1:5 plasmid to insert, depending on the length of the inserts and the plasmid-fragments and their correlation to each other. If the fragment, that should be inserted into the plasmid is short, a 1:5-ratio is used. If the insert is longer, a smaller amount of it is used in correlation to the plasmid. An amount of 50 ng of plasmid is used in each ligation and the particular amount of insert calculated with NEBioCalculator. For ligation, the T4 DNA ligation kit from NEB is used. An example for the ligation mixture is depicted in the following Table.

TABLE

Ligation Reaction Mix

| component | ng (set point) | conc. [ng/μl] | μl |
|---|---|---|---|
| T4 DNA Ligase Buffer (10×) | | | 2 |
| Plasmid DNA (4000 bp) | 50 | 50 | 1 |
| Insert DNA (2000 bp) | 125 | 20 | 6.25 |
| Nuclease-free Water | | | 9.75 |
| T4 Ligase | | | 1 |
| Total | | | 20 |

All components are pipetted together on ice, starting with the mixing of DNA and water, addition of buffer and finally addition of the enzyme. The reaction is gently mixed by pipetting up and down, briefly microfuged and then incubated at room temperature for 10 minutes. After incubation, the T4 ligase is heat inactivated at 65° C. for 10 minutes. The sample is chilled on ice. In a final step, 10-beta competent *E. coli* cells are transformed with 2 μl of the ligated plasmid (see below).

Transformation 10-Beta Competent *E. coli* Cells

For transformation, the 10-beta competent *E. coli* cells are thawed on ice. After that, 2 μl of plasmid DNA is pipetted directly into the cell suspension. The tube is flicked and put on ice for 30 minutes. Thereafter, the cells are placed into a 42° C. thermal block and heat-shocked for exactly 30 seconds. Directly afterwards, the cells are chilled on ice for 2 minutes. 950 μl of NEB 10-beta outgrowth medium are added to the cell suspension. The cells are incubated under shaking at 37° C. for one hour. Then, 50-100 μl are pipetted onto a pre-warmed (37° C.) LB-Amp agar plate and spread with a disposable spatula. The plate is incubated overnight at 37° C. Only bacteria, which have successfully incorporated the plasmid, carrying the resistance gene against ampicillin, can grow on these plates. Single colonies are picked the next day and cultured in LB-Amp medium for subsequent plasmid preparation.

Bacterial Culture

Cultivation of *E. coli* is done in LB-medium, short for Luria Bertani, which is spiked with 1 ml/L 100 mg/ml ampicillin resulting in an ampicillin concentration of 0.1 mg/ml. For the different plasmid preparation quantities, the following amounts are inoculated with a single bacterial colony.

TABLE

*E. coli* cultivation volumes

| Quantity plasmid preparation | Volume LB-Amp medium [ml] | Incubation time [h] |
|---|---|---|
| Mini-Prep 96-well (EpMotion) | 1.5 | 23 |
| Mini-Prep 15 ml-tube | 3.6 | 23 |
| Maxi-Prep | 200 | 16 |

For Mini-Prep, a 96-well 2 ml deep-well plate is filled with 1.5 ml LB-Amp medium per well. The colonies are picked and the toothpick is tuck in the medium. When all colonies are picked, the plate is closed with a sticky air porous membrane. The plate is incubated in a 37° C. incubator at a shaking rate of 200 rpm for 23 hours.

For Mini-Preps a 15 ml-tube (with a ventilated lid) is filled with 3.6 ml LB-Amp medium and equally inoculated with a bacterial colony. The toothpick is not removed but left in the tube during incubation. Like the 96-well plate, the tubes are incubated at 37° C., 200 rpm for 23 hours.

For Maxi-Prep 200 ml of LB-Amp medium are filled into an autoclaved glass 1 L Erlenmeyer flask and are inoculated with 1 ml of bacterial day-culture, that is roundabout 5 hours old. The Erlenmeyer flask is closed with a paper plug and incubated at 37° C., 200 rpm for 16 hours.

Plasmid Preparation

For Mini-Prep, 50 μl of bacterial suspension are transferred into a 1 ml deep-well plate. After that, the bacterial cells are centrifuged down in the plate at 3000 rpm, 4° C. for 5 min. The supernatant is removed and the plate with the bacteria pellets is placed into an EpMotion. After approx. 90 minutes, the run is done and the eluted plasmid-DNA can be removed from the EpMotion for further use.

For Mini-Prep, the 15 ml tubes are taken out of the incubator and the 3.6 ml bacterial culture is splitted into two 2 ml Eppendorf tubes. The tubes are centrifuged at 6,800×g in a tabletop microcentrifuge for 3 minutes at room temperature. After that, Mini-Prep is performed with the Qiagen QIAprep Spin Miniprep Kit according to the manufacturer's instructions. The plasmid DNA concentration is measured with Nanodrop.

Maxi-Prep is performed using the Macherey-Nagel NucleoBond® Xtra Maxi EF Kit according to the manufacturer's instructions. The DNA concentration is measured with Nanodrop.

Ethanol Precipitation

The volume of the DNA solution is mixed with the 2.5-fold volume ethanol 100%. The mixture is incubated at −20° C. for 10 min. Then the DNA is centrifuged for 30 min. at 14,000 rpm, 4° C. The supernatant is carefully removed and the pellet is washed with 70% ethanol. Again, the tube is centrifuged for 5 min. at 14,000 rpm, 4° C. The supernatant is carefully removed by pipetting and the pellet is dried. When the ethanol is evaporated, an appropriate amount of endotoxin-free water is added. The DNA is given time to re-dissolve in the water overnight at 4° C. A small aliquot is taken and the DNA concentration is measured with a Nanodrop device.

Expression Cassette Composition

For the expression of an open reading frame, a transcription unit comprising the following functional elements is used:

- the immediate early enhancer and promoter from the human cytomegalovirus including intron A,
- a human heavy chain immunoglobulin 5'-untranslated region (5'UTR),
- a nucleic acid comprising the respective open reading frame including signal sequences, if required,
- the bovine growth hormone polyadenylation sequence (BGH pA), and
- optionally the human gastrin terminator (hGT).

Beside the expression unit/cassette including the desired gene to be expressed, the basic/standard mammalian expression plasmid contains

- an origin of replication from the plasmid pUC18 which allows replication of this plasmid in *E. coli*, and
- a beta-lactamase gene which confers ampicillin resistance in *E. coli*.

Cell Culture Techniques

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293 System

Cells comprising the DNA elements according to the current invention are generated by transient transfection with the respective plasmids (see Examples 1 to 4 below) using the HEK293 system (Invitrogen) according to the manufacturer's instruction. Briefly, HEK293 cells (Invitrogen) growing in suspension either in a shake flask or in a stirred fermenter in serum-free FreeStyle™ 293 expression medium (Invitrogen) are transfected with a mix of the respective plasmids and 293fectin™ or fectin (Invitrogen). For 2 L shake flask (Corning), HEK293 cells are seeded at a density of $1*10^6$ cells/mL in 600 mL and are incubated at 120 rpm, 8% $CO_2$. The day after the cells are transfected at a cell density of ca. $1.5*10^6$ cells/mL with ca. 42 mL mix of A) 20 mL Opti-MEM (Invitrogen) with 600 μg total plasmid DNA (1 μg/mL) and B) 20 ml Opti-MEM+1.2 mL 293 fectin or fectin (2 μL/mL). According to the glucose consumption, glucose solution is added during the course of the fermentation.

SDS-PAGE

LDS sample buffer, fourfold concentrate (4×): 4 g glycerol, 0.682 g TRIS-Base, 0.666 g TRIS-hydrochloride, 0.8 g LDS (lithium dodecyl sulfate), 0.006 g EDTA (ethylene diamine tetra acid), 0.75 ml of a 1% by weight (w/w) solution of Serva Blue G250 in water, 0.75 ml of a 1% by weight (w/w) solution of phenol red, add water to make a total volume of 10 ml.

The cells in the culture broth are lysed. Thereafter the solution was centrifuged to remove cell debris. An aliquot of the clarified supernatant is admixed with ¼ volumes (v/v) of 4xLDS sample buffer and 1/10 volume (v/v) of 0.5 M 1,4-dithiotreitol (DTT). Then the samples are incubated for 10 min. at 70° C. and protein separated by SDS-PAGE. The NuPAGE® Pre-Cast gel system (Invitrogen Corp.) was used according to the manufacturer's instruction. In particular, 10% NuPAGE® Novex® Bis-TRIS Pre-Cast gels (pH 6.4) and a NuPAGE® MOPS running buffer was used.

Western Blot

Transfer buffer: 39 mM glycine, 48 mM TRIS-hydrochloride, 0.04% by weight (w/w) SDS, and 20% by volume methanol (v/v)

After SDS-PAGE the separated polypeptides were transferred electrophoretically to a nitrocellulose filter membrane (pore size: 0.45 μm) according to the "Semidry-Blotting-Method" of Burnette (Burnette, W. N., Anal. Biochem. 112 (1981) 195-203).

Example 1

Generation of a DNA for Adenoviral VA RNAI Transcription by Human U6 Promoter According to the Invention A DNA fragment comprising in 5'- to 3'-direction the human U6 promoter sequence (the distance between TATA and the transcription start site as well as the nucleotide sequence of the U6 promoter was kept unchanged; SEQ ID NO: 42) and the adenoviral serotype 2 (Ad2) VA RNAI gene (GenBank AC_000007) including the polymerase III terminator sequence (SEQ ID NO: 33) is chemically synthesized.

The fragment is ligated with a plasmid backbone carrying a puromycin selection marker, yielding a plasmid for stable transfection of mammalian cells.

Figure 2:
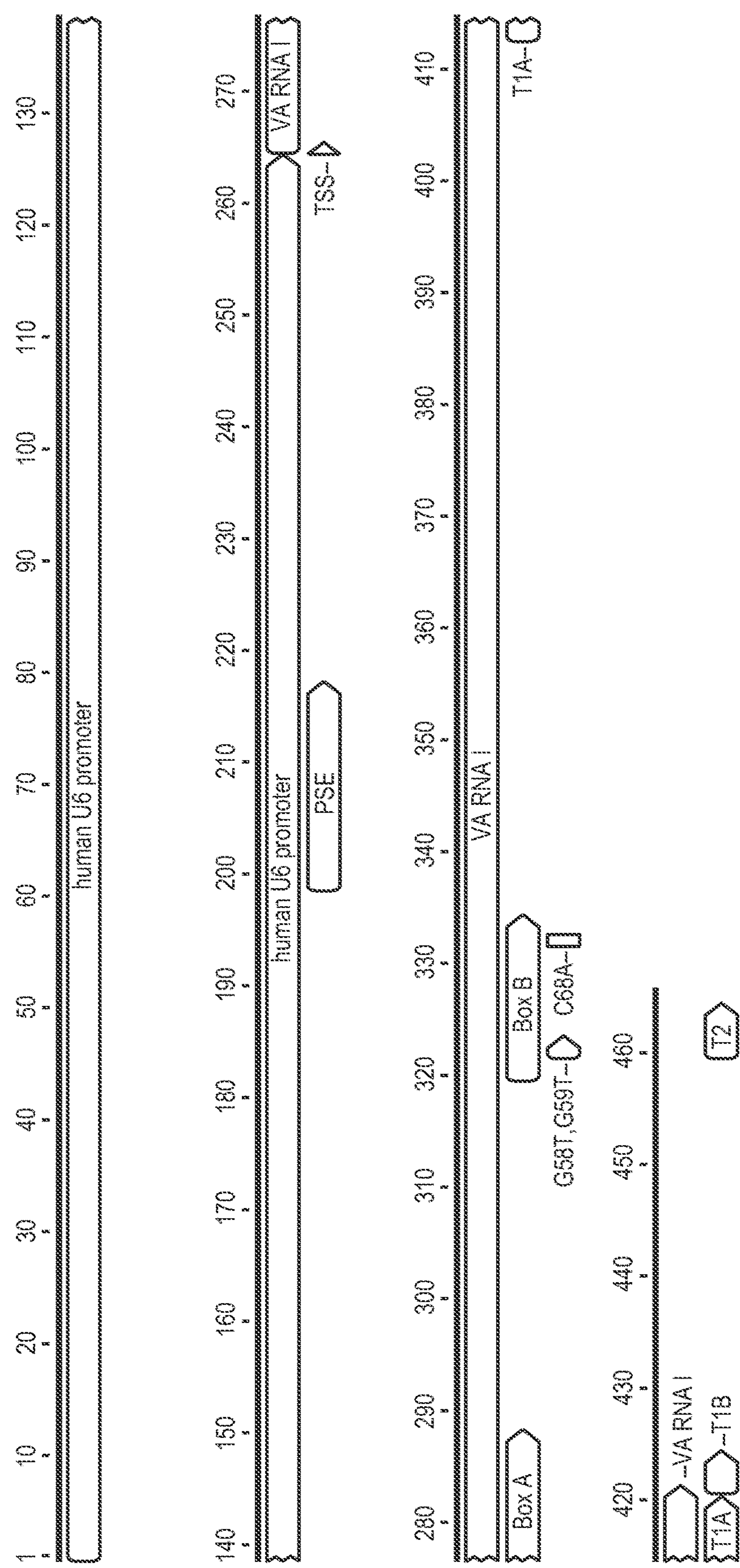
FIG. 2 Scheme of an embodiment of the invention wherein the human U6 promoter is operably linked to the adenoviral VA RNAI sequence.

FIG. 2 illustrates the order and orientation of the elements within this DNA fragment.

Example 2

Stable Integration

CHO-K1 cells, adapted to grow in suspension, are propagated in 50 mL chemically defined medium in disposable, vented 125 mL shake flasks at 37° C. and 5-7 vol.-% $CO_2$. The cultures are shaken with a constant agitation rate of 140-180 rpm/min and diluted every 3-4 days to a density of $2\text{-}3\times10^5$ cells/mL with fresh medium. The density and viability of the cultures are determined using Cedex HiRes cell counter (Roche Innovates AG, Bielefeld, Germany).

For stable integration of the nucleic acid of Example 1, the suspension-growing CHO-K1 cells are seeded in fresh chemically defined medium with a density of $4\times10^5$ cells/mL. On the following day, transfection is performed with the Nucleofector device using the Nucleofector Kit V (Lonza, Switzerland) according to the manufacturer's protocol. $3\times10^7$ cells are transfected with 30 μg linearized plasmid DNA. After transfection, the cells are seeded in 30 ml fresh chemically defined medium without selection agents.

Two days after transfection, cells are seeded into 384-well plates containing 1 to 10 μg/mL puromycin as selection agent with 300 to 500 cells per well. After three weeks, cell colonies are identified by imaging using a NYONE Plate imager (SYNENTECH GmbH, Elmshom, Germany). Colonies are transferred to 96-well plates and analyzed for integration by PCR. Cell lines containing the nucleic acid are further expanded in chemically defined medium containing puromycin and are cryo-preserved after expansion.

Example 3

AAV Particle Production

For the production of recombinant AAV particles, $3\times10^{7}$ cells obtained according to Example 2 are transfected with a total amount of 30 μg nucleic acid composed of plasmid DNA providing a recombinant AAV genome (transgene, e.g. a GFP gene flanked by AAV ITRs) and expression cassettes for helper genes and/or the rep/cap gene that have not been integrated into the genome of the cell yet.

One day prior to transfection, cells are seeded in fresh medium with a density of $4\times10^{5}$ cells/mL. On the following day, transfection is performed with the Nucleofector device using the Nucleofector Kit V (Lonza, Switzerland) according to the manufacturer's protocol.

Alternatively, the plasmids are sequentially stably integrated integration into the genome of the host cell with the rep/cap genes last.

AAV particles are harvested from the cell culture supernatant or the total cell lysate and are analyzed by ELISA, quantitative PCR and transduction of target cells.

What is claimed is:

1. An adenoviral VA RNA nucleic acid comprising in 5'- to 3'-direction a human U6 RNA promoter, and an adenoviral VA RNA coding sequence of SEQ ID NO: 38.

2. An adenoviral VA RNA nucleic acid comprising in 5'- to 3'-direction an inducible promoter, and an adenoviral VA RNA coding sequence of SEQ ID NO: 38.

3. A DNA comprising an adenoviral VA RNA nucleic acid, and a DNA element comprising an E1A open reading frame and an E1B open reading frame; or an E2A open reading frame and an E4 or E4orf6 open reading frame; or a rep open reading frame and a cap open reading frame, wherein the adenoviral VA RNA nucleic acid further comprises (i) either a human U6 RNA promoter or an inducible promoter, and (ii) an adenoviral VA RNA coding sequence of SEQ ID NO: 38.

4. An isolated mammalian cell or an isolated insect cell comprising an adenoviral VA RNA nucleic acid that further comprises (i) either a human U6 RNA promoter or an inducible promoter, and (ii) an adenoviral VA RNA coding sequence of SEQ ID NO: 38.

5. A method for producing recombinant adeno-associated virus (rAAV) particles comprising:

providing a mammalian cell, growing in suspension in cultivation medium, which comprises:

a transgene expression cassette interspaced between two AAV ITRs;

open reading frames encoding adenoviral E1A, E1B, E2A, E4 or E4orf6 proteins;

an adenoviral VA RNA nucleic acid comprising (i) either a human U6 RNA promoter or an inducible promoter, and (ii) an adenoviral VA RNA coding sequence of SEQ ID NO: 38;

open reading frames encoding adeno-associated viral Rep or Cap proteins;

cultivating the mammalian cell; and isolating the rAAV particles from the mammalian cell or the cultivation medium and thereby producing rAAV particles.

6. The isolated mammalian cell or the isolated insect cell of claim 4 comprising a DNA further comprising:

an adenoviral VA RNA nucleic acid comprising (i) either a human U6 RNA promoter or an inducible promoter, and (ii) an adenoviral VA RNA coding sequence of SEQ ID NO: 38, and, a DNA element comprising: (i) an E1A open reading frame and an E1B open reading frame; or (ii) an E2A open reading frame and an E4 or E4orf6 open reading frame; or (iii) a rep open reading frame and a cap open reading frame.

* * * * *